US009445711B2

(12) United States Patent
Sitti et al.

(10) Patent No.: US 9,445,711 B2
(45) Date of Patent: Sep. 20, 2016

(54) SYSTEM AND METHOD TO MAGNETICALLY ACTUATE A CAPSULE ENDOSCOPIC ROBOT FOR DIAGNOSIS AND TREATMENT

(71) Applicant: Carnegie Mellon University, Center for Technology Transfer and Enterprise Creation, Pittsburgh, PA (US)

(72) Inventors: Metin Sitti, Pittsburgh, PA (US); Sehyuk Yim, Seoul (KR)

(73) Assignee: CARNEGIE MELLON UNIVERSITY, Pittsburgh, PA (US)

( * ) Notice: Subject to any disclaimer, the term of this patent is extended or adjusted under 35 U.S.C. 154(b) by 0 days.

(21) Appl. No.: 13/890,746

(22) Filed: May 9, 2013

(65) Prior Publication Data

US 2013/0303847 A1 Nov. 14, 2013

Related U.S. Application Data

(60) Provisional application No. 61/688,157, filed on May 9, 2012.

(51) Int. Cl.

| | |
|---|---|
| ***A61B 1/00*** | (2006.01) |
| ***A61B 1/04*** | (2006.01) |
| ***A61B 1/018*** | (2006.01) |
| ***A61B 5/00*** | (2006.01) |

(Continued)

(52) U.S. Cl.

CPC ........... *A61B 1/00158* (2013.01); *A61B 1/018* (2013.01); *A61B 1/041* (2013.01); *A61B 5/073* (2013.01); *A61B 5/6861* (2013.01); *A61B 34/73* (2016.02); *A61B 5/062* (2013.01); *A61B 5/6879* (2013.01); *A61B 10/02* (2013.01); *A61B 18/04* (2013.01); *A61B 2017/00221* (2013.01); *A61B 2034/731* (2016.02)

(58) Field of Classification Search

CPC ...................................................... A61B 1/041

USPC ............... 600/110, 104, 109, 114; 604/890.1

See application file for complete search history.

(56) References Cited

U.S. PATENT DOCUMENTS

| | | |
|---|---|---|
| 5,604,531 A | 2/1997 | Iddan et al. |
| 6,485,409 B1 | 11/2002 | Voloshin et al. |

(Continued)

FOREIGN PATENT DOCUMENTS

| | | |
|---|---|---|
| KR | 10-2009-0093680 A | 9/2009 |

OTHER PUBLICATIONS

Ye-Seon Hong et al., Korean Patent 10-2009-0093680, Machine Translation, 20 pages.*

(Continued)

*Primary Examiner* — Anhtuan T Nguyen
*Assistant Examiner* — Timothy J Neal
(74) *Attorney, Agent, or Firm* — David G. Oberdick; Michael G. Monyok

(57) ABSTRACT

Present invention describes a swallowable device with a soft, compliant exterior, whose shape can be changed through the use of magnetic fields, and which can be locomoted in a rolling motion through magnetic control from the exterior of the patient. The present invention could be used for a variety of medical applications inside the GI tract including but not limited to drug delivery, biopsy, heat cauterization, pH sensing, biochemical sensing, micro-surgery, and active imaging.

6 Claims, 61 Drawing Sheets

10 34 12 X 18 32A 14 16 20 22 19 50 24 26 32B 36 28 30

110 120 122 112A 126 130A 124 132A 130B 118 132B 130C 111 112B

(51) Int. Cl.

| | |
|---|---|
| ***A61B 5/07*** | (2006.01) |
| *A61B 5/06* | (2006.01) |
| *A61B 10/02* | (2006.01) |
| *A61B 18/04* | (2006.01) |
| *A61B 17/00* | (2006.01) |

(56) References Cited

U.S. PATENT DOCUMENTS

| | | | | |
|---|---|---|---|---|
| 7,039,453 | B2 * | 5/2006 | Mullick et al. | 600/476 |
| 7,083,579 | B2 | 8/2006 | Yokoi et al. | |
| 7,623,904 | B2 | 11/2009 | Uchiyama et al. | |
| 7,697,970 | B2 | 4/2010 | Uchiyama et al. | |
| 7,711,408 | B2 | 5/2010 | Uchiyama et al. | |
| 7,904,137 | B2 | 3/2011 | Uchiyama et al. | |
| 8,235,055 | B2 | 8/2012 | Mintchev et al. | |
| 8,430,810 | B2 | 4/2013 | Hassidov et al. | |
| 8,439,851 | B2 | 5/2013 | Chiba et al. | |
| 2004/0199054 | A1 | 10/2004 | Wakefield | |
| 2004/0236180 | A1 | 11/2004 | Uchiyama et al. | |
| 2007/0219405 | A1 | 9/2007 | Uchiyama et al. | |
| 2008/0300458 | A1 | 12/2008 | Kim et al. | |

OTHER PUBLICATIONS

Gersbach, F., "Magnetically guided capsule endoscope system from Siemens and Olympus for comfortable examination of the stomach—More than 50 participants in the first successful study", Siemens Press Release, UEGW 2010, Erlangen, Germany / Barcelona, Spain, pp. 1-2, Oct. 25, 2010.

Gersbach, F., "The journey into the self becomes reality: Siemens Healthcare and Olympus Medical Systems Corporation announce collaborative development of advanced magnetically guided capsule endoscope system for intragastric observation", Siemens Press Release, Erlangen, Germany, pp. 1-3, Apr. 30, 2010.

S. Yim, K. Goyal, and M. Sitti, "Magnetically Actuated Soft Capsule with Multi-modal Drug Release Function," IEEE/ ASME Trans. on Mechatronics, vol. 18, No. 4, pp. 1413-1418, Aug. 2013.

S. Yim and M. Sitti, "3-D localization method for a magnetically actuated soft capsule endoscope and its applications," IEEE Trans. on Robotics, vol. 29, No. 5, pp. 1139-1151, Oct. 2013.

S. Yim and M. Sitti, "Design and Analysis of a Magnetically Actuated and Compliant Capsule Endoscopic Robot," IEEE Trans. on Robotics, pp. 4810-4815, May 2011.

* cited by examiner

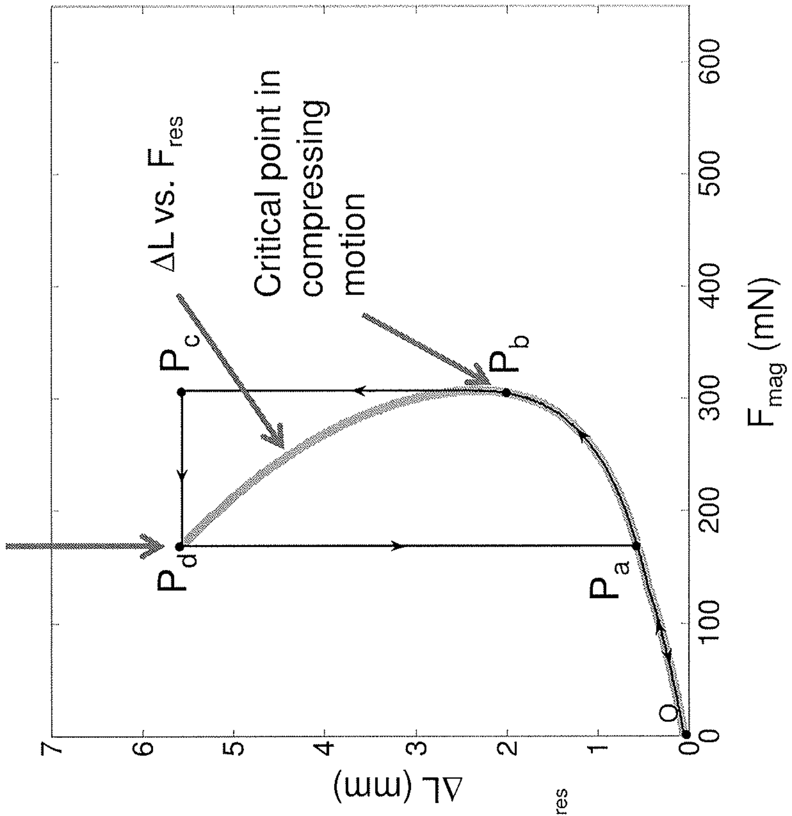
Fig. 4B
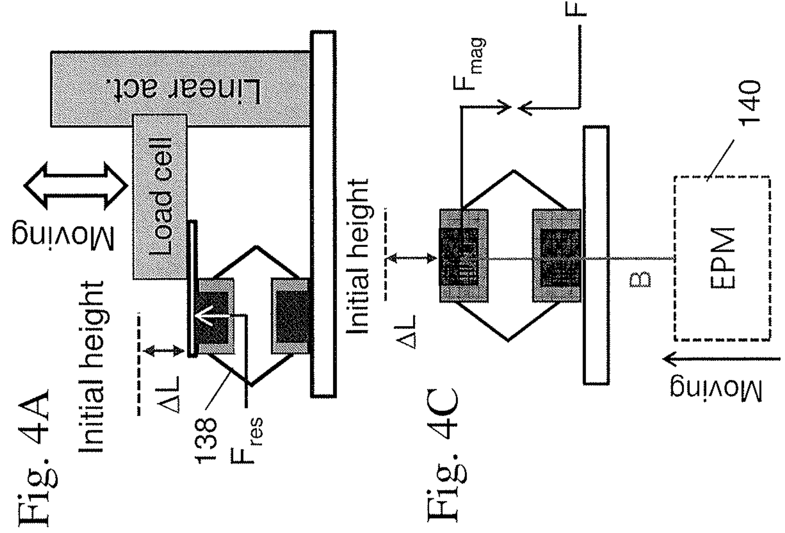
Fig. 4A
Fig. 4C

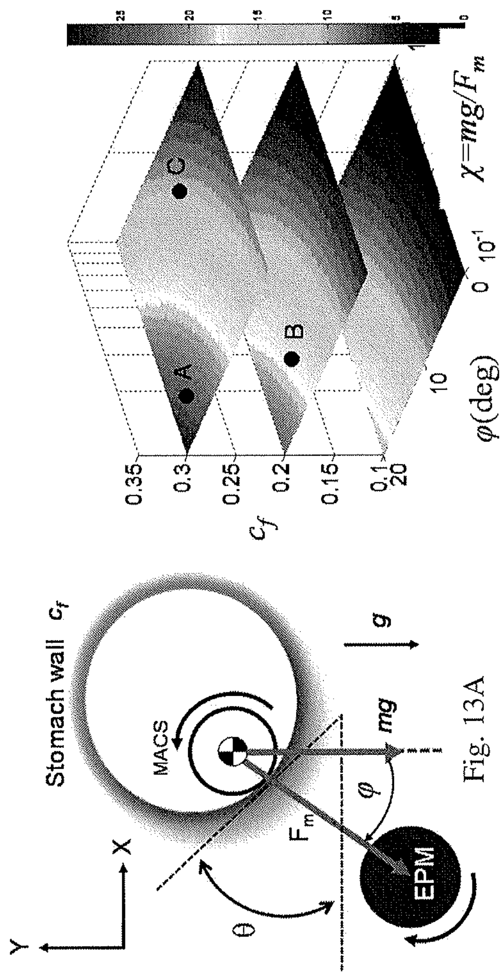
Fig. 13A
Fig. 13B
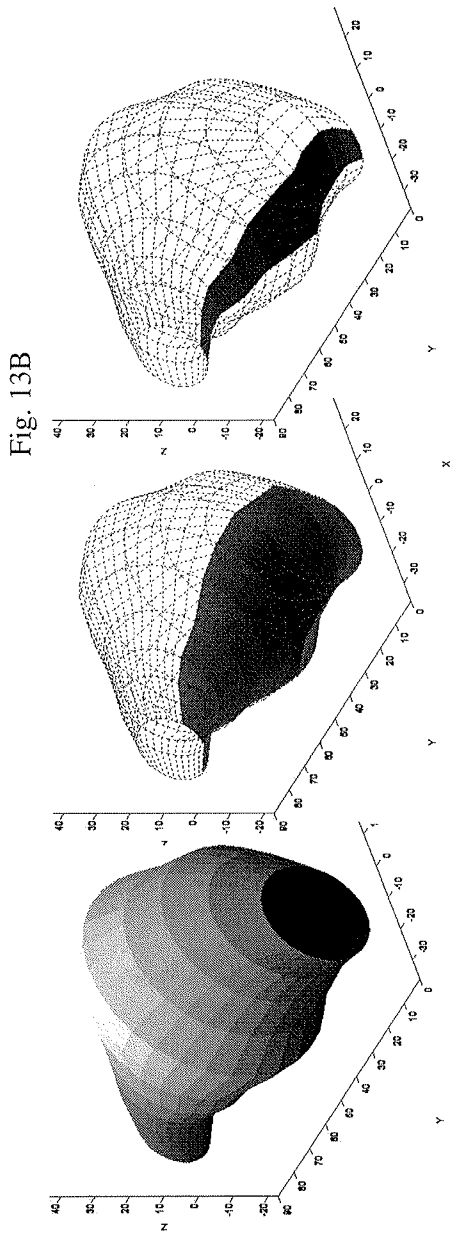
Fig. 13C 146
110

110
146
146
110

110
146
146
110
x
z 146
110

110
146

110
146

110
146

110
146
156

110
156
146

110
146
156

(a)-i
(a)-ii
(a)-iii
110
140

(b)-i
(b)-ii
(b)-iii

XY stage
Camera
Probe
166A
168
170
Z
Y
X
Fixed
B
h
110
172
Load cell
Z-stage
166A Stretched patch
$P_{i+1j+1}$
$L_{i,j+1}$
$P_{ij+1}$
176A
Original patch
$S_{i,j}$
$S_{i+1,j}$
168
$P_{ij}$
174
$L_{i,j}$
$P_{i+1j}$
168
$P_{ij+1}$
$\bar{L}$
$\bar{\varepsilon}_x$
176A
$\bar{S}$
$\bar{\varepsilon}_y$
$P_{ij}$
$P_{i+1j}$
174

66

Before
After

Before
After

Before
After

Fig. 54A
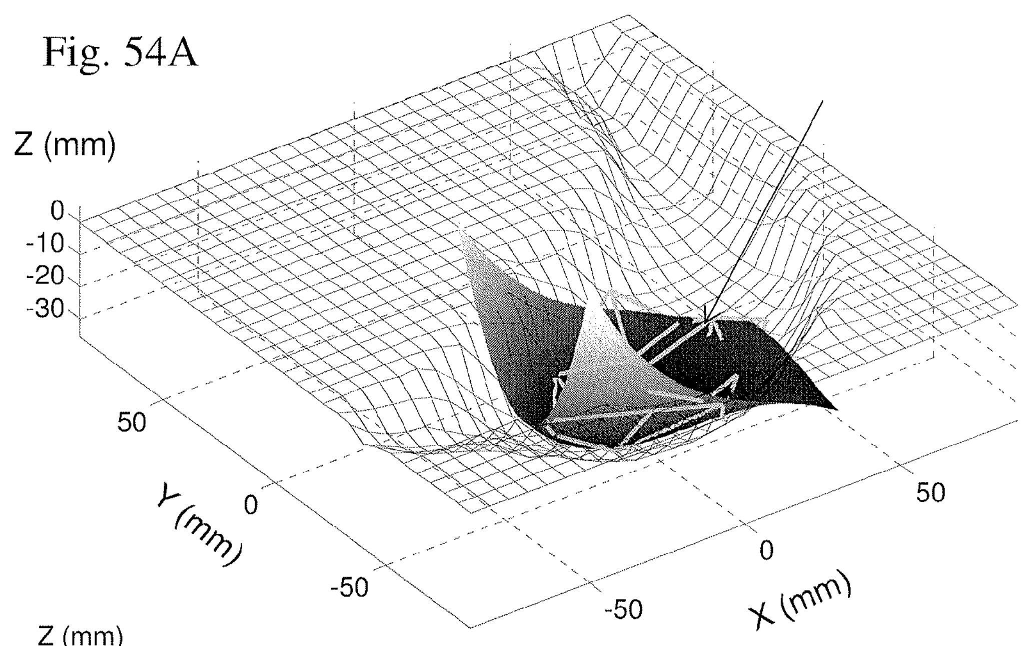
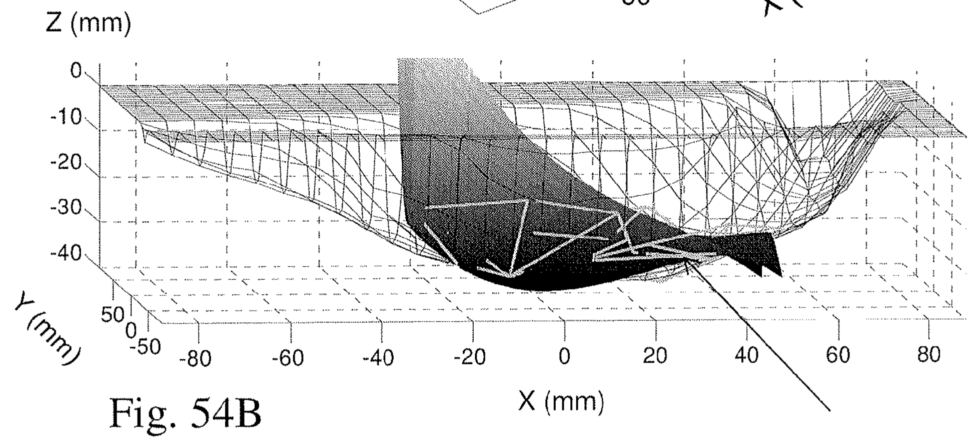
Fig. 54B

SYSTEM AND METHOD TO MAGNETICALLY ACTUATE A CAPSULE ENDOSCOPIC ROBOT FOR DIAGNOSIS AND TREATMENT

CROSS-REFERENCE TO RELATED APPLICATIONS

This application is a Non-provisional application claiming priority of U.S. Provisional Application No. 61/688,157, titled: ROBOTIC SOFT CAPSULE DEVICES, filed on May 9, 2012, herein incorporated by reference.

FIELD OF THE INVENTION

This invention relates to miniature capsule devices for medical applications. More particularly, this invention relates to soft capsule devices for medical applications inside the gastrointestinal tract or other regions inside the human body.

BACKGROUND OF THE INVENTION

Soft robots can change their shapes actively or passively for safe human interaction and agile, robust and adaptive locomotion in complex environments. A soft robot can pass through a hole smaller than its body size using its shape-morphing ability. Passive or active deformation of soft robots enables a safe and gentle physical interaction with a human where their impact on the human is minimal due to their compliant body. This aspect is especially important for medical applications for safe and minimally invasive operation.

Actuation and locomotion methods of current robotic capsule endoscopes are primarily determined by the target gastrointestinal (GI) tract or other human body region in which they will be operated. For close to one-dimensional (1-D) tubular systems such as intestines and esophagus and legs, various type of actuation mechanisms have been proposed using, for example, on-board paddles, micro-motors or off-board magnetic linear or rotational actuation methods. In these approaches, although on-board actuation using micro-motors enables more portable operations, limited power source and limited space on such capsules limit their utility for long duration and less invasive operations.

For three-dimensional (3D) regions of the GI tract such as the stomach, wall-to-wall locomotion methods in a liquid filled environment or a sliding type of surface locomotion method in an inflated stomach have been described using mostly external magnetic actuation methods. In such magnetically actuated capsule endoscopes (MACEs), external magnetic fields are used to exert forces or torques on the internal magnet of the capsule remotely to navigate the capsule in 3D.

Although there have been many promising studies on MACEs and soft robotics, there are still many open issues. First, advanced diagnostic and therapeutic functional modules that are compatible to external magnetic actuation principles are not available yet. Next, precise 3D position control of the device on the tissue surface has not been addressed in detail yet. A robotic manipulator with a permanent magnet is sometimes used for this reason, but the locomotion can be discontinuous and unstable depending on the morphology and friction of the environment. Further, real-time position detection or estimation of MACE that is compatible to continuous magnetic actuation is challenging. To navigate a MACE to a desired position, it is essential to maintain an effective distance between external and internal magnets. Finally, possible tissue damage due to the excessive magnetic attraction (it is difficult to control the magnetic forces on the capsule precisely using external permanent magnet-based actuation) and edges on the capsule could be a safety issue, which has not been addressed in detail in the prior art. All current MACEs are made of rigid outer material, which might create very high stresses on the tissues during magnetic actuation.

To address above issues for the use of MACE's for 3D stomach applications, the present invention describes methods to integrate active capsule endoscopy with soft robotics. Thus, a magnetically actuated soft capsule endoscope (MASCE) is described, which has three novel features with compared to the prior art: 1) Its outside body is made of soft elastomers-based compliant structures. Such compliant structures can deform passively during the robot-tissue contact interactions, which makes the device safer and less invasive. 2) It can be actively deformed in axial direction using external magnetic actuation, which provides an extra degree of freedom that enables various advanced functions such as axial position control, drug releasing, drug injection, or biopsy. We also describe methods that allow the MASCE's shape to be changed from a cylindrical (pill-shape) shape to a spherical-like shape to anchor inside stomach for in situ passive or active drug delivery applications. 3) It navigates in 3D by rolling on the stomach surface which represents a new surface locomotion method inside the stomach. Here, the external attractive magnetic force is used to anchor the robot on a desired location, and the external magnetic torque is used to roll it to another location, which provides a stable, continuous and controllable motion.

SUMMARY OF THE INVENTION

This present invention describes a magnetically actuated soft capsule endoscope (MASCE) to be used as a new medical device for diagnosis and therapeutic applications inside the GI tract or other regions inside the human or animal body. Two embedded internal permanent magnets and a large external magnet or electromagnetic coils are used to actuate the robot remotely. The electromagnetic coils can be those used in an MRI apparatus, Helmholtz coils, Maxwell coils, and any other custom coils designed for a particular purpose. The MASCE of the present invention has three novel features. First, its outside body is made of soft elastomer-based compliant structures. Such compliant structures can deform passively during the robot-tissue contact interactions, which makes the device safer and less invasive. Next, it can be actively deformed in axial direction using external magnetic actuation, which provides an extra degree of freedom that enables various advanced functions such as axial position control, drug releasing, drug injection, or biopsy. Finally, it navigates in 3D by rolling on the stomach surface which represents a new surface locomotion method inside stomach. For this functionality, the external attractive magnetic force is used to anchor the robot on a desired location, and the external magnetic torque is used to roll it to another location, which provides a stable, continuous and controllable motion. In one embodiment of the present invention, shape control capability of MASCE could be used to allow the device to remain in the stomach for an extended time period while in a spherical shape prior to being reshaped through the controllable use of an external magnetic force to a cylinder to allow passage through the intestine. The MASCE of the present invention could be used for a variety of medical applications inside the GI tract including but not limited to drug delivery, biopsy, heat cauterization, pH sensing, biochemical sensing, micro-surgery, and active imaging.

BRIEF DESCRIPTION OF THE DRAWINGS

FIGS. 4A-4D show a schematic of an experimental setup to measure indentation, and experimental results;

FIGS. 13A-C show (a) free-body-diagram of MASCE and EPM for workspace analysis; (b) simulated maximum slope angles that MASCE can ascend using rolling locomotion; and (c) a stomach representation of the workspace of the MASC;

FIG. 35A Assumption: applied force stimulations on the chamber; A: f=0.62 Hz; f=1.25 Hz; FIG. 35B Result: volume change as a function of time due to the applied force; FIG. 35C Concentration of the drug in the chamber;

FIG. 40A Direct exposure to HCl; FIG. 40B Indirect exposure to HCl after coated by hydro-gel polymer; FIG. 40C Indirect exposure to HCl after coated by a silicone-oil. The attached multi-media file shows the response of the cells more clearly;

FIG. 41A is a photo of magnetically actuated soft capsule endoscope (MASCE) prototype, which is localized in 3-D in this study by utilizing its shape deformation and recovery properties. Such localization method enables 3-D mapping of the stomach geometry (FIG. 41B) and the local tissue compliance in addition to precise external magnetic actuation control capability for such capsules (FIG. 41C);

FIG. 43A is the initial state of EPM and MASCE (light shaded arrow: magnetic field from the EPM; dark shaped arrow: magnetization direction of magnets; dotted line: center-to-center line between EPM and MASCE); FIG. 43B illustrates a coaxial alignment stage where the output of the hall-effect sensor inside MASCE is maximized; FIG. 43C illustrates axial shape deformation and FIG. 43D illustrates shape recovery of MASCE by controlling the EPM's coaxial distance are used to measure the axial distance of MASCE from the EPM where the hall-effect sensor output (i.e., internal magnetic field) is suddenly increased or decreased due to the shape change. $D_{dfm}$ and $D_{rcv}$ are the critical distances inducing MASCE's shape deformation and recovery, respectively. $L_{dfm}$ and $L_{rcv}$ are the displacements of EPM in the coaxial direction until shape deformation and recovery occur, respectively;

FIG. 48A is Rolling locomotion; FIG. 48B is θ alignment during the coaxial alignment; FIG. 48C is Φ alignment during the coaxial alignment and shape deformation of MASCE; FIG. 48D is XY alignment; FIG. 48E is Rolling locomotion toward the second goal position; and FIG. 48F is backward rolling locomotion toward the workspace. $C_0$ and $C_1$ represent the actual position of MASCE and $G_1$ and $G_2$ represent its goal positions;

FIG. 49A is a normal process: the first rolling locomotion, 3-D localization (coaxial alignment and shape deformation), XY alignment, steering, and the second rolling locomotion; FIG. 49B is a process on a slope (the boundary of the workspace), the first rolling locomotion, 3-D localization, and backward rolling locomotion;

FIG. 50A is the lower part is the EPM manipulator part, which consists of pivots for Φ and θ rotations for the coaxial alignment stage, and a linear actuator to adjust the distance in the shape deformation and recovery stage; and FIG. 50B is the upper part with five degree-of-freedom motion stage and a webcam for image analysis. $T_{abs}^{rel}$ is calculated based on the substrate's offset distances ($x_{off}$, $y_{off}$, $z_{off}$) in three axis ($X_{abs}$ $Y_{abs}$ $Z_{abs}$) and offset orientations ($\Phi_{off}$, $\theta_{off}$) about two axis ($\Phi_s$, $\theta_s$);

FIG. 51B are Shape recovery ($D_{rcv}$)-based localizations;

FIGS. 54A-B are Deformation-compensated 3-D maps of the synthetic stomach model (the local surface), where FIG. 54A is an overview of the matching results; and FIG. 54B is a side view of the contact points and the reconstructed 3-D geometrical model. The black mesh is the real stomach geometry. The surface with gradient is the reconstructed stomach geometry. The arrows point to linkages (green) that indicate the deformation-compensated contact point;

DETAILED DESCRIPTION OF THE INVENTION

The present invention will describe a system and a method to control and operate a capsule endoscopic robot within an organ of a patient, as well as a compliant capsule endoscopic robot. A non-compliant or rigid capsule endoscopic robot is also within the scope of the invention notwithstanding the lack of a detailed disclosure and accompanying figures. The non-compliant or rigid capsule endoscopic robot may include all the components integrated into the compliant capsule endoscopic robot except that the capsule will not collapse or deform (e.g. side linkages do not flex or bend) when a magnetic force is applied to dispense, for example, a dose of a drug contained within the drug chamber described in detail below.

The present invention described herein is a swallowable device with a soft, compliant exterior, whose shape can be changed through the use of magnetic fields, and which can be locomoted in a rolling motion through magnetic control from the exterior of the patient. The MASCE of the present invention could be used for a variety of medical applications inside the GI tract including but not limited to drug delivery, biopsy, heat cauterization, pH sensing, biochemical sensing, micro-surgery, and active imaging.

Figure 1A:
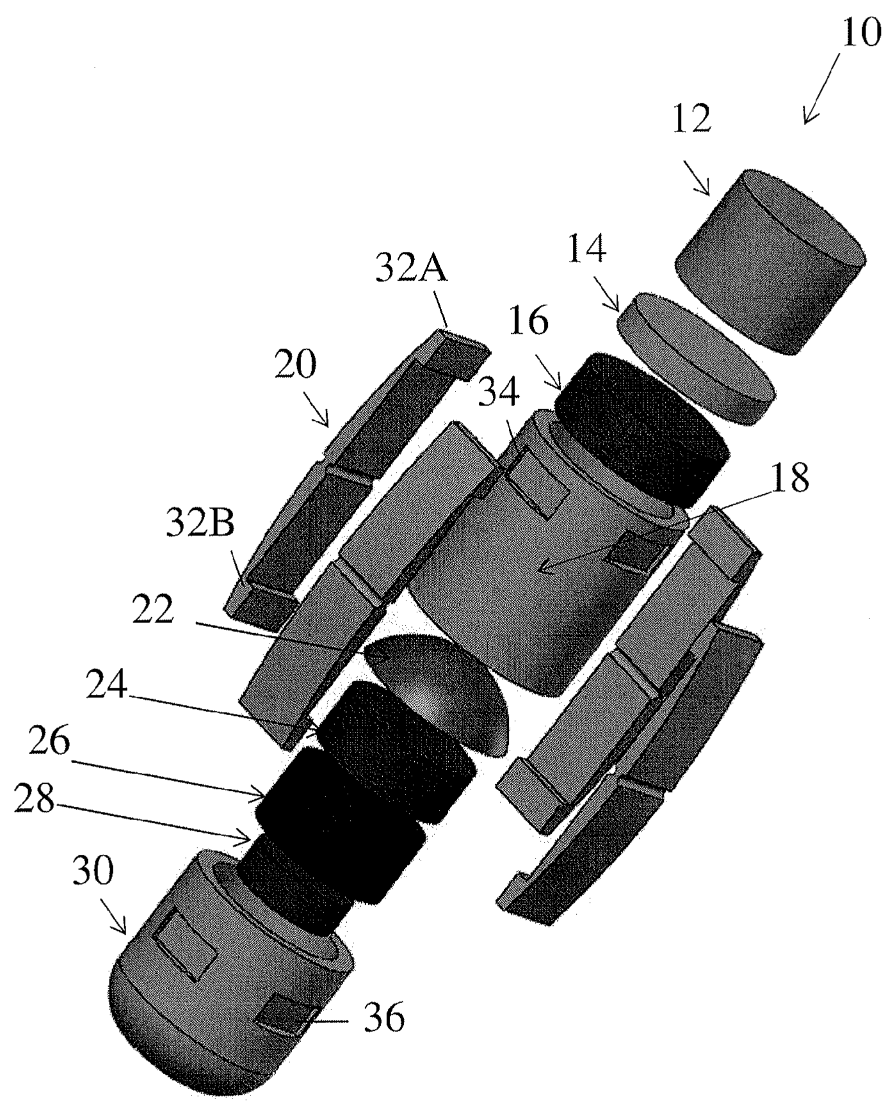
FIGS. 1A-D show pictorials of the components of one exemplary embodiment of the compliant capsule endoscopic robot.
Figure 1B:
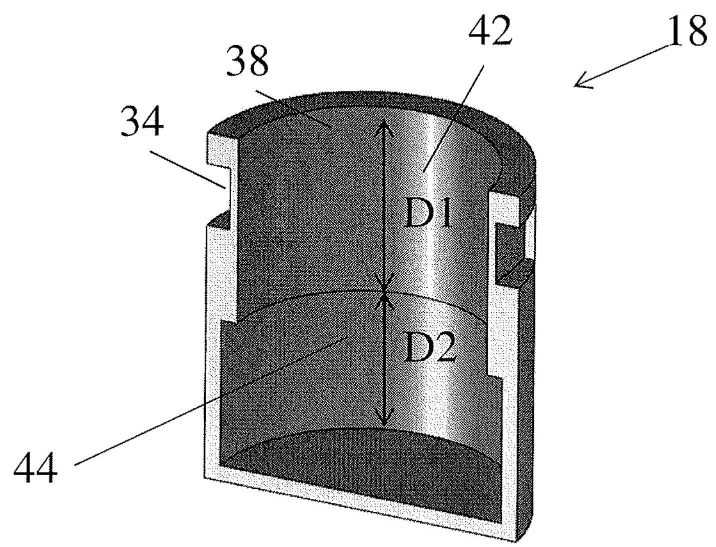
Figure 1C:
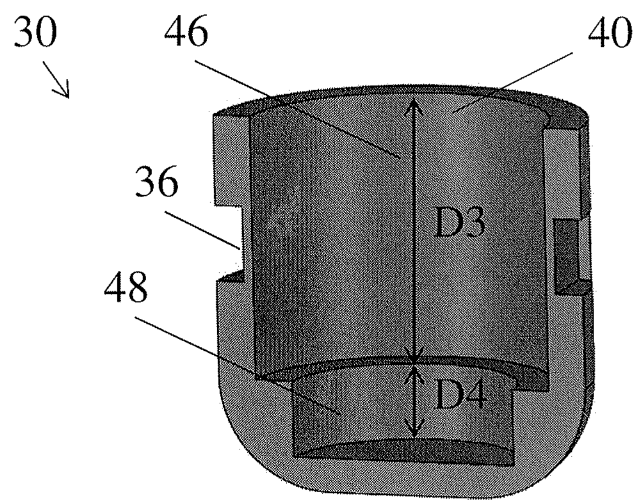

FIGS. 1A-D show the schematic of the components of one exemplary embodiment of the MASCE 10 of the present invention. FIG. 1A illustrates an exploded view of MASCE 10 including an upper head 18 that is sized to receive the camera module 12 through upper head opened end 38 (FIGS. 1B and 1D) and seat within upper head first interior bore diameter 42. In the case where the larger diameter interior bore (e.g. upper head second interior bore diameter 44) is adjacent a small diameter bore (e.g., upper head first interior bore diameter 42, which is adjacent the only opening (e.g., upper head opened end 38), then the head (e.g., upper head 18) can either be manufactured in two pieces (a half similarly to the one shown in FIG. 1B) or include an open bottom (not shown) for insertion of the component (e.g., coin battery 14, upper permanent magnet 16) into the space defined by a depth (e.g., D2) and an interior diameter (e.g., upper head second interior bore diameter). The halves are joined together or bottom attached to the main body of the head after insertion of the component into the space. Alternatively, the head can be one single, integrally made component as illustrated by lower head 30 that is sized to receive through lower head opened end 40 (FIGS. 1C and 1D) and seat within lower head first interior bore diameter 46 and lower head second interior bore diameter 48 the following components: lower permanent magnet 24, electronics and sensors 26, and transceiver or antenna 28. However, other embodiments of lower head 30 can be made as separate parts that are joined together be conventional methods. Drug chamber 22 can be attached to lower head 30 adjacent to lower head opened end 40.

Depths D1, D2, D3, and D4 of the upper head first interior bore diameter 42, upper head second interior bore diameter 44, lower head first interior bore diameter 46, and lower head second interior bore diameter 48, respectively, can be any suitable dimension to retain the desired component therein. Though the diameters of the internal bores are shown as one being larger than another, the invention is not to be limited by any illustrated relationship that can be any suitable dimension to retain the desired component therein.

Figure 1D:
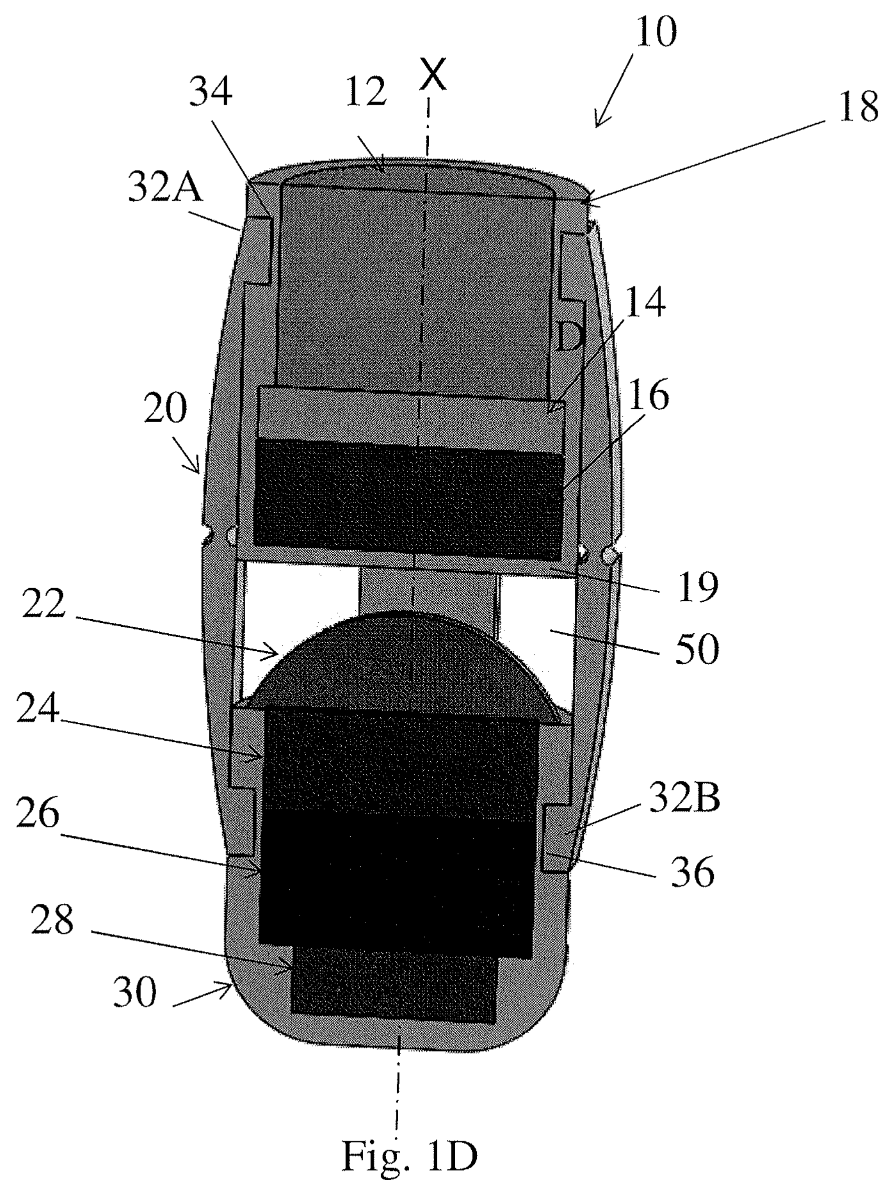

Upper head 18 and lower head 30 are assembled in an orientation having drug chamber 22 opposing bottom surface 19 of upper head 18 with gap 50 (FIG. 1D) there between when MASCE 10 is in its relaxed or extended form as shown in FIG. 1D. Contoured ends 32A, 32B of side linkages 20 are received into upper head contoured recess 34 and lower head contoured recess 36. Contoured ends 32A, 32B can be retained within recesses 34, 36 by any conventional method such as interference fit (contoured ends 32A, 32B are larger than recesses 34, 36), adhesives, and other mechanical attachments (e.g., nuts/bolts, screws). Four side linkages 20 are shown but the invention is not to be limited to any specific number of side linkages 20 with as few as two side linkages 20 necessary for an aligned longitudinal traversal of upper head 18 and/or lower head 30 along axis X. Once assembled, drug chamber 22 is in opposing orientation to bottom surface 19 of upper head 18 such that when bottom surface 19 contacts and compresses or contracts resilient drug chamber 22 as side linkages 20 blend or flex (discussed further below) as permanent magnets 16 and 24 are drawn toward each other due to a mutual magnetic attraction and/or an external force, a predetermined dosage of a drug contained within resilient drug chamber 22 is released. Alternatively, drug chamber 22 can be a solid structure either entirely made of a drug or coated with a drug formulated for a continuous or timed release of a predetermined dosage of the drug.

Figure 1E:
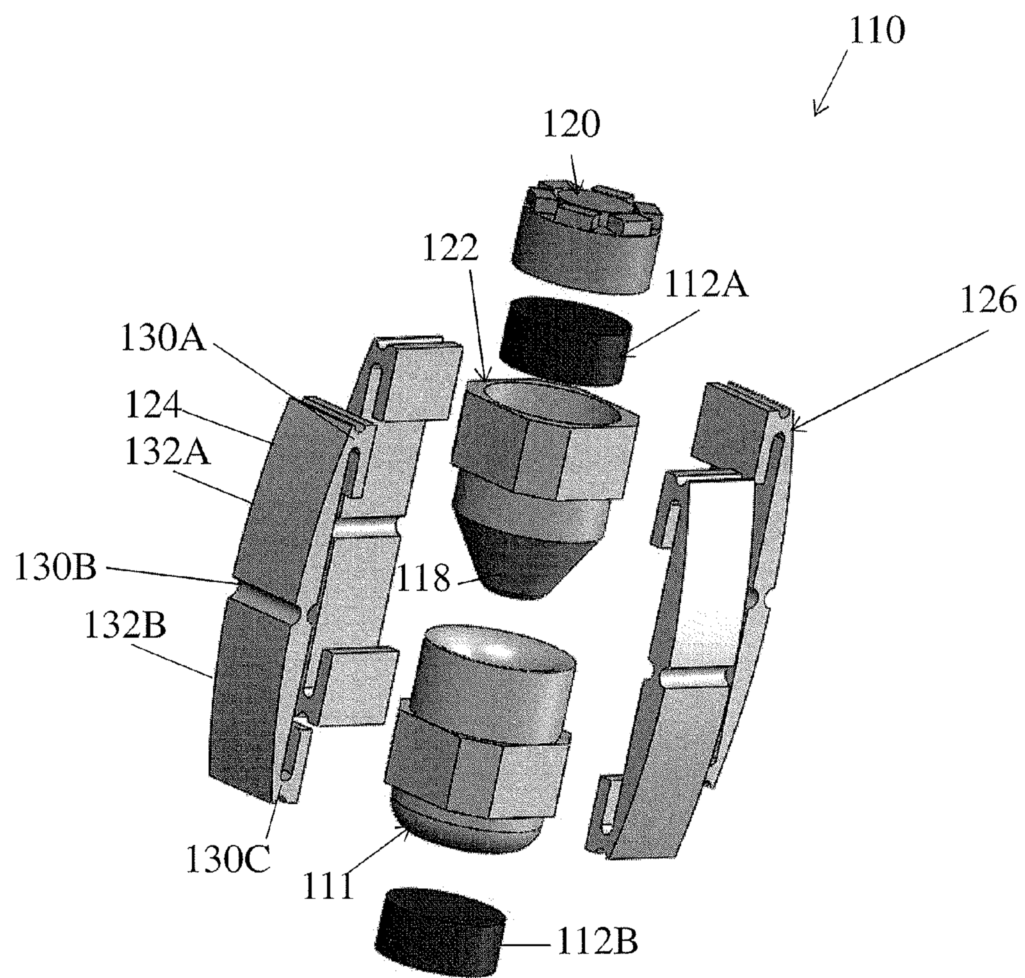
FIGS. 1E-I show pictorials of the components of another exemplary embodiment of the compliant capsule endoscopic robot.
Figure 1F:
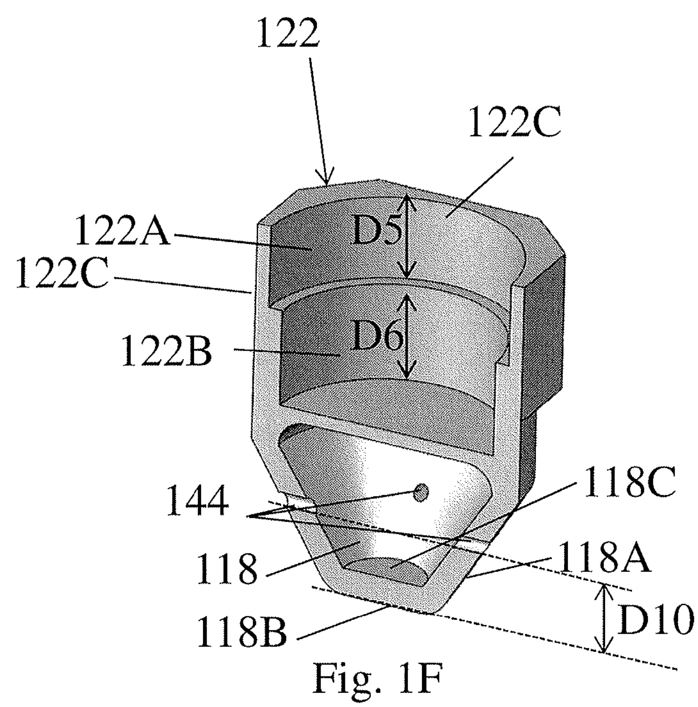
Figure 1G:
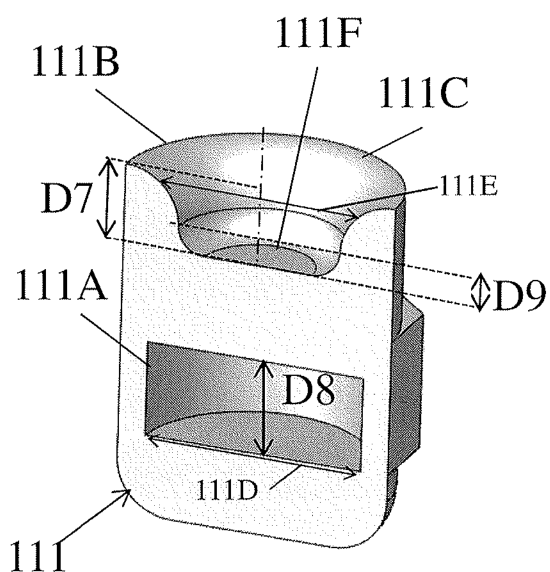

FIGS. 1E-I show the schematic of the components of another exemplary embodiment of the MASCE 110 of the present invention. FIG. 1E illustrates an exploded view of MASCE 110 including an upper head 122 that is sized to receive the camera module 120 and internal permanent magnet 112 through upper head opened end 122C (FIGS. 1F and 1G) and seat within upper head first interior bore diameter 122A and upper head first interior bore diameter 122B, respectively. Drug Chamber 118 is shown integral with upper head 122 and having drug release holes 144. The drug chamber 118 can be made of a pliable, resilient matter that will compress or deform when it contacts recess 111B of lower head 111, and thereby release the predetermined dosage of drug through holes 144. Upper head 122 can be made on a single, integral piece or multiple pieces and joined together as discussed above.

Lower head 111 includes an open end 111C, drug chamber recess 111B, and a permanent magnet chamber 111A. In the case where the permanent magnet chamber 111A is not readily accessible from the outside to install permanent magnet 112, then lower head 111 can either be manufactured in two pieces (a half similarly to the one shown in FIG. 1G) or include an open bottom (not shown) for insertion of the component (e.g., internal permanent magnet 112) into the space defined by a depth (e.g., D8) and an interior diameter 111D. The halves are joined together or bottom attached to the main body of lower head 111 after insertion of internal permanent magnet 112 into the space.

Depths D5, D6, D7, and D8 of the upper head first interior bore diameter 122A, upper head second interior bore diameter 122B, recess 111, and lower head permanent magnet chamber 111A, respectively, can be any suitable dimension to retain the desired component therein. Though the diameters of the internal bores 122A, 122B, recess 111B, and chamber 111D, are shown as one being larger than another, the invention is not to be limited by any illustrated relationship that can be any suitable dimension to retain the desired component therein. The various interior diameters 111E of recess 111B are contoured to cooperate with the outer diameters 118A of drug chamber 118 to compress or deform drug chamber 118 to release the drug contained within drug chamber 118. One embodiment of recess 111B has a bell shaped configuration allowing the drug released from drug chamber 118 to flow or disburse unobstructed from drug chamber 118, whereas Depth D10 of drug chamber 118 from bottom edge of drug release holes 144 to base 118B is greater than depth D9, which represents the transition point of the bell shaped curve.

Figures 1H, 1I:
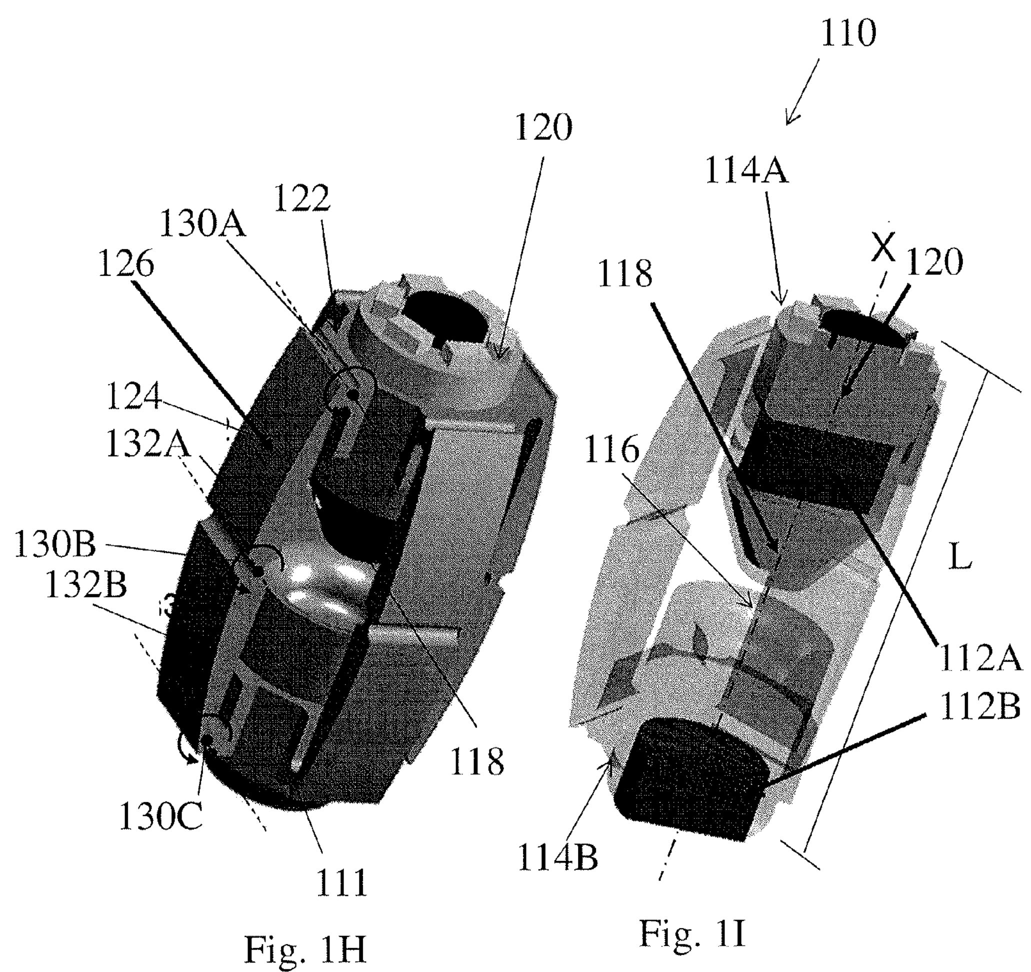

Upper head 122 and lower head 111 are assembled in an orientation having drug chamber 118 of upper head 122 opposing recess 111B of lower head 111 with gap 116 (FIG. 1I) there between when MASCE 10 is in its relaxed or extended form as shown in FIG. 1H. Hinge ends 130A, 130C of side linkages 126 are fixedly attached to upper head 122 and lower head 111, respectively, by any conventional attachment means including but not limited to adhesives, nuts/bolts, screws, or combination thereof. Four side linkages 126 are shown but the invention is not to be limited to any specific number of side linkages 126 with as few as two side linkages 126 necessary for an aligned longitudinal traversal of upper head 122 and/or lower head 111 along axis X. Once assembled, drug chamber 118 is in opposing orientation to recess 111B of lower head 111 such that when base 118B contacts recess 111B, resilient drug chamber 118 compresses or contracts as side linkages 126 blend or flex (discussed further below) as permanent magnets 112A, 112B are drawn toward each other due to a mutual magnetic attraction and/or an external force, a predetermined dosage of a drug contained within resilient drug chamber 118 is released. Alternatively, a syringe or plunger-type mechanism (not shown) can be integrated into drug chamber 118 such that the syringe or plunger resting at the bottom 118C of drug chamber 118 advances upward forcing the drug upward to holes 144 when a shaft end extending outwardly from base 118B contacts base 111F of recess 111B. Alternatively, drug chamber 118 can be a solid structure either entirely made of a drug or coated with a drug formulated for a continuous or timed release of a predetermined dosage of the drug.

The following examples will utilize the embodiment of the MASCE disclosed in FIGS. 1E-I that show the schematic of the components of an alternative embodiment of the MASCE 110 of the present invention. However, the MASCE 10 disclosed in FIGS. 1A-D could also to used, and therefore, the disclosed results for MASCE 110 is applicable to MASCE 10.

Now returning to FIGS. 1E-I and MASCE 110 of the present invention having two internal permanent magnets 112A, 112B are embedded inside both ends 114A, 114B to allow magnetic actuation and shape deformation. The space 16 between two internal magnets 112A, 112B are used for a diagnostic or therapeutic function. For example, in one embodiment, an encapsulated liquid drug chamber 118 can be located here for controlled drug releasing. In one embodiment, a camera module 120 is implanted in the upper head 122 of on end 114 of MASCE 110.

Figure 2A:
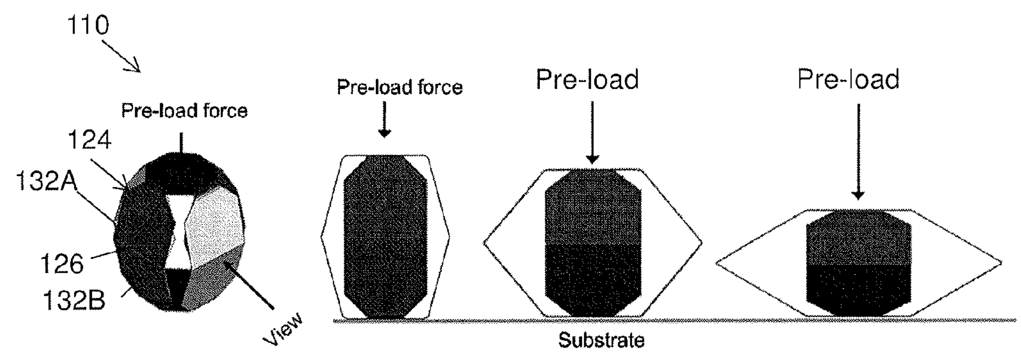
FIGS. 2A-E show schematics of deformation mechanism design features of the present invention.
Figures 2B, 2C, 2D, 2E:
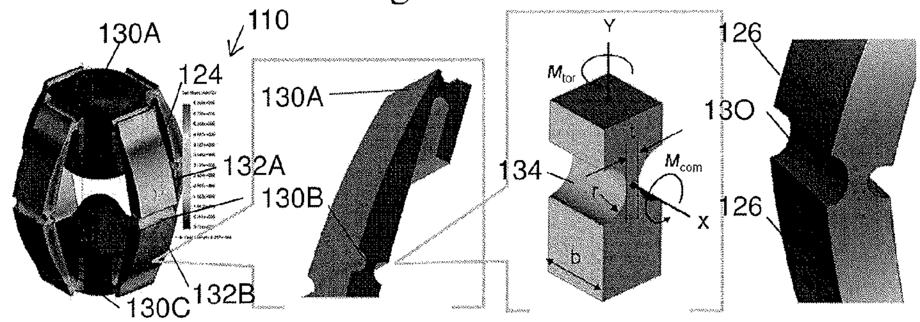
Figure 3A:
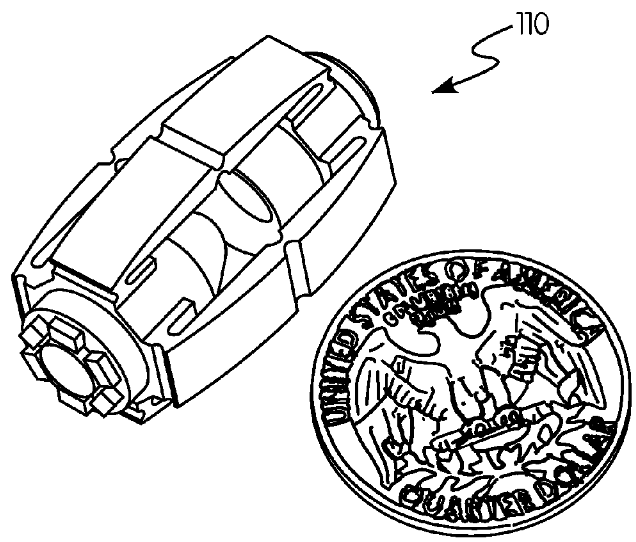
FIGS. 3A-C show photographs of a prototype of the present invention.
Figure 3B:
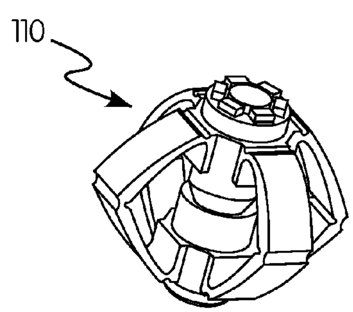
Figure 3C:
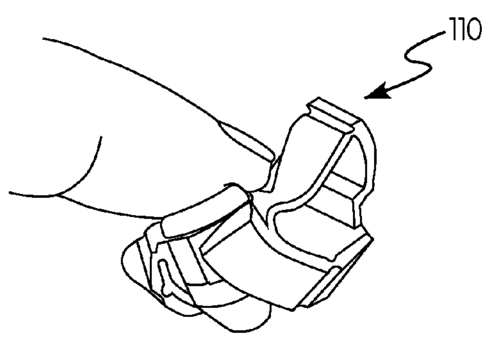

MASCE 110 has three main design features allowing magnetically actuated shape deformation and recovery:

i) Sarrus Linkage:

The outer compliant structure 124 of MASCE 110 is based on a Sarrus linkage. The deformation mechanism is shown in FIG. 2A. With axial compression pre-load at one end 114A, 114B, the side linkages fold and the outer compliant structure 124 becomes fully compressed against a substrate 128 (which can represent tissue) opposing the pre-load force. A finite elements analysis of this mechanism is shown in FIG. 2B. The bright areas mean areas folded by a compressive force and play the role of hinges 130A, 130B, 130C (See FIGS. 1E-F). This simple mechanism is appropriate for MASCE 110 because its initial shape is similar to a typical capsule and its deformation amount can be controlled by the external magnetic field gradient in the axial direction. As the safety performance parameter, maximum compressive stress of the MASCE 110 on the tissue surface should be minimized much below the pain level, which is 5 kPa. The shape of the fully compressed MASCE 110 with deployed side linkages 126 is close to a sphere with a contact area that increases from 78.5 $mm^2$ to 320 $mm^2$, which reduces the stress on the tissue around 4 times with compared to its non-deformed shape.

ii) Circular Flexure Hinge:

MASCE 110 has to recover its initial shape if the compressive preload force due to the external magnetic field is removed. For the passive shape recovery process, the folded areas of side linkages 126 of MASCE 110 were designed as flexure hinges 130 A-C. As shown in FIG. 2B, each side linkage 126 has five flexible geometries; three circular flexure hinges 130A-C and two flexible beams 132A-B. Among these, the circular flexure joint in the middle hinge 130B is a dominant factor determining the overall compliance because the compressive and tensile stresses are concentrated on this region. The design variables of the flexure joint 134 are shown in FIG. 2D. The joint 132 is bent by the moment $M_{com}$ about the x-axis. Among various models explaining the circular flexure joint 134, assuming that the ratio between hinge thickness (t) and the radius of circle (r) is almost 1, the rotational compliance of the flexure joint $c_\alpha$ is expressed as $$c_\alpha = \frac{\alpha_x}{M_{com}} = \frac{12(1.13t/r + 0.332)r}{Ebt^3} \quad (1)$$

where $M_{com}$ is the applied moment about the x-axis, $\alpha_x$ is the rotational angle about the x-axis, r is the radius of circle, t is the thickness of the hinge, and b is the width of the hinge, and E is Young's modulus of the material. The calculated rotational compliance is 4.70 $N^{-1}\cdot mm^{-1}$ using the actual values of these design variables in FIG. 2(*d*), which are 700 μm radius, 600 μm thickness, 6 mm width, and 3 MPa modulus. When the flexure hinge with this level of compliance is bended by 3.6 N·mm of torque, the rotational angle $\alpha_x$ is about 138 degree. This estimation matches well with the experimental data at 125 degree, which can be observed in FIG. 3B. 3.6 N·mm of torque is calculated based on 600 mN maximum preload force in FIG. 4D and 6 mm of rotating radius. FIG. 3A illustrates the extended size of one embodiment of MASCE 110 compared to quarter.

iii) Outer Body Compliance:

The outer compliant structure 124 should passively recover its original shape after any shape change due to the tissue-surface interactions or external actuation, similar to the exaggerated manual compression in FIG. 3C. This compliance property also prevents any possible tissue damage during swallowing and/or the peristaltic movement. To enable such shape recovery, the axial compliance and the internal magnetic attraction at the maximum compressed state should be designed accordingly. The quantitative design conditions of such shape recovery are explained below.

Compliance Characterization

To characterize the compliance of the designed MASCE 110, a prototype was fabricated and tested. All the parts are manufactured by molding 3D printed parts by a soft polyurethane elastomer (e.g. ST-1060, BJB Enterprise Inc. with 2.07 MPa Young's modulus). The fabrication process is as follows. First, master parts are made using a rapid prototyping machine (e.g. Invision HR, 3D System), and the side linkage parts 126 are manufactured using a micro-wire electrical discharge machine (e.g. AP 200L, Sodick) due to their complex geometry. Then, flexible molds are made by casting the master parts by silicone rubber (e.g. Dow Corning, HS II). After the flexible molds are cured, internal magnets 112A, 112B are placed in the cavities of the mold. Next, polyurethane is poured onto the mold with magnets 112A, 112B. After the polyurethane is cured in room temperature (in one embodiment, for 24 hours), all parts are peeled separately. Later, all parts are assembled together using the same polyurethane (e.g. ST-1060) as a bonding layer. Thus, except for electronics and magnets 112A, 112B, the whole body is made of polyurethane elastomer.

Finally, the camera module 120 is inserted in the upper head 122 (not shown in FIGS. 2A-E).

TABLE I

| SPECIFICATIONS OF THE MASCE PROTOTYPE | |
|---|---|
| Diameter of Capsule Head | 15 mm |
| Maximum/Minimum Length | 40 mm/3 mm |
| Weight | 8.6 g |
| Internal Magnets: Size (cylindrical) | Diameter: 10 mm, Length: 6 mm |
| Material | NdFeB |
| Radius of Deployed Side Linkages | 20 mm |

The axial compliance behavior of the MASCE prototype 136, specified in Table I, is characterized by an indentation (compression) setup illustrated in FIG. 4A. The resistive force ($F_{res}$) of the capsule 138 and the compressed length ($\Delta L$) are measured while the capsule 138 is indented (compressed) vertically. The resistive force is the sum of the restoring force of the side linkages 126 and the attractive force between the internal magnets 112. If the former is stronger than the latter, the resistive force measured by the load cell is positive, otherwise negative.

In FIG. 4B, the gray line shows the experimentally measured resistive forces for a given compressed length. First, the resistive force increases as the capsule 126 is compressed because the restoring force of the deformed side linkages induces most of the resistive force. However, the resistive force decreases from a certain level of compressed length as the gradient of the magnetic attraction becomes stronger than that of the restoring force. The hysteresis starts at this point, $P_b$. Assuming that as the external permanent magnet 140 approaches MASCE prototype 136 as in FIG. 4C, the capsule 136 is deformed according to the equilibrium between the magnetic attraction, $F_{mag}$, and $F_{res}$. If the magnetic attraction becomes stronger than, for example, 310 mN for this prototype, the capsule 38 becomes compressed more because the $F_{mag}$ is stronger than $F_{res}$. However, the difference between the $F_{mag}$ and $F_{res}$ becomes larger as the capsule is compressed. Therefore, at this 310 mN, the capsule's compression is abruptly accelerated and two magnets snap into contact (full compression state). While $P_b$ is a critical point in the compressing motion, $P_d$ is the one during the relaxation process. The capsule length is not increased even though the applied magnetic attraction is decreased. However, when the pre-load falls below 160 mN, the capsule 138 recovers its initial length after $P_d$.

Conditions for Shape Deformation and Recovery

Figure 4D:
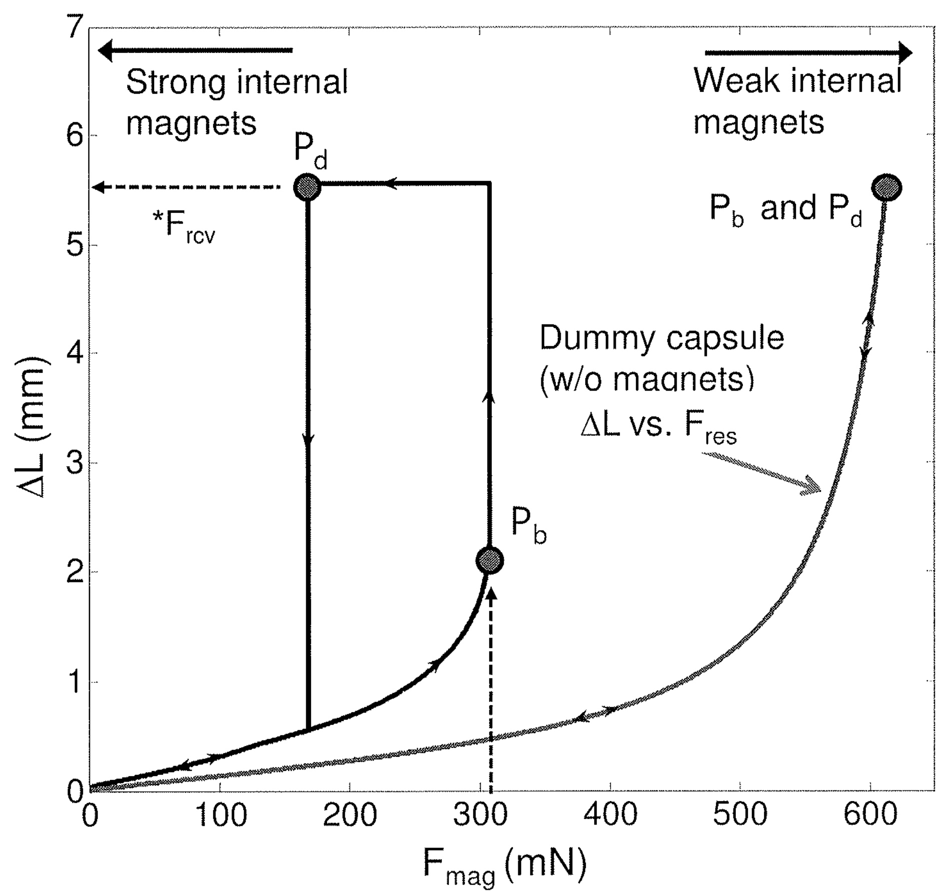

The above deformation curve is used to select the optimal size of the internal magnets 112A, 112B. FIG. 4D shows the change in the deformation curve due to the internal magnet 112A, 112B. As internal magnets 112A, 112B become smaller, the overall deformation curve converges to the deformation curve of a dummy capsule with no magnets inside and the hysteresis behavior is lost. In this case, the controllable deformation range is expanded, but stronger magnetic attraction is required to trigger the full compression of the capsule 136. In contrast, if stronger internal magnets 112A, 112B are implanted, the overall deformation curve moves to the left and a large hysteresis loop is created. At the extreme case, if the critical point of the relaxation process, $P_d$, crosses over the y-axis, $*F_{rcv}$ in FIG. 4D becomes negative, and the capsule's original shape cannot be recovered. Therefore, the force margin for the shape recovery, $*F_{rcv}$, is very important in the capsule's axial compliance design. The fact that the $*F_{rcv}$ is a negative value means that the internal magnets are stuck each other without the external magnetic attraction and it cannot recover its initial shape. To quantify the necessary conditions for the reversible shape deformation and recovery process, below conditions should be held:

$$F_{res}(\Delta L, B_{int}+B_{ext})=F_{rst}^{srs}(\Delta L)+F_{mag}(\Delta L, B_{int}+B_{ext})\leq 0 \quad (2)$$

$$0<F_{res}(\Delta L_{max}, B_{int})=F_{rst}^{srs}(\Delta L_{mas})+F_{mag}(\Delta L_{mas}, B_{int}) \quad (3)$$

where the resistive force of the capsule is $F_{res}(\Delta L, B)$, the compressed length of the capsule is $\Delta L$, the applied magnetic field is B, the attraction force between internal magnets is $F_{mag}(\Delta L, B)$, the restoring force of Sarrus linkages is $F_{rst}^{srs}(\Delta L)$, and the magnetic field applied to the upper internal magnet by the other internal magnet and the external permanent magnet are $B_{int}$ and $B_{ext}$, respectively. Equation (2) represents a condition for shape deformation, which can be satisfied if the external magnetic field, $B_{ext}$, is simply strong. In contrast, Equation (3) means a condition for shape recovery after removing the external magnetic field. $*F_{rcv}$ is different expression of $F_{res}(\Delta L_{max}\ B_{int})$.

Compression Length Estimation

Figure 6:
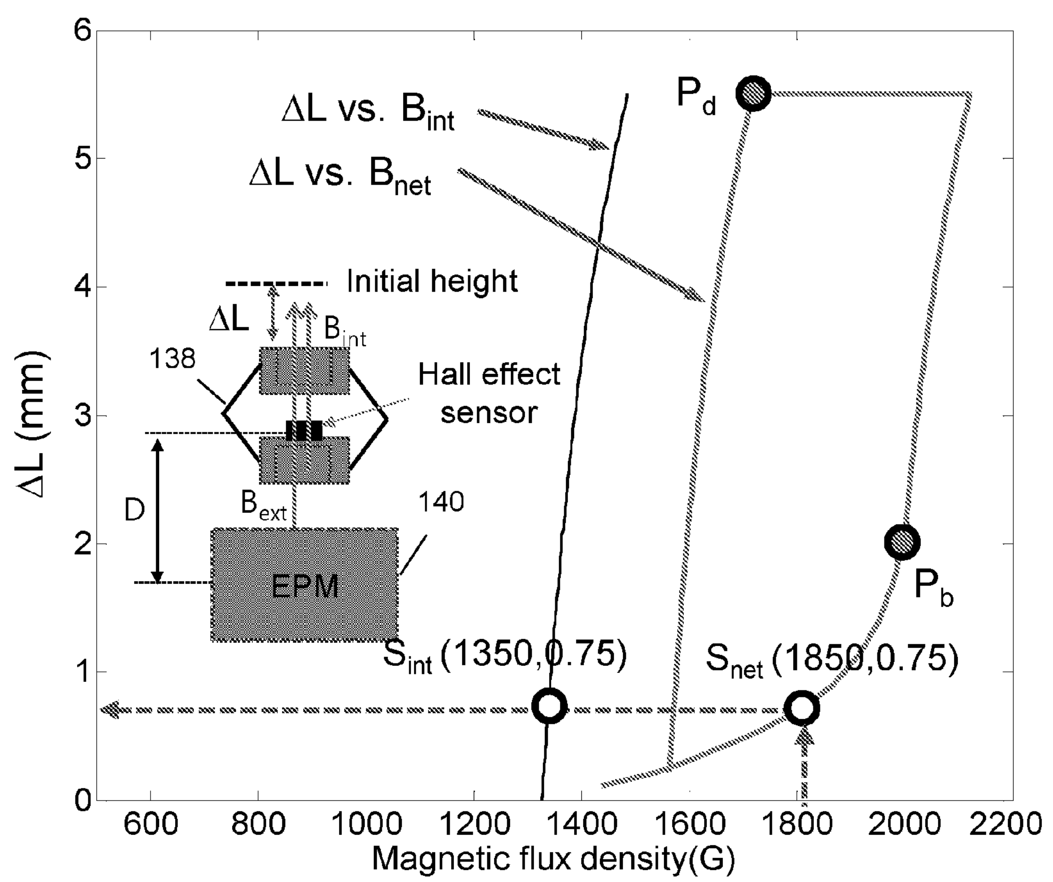
FIG. 6 shows data on the relationship between magnetic flux density and the compressed length of a prototype of the present invention.
Figures 7A, 7B, 7C, 7D, 7E:
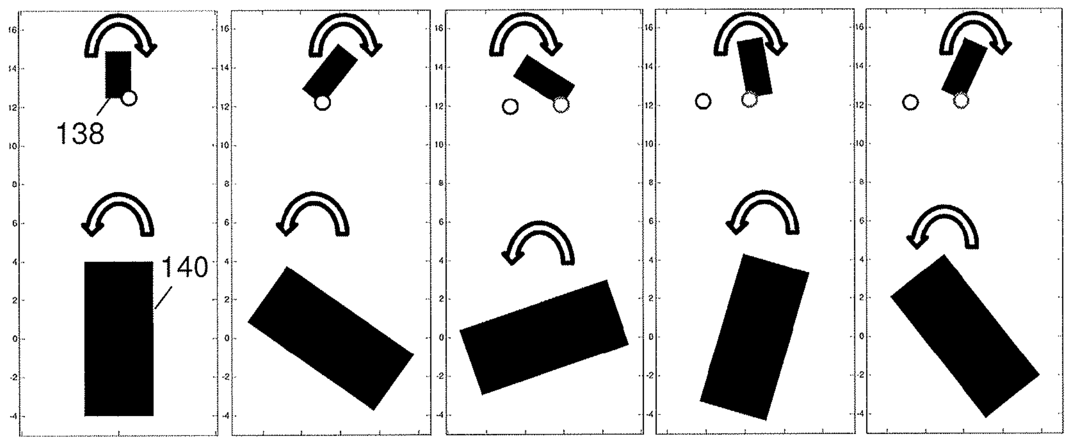
FIGS. 7A-E show schematics of the rolling locomotion capability of capsule of the present invention.

The capsule 138 is deformed by the magnetic field in its axial direction. Therefore, its axial compression can be estimated using the magnetic flux density measured by a hall-effect sensor as shown in FIG. 6. In the case of the first generation prototype, the on-board hall-effect sensor cannot cover the whole range of magnetic field values during the shape deformation process because of the short distance between the sensor and the internal magnet. Therefore, here, the compressed length curve is predicted by dividing the magnetic field into two parts: the internal magnetic field and the external permanent magnet 140. FIG. 6 shows two curves. First, the left curve (black) is an experimental data about the magnetic field ($B_{int}$) contributed by the internal magnets according to the compressed length (ΔL). Next, using the shape deformation curve of FIG. 4B and the magnetic charge model, the external magnetic field, which is required at each compressed length, is calculated. The right (gray) curve is the net magnetic field ($B_{net}$), the sum of internal magnetic field and the external permanent magnet 140. The compressed length of the capsule 138 can be estimated using ΔL vs. $B_{net}$ curve. For example, if 1850 G of magnetic flux density is measured on the sensor, the estimated location in the plot is point S and ΔL is estimated as 0.75 mm. Another important use of this curve is to predict the external magnetic field ($B_{ext}$) at each point, which is the difference between $B_{net}$ and $B_{int}$ at the same compressed length. This estimated external magnetic field information could be used to compute the distance between the capsule 138 and the external permanent magnet 140 using the magnetic field models such as the dipole model or the charge model. For example, for the 1850 G of magnetic flux density and 0.75 mm of ΔL, $B_{ext}$ is computed as 520 G, which gives 97 mm of vertical distance between the capsule 138 and the external permanent magnet 140. In summary, estimation of the capsule's position and axial deformation is possible by using an on-board hall-effect sensor and magnetic field models of the system.

Magnetic Actuation

A magnetic actuation system is described for the rolling based surface locomotion of MASCE 110. Such a locomotion method has two major advantages. First, the locomotion is more stable and controllable. Dragging the capsule along a stomach wall using magnetic attraction can induce unstable, discontinuous and uncontrollable locomotion behavior due to complex surface morphology and irregular friction properties of the stomach tissue. However, rolling locomotion can allow a smooth and continuous locomotion and stable steering because the capsule is always anchored to the tissue surface during the locomotion due to the external permanent magnet's (EPM's) magnetic attraction. Next, surface locomotion allows the improved tissue surface diagnosis and tissue targeting capability for therapeutic procedures. Considering that selective monitoring and treatment on the target tissue are key expectations from active capsule endoscopes, this locomotion behavior can be more effective than dragging locomotion and three-dimensional linear pulling movement using EPM's magnetic field gradients.

The rolling locomotion technique of the present invention also provides an omni-directional and more complete view of 3D stomach tissue wall to the operator while the current camera modules have limited angles of sight (<120 degrees) and resolution (320×320 pixels), which could miss some tissue areas of the stomach wall.

Magnetic Actuation Platform Overview

Figures 5A, 5B:
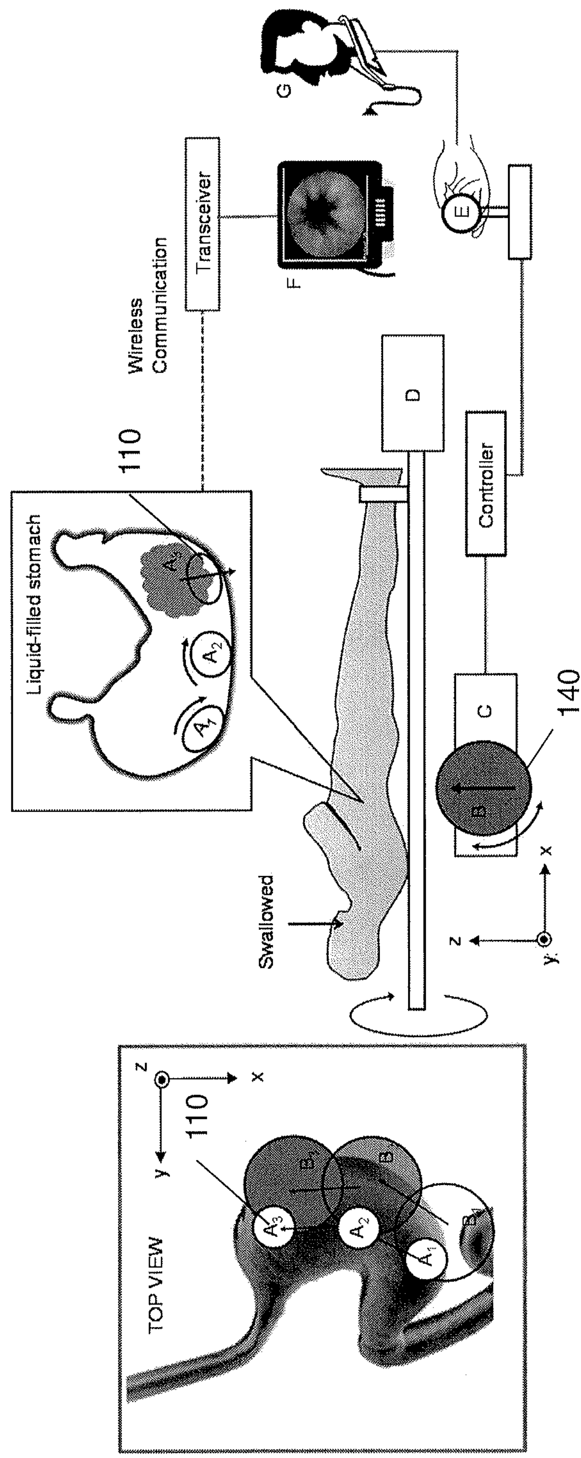
FIGS. 5A-B show a schematic of an application scenario for the use and control of the present invention.

As shown in FIGS. 5A-B, in one embodiment of the present invention, the actuation platform of MASCE 110 can consist of or be adapted to a rotatable or stationary patient bed 142 and a motorized external permanent magnet 140 (EPM). The rotatable patient bad can have 3-degrees of freedom. One embodiment of the system of system to magnetically actuate a compliant capsule endoscopic robot for diagnosis and treatment: A: capsule endoscopic robot A1-A2: rolling locomotion; A3: biopsy or drug releasing; B: Spherical EPM (External Permanent Magnet); C: Motorized XYZ-θΦ stage (see FIG. 43A) linear actuator x-y-z planes, electronic magnet head pivot Φ and rotational θ, plus rotational actuator about y-radius); D: Bed for a patient; E: Joystick; F: Images and HMI (Human Machine Interface); G: Clinician. The rolling based MASCE locomotion method covers a given limited 3D working space inside the stomach in a specific patient orientation. By this setting, 3D locomotion of the MASCE 110 is simplified to surface locomotion, which makes it more controllable. Also, due to the stomach weight in the initial state, positions of the environmental organs can be stabilized and unexpected organ arrangement due to magnetic attraction can be minimized. Please note that the external permanent magnet can be replaced by electromagnetic coils can be those used in an MRI apparatus, Helmholtz coils, Maxwell coils, and any other custom coils designed for a particular purpose. Though external permanent magnet B is shown below the patient bed, external permanent magnet B can be oriented in any position around the bed as it is rotated about circular y-radius.

To cover the entire stomach wall or reach to any random 3D location on the stomach tissue, the patient bed's 142 orientation is changed after the MASCE 110 explores a given workspace at any orientation. Moving patient bed 142 can minimize the required workspace of the EPM manipulator, thus making the actuation platform smaller. The external magnetic torque created by rotating the EPM 140 induces the MASCE's 110 rolling behavior. Also, controlled magnetic gradient exerted by the EPM 140 is used to create an attractive magnetic force on the MASCE 110 to anchor it to a specific location on the stomach tissue.

Working Principle of Surface Locomotion

The surface locomotion method using rolling motion of the present invention is based on the symmetrical orientation between the MASCE 110 and the EPM 140, which means that the capsule's rotation angle is symmetrical to the EPM's angle to the substrate (e.g., tissue) where the capsule is anchored. FIGS. 7A-E show the simulated locomotion behavior of rolling locomotion. By the rotation of the EPM 140, the external magnetic field is also rotated and MASCE 110 rolls while being anchored to the tissue surface. More detailed description about the tissue contact interactions is introduced in the next section.

In this section, the basic principle of symmetrical orientation is described.

Magnetic force and torque can be calculated by a series of steps as below. According to the magnetic charge model, the magnetic field at a point P(x,y,z) can be calculated by integrating all the minute magnetic field elements from surface area elements of the EPM 140. This relation can be expressed as $$B(P)=\begin{bmatrix}B_x\\B_y\\B_z\end{bmatrix}=\oint_N \frac{B_r r}{4\pi|r|^3}dN-\oint_S \frac{B_r r}{4\pi|r|^3}dS \tag{4}$$

where $B_r$ is the residual magnetic flux density, dN and dS are surface area elements of the north pole and the south pole of the EPM 140, and r is the vector from the surface element to point P(x,y,z).

When the MASCE 110 is located within a magnetic field, it experiences magnetic force and alignment torque. First, the force on the MASCE 110 can be calculated as $F(P)=[F_x\ F_y\ F_z]^T=$v (M·∇B) where v is the volume of the internal magnets 112A, 112B of the MASCE 110, M those magnetization vectors, and B the magnetic field induced by the EPM 140. If there is no electric current flowing through the occupied region, this relation can be simplified as $$F(P) = v\left[\frac{\partial B}{\partial x} \quad \frac{\partial B}{\partial y} \quad \frac{\partial B}{\partial z}\right]M \tag{5}$$

Next, the magnetic torque T is generated when the MASCE's 110 magnetization direction is misaligned with the external magnetic field. In 3D, torques about the x-axis, y-axis and z-axis can be obtained by $T=[T_x\ T_y\ T_z]^T=vM\times B$.

Figure 8:
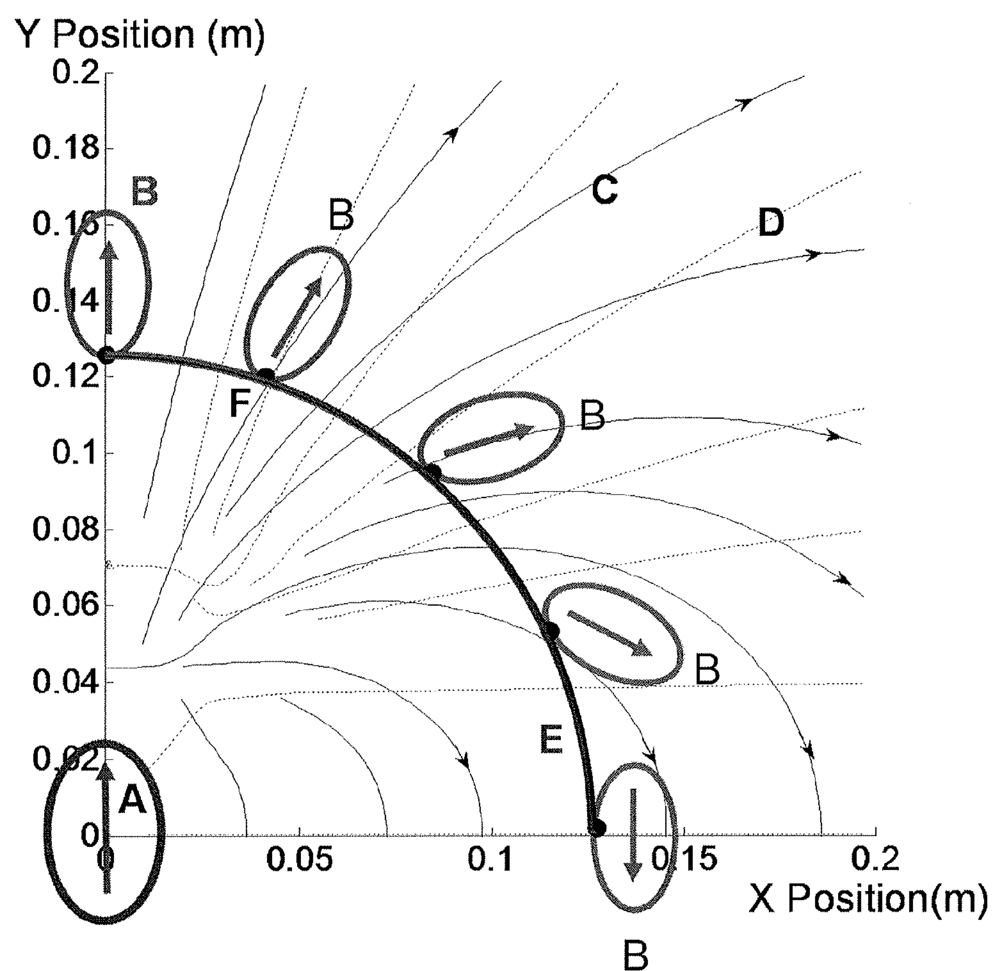
FIG. 8 shows simulated magnetic field (flux density) and the magnetic attractive force in two-dimensional space.
Figure 9:
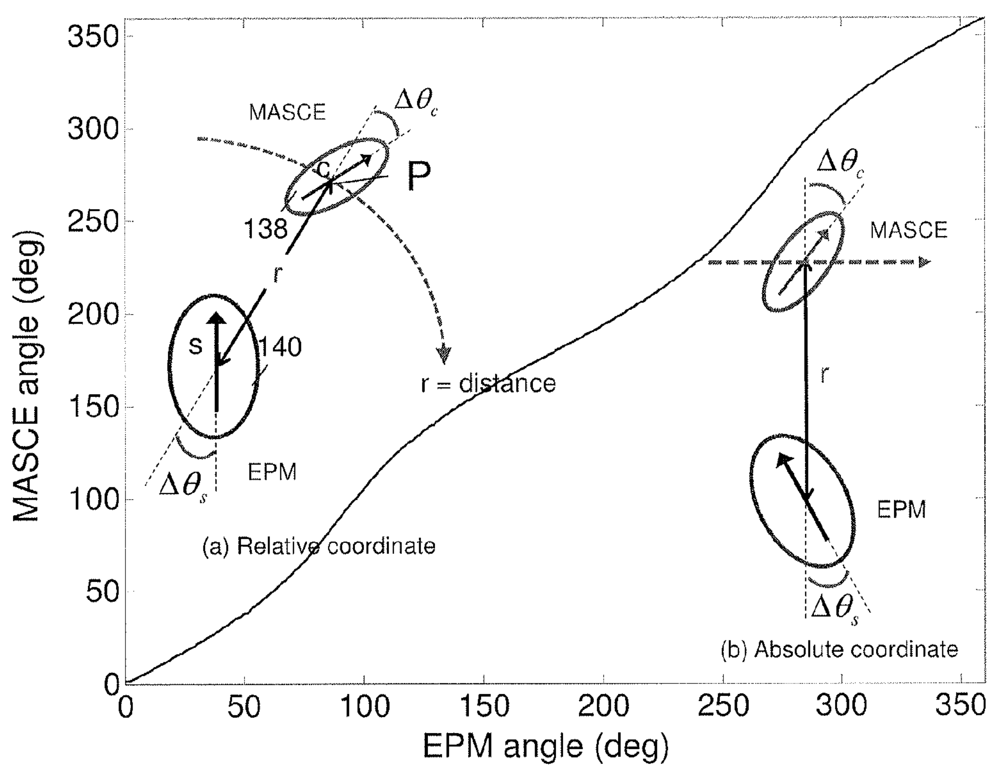
FIG. 9 shows the transformed rotational angles of the source magnet (EPM) and the object magnet (the internal magnets of the MASCE)

FIG. 8 shows the magnetic field and the magnetic force vector in 2-D, which are numerically calculated using Equations (4) and (6). Using this figure, the tilt angle B of MASCE 110 about the substrate can be calculated. FIG. 9 shows the relation between the MASCE's rotation angle, $\Delta\theta_c$, and the EPM's rotational angle, $\Delta\theta_s$. As the summation of $\Delta\theta_c$ and $\Delta\theta_s$ in the relative coordinate frame is determined by the magnetic field vector in FIG. 9, the rotational angle B of the EPM 110 at point P on the circle can be calculated. The EPM's 110 rotational angle, $\Delta\theta_c$, is approximately proportional to the EPM's 110 rotational angle, which means those orientations are approximately symmetrical. Magnetic force vector is already shown in FIG. 8 and it anchors the MASCE 110 on the tissue. The rolling based surface locomotion method is a combination of the symmetrical orientation (ellipse vs. sphere) and the magnetic attraction. FIG. 8 is a simulated magnetic field (flux density) and the magnetic attraction force vector. All the data was numerically calculated using MATLAB. A: The source magnet (Cylindrical magnet, diameter 50 mm, length 80 mm), B: The object magnet (Cylindrical magnet, diameter 5 mm, length 5 mm), C: The magnetic flux density line, D: The magnetic force line, E: The plane of symmetry (red band) F: Contact points.

Modeling and Dynamic Simulation

Figure 10A:
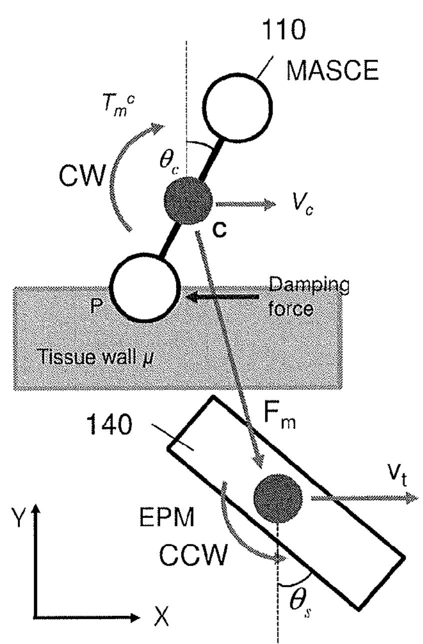
FIGS. 10A-B show schematics of (a) the dynamic relation between the capsule's magnets, the tissue, and the EPM, and (b) a model of the shape morphing process of the capsule.
Figure 10B:
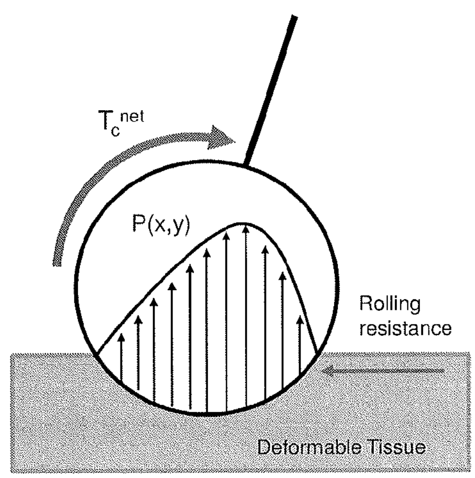

FIG. 10 shows a free-body-diagram of MASCE 110 actuated by the EPM 140. In this model, two internal magnets 112A, 112B of the capsule are simplified as one magnet at the center of the bodyline, and effects of gravity, drag force and buoyancy in a fluidic environment are neglected. First, the driving force $F_x$ governing the translational movement of the capsule is given as $$F_x = F_{m,x} - \mathrm{sgn}\left(v_c - \frac{h\dot{\theta}_c}{2}\right)\mu F_{m,y} - \frac{1}{R_{ap}}\oint_{cnt} xp(x, y)ds - Dv_c \tag{6}$$

where $F_{m,x}$ and $F_{m,y}$ are the magnetic attraction forces between MASCE and EPM in x- and y-directions, respectively, $\theta_c$ and $v_c$ are the rotational angle and the translational velocity of the center of MASCE, respectively, p(x,y) is the compressive pressure distributed over the contact tissue, $R_{ap}$ is the anterior-posterior radius of the contact area, D is the damping coefficient of the tissue, and s is the contact area. Here, $F_{m,y}$ anchors the capsule on the tissue, and $F_{m,x}$ drives the capsule in the horizontal direction. The normal force $F_n$ and $F_{m,y}$ are in equilibrium. Assuming that the effective friction coefficient of the tissue is μ, the friction force is $\mu F_{m,y}$; the sign of the friction force depends on the relative velocity between the rotational velocity of the capsule and the transversal velocity. Lastly, as the compliant tissue is deformed by $F_n$, rolling resistance acts against the movement. As in FIG. 10(*b*), the compressive stress only exists on the contact area and, normally, it is higher at the front contact area.

Next, the rotation of the MASCE 110 is determined by the magnetic torque, the torque exerted by vertical magnetic attraction, the frictional torque, and the rolling resistance moment, respectively, as $$\sum T_c^{net} = T_m^c + \frac{1}{2}F_{m,y}h\sin\theta_c - \left[\mathrm{sgn}\left(v_c - \frac{1}{2}h\dot{\theta}_c\right)\mu F_{m,y}\right]\cdot\frac{h\cos\theta_c}{2} - \oint_{con} xp(x, y)ds \tag{7}$$

where h is the length of MASCE 110 and $T_m^c$ is the magnetic torque about the center of bodyline exerted by the rotating external magnetic field.

According to the model, the sign of the friction force depends on the relative velocity at the contact point. If the rotational velocity is higher than the translational velocity, the friction force in the locomotion direction supports the movement. However, due to the inertia of MASCE, and the rolling resistance of the deformable tissue, the rotational velocity of the EPM needs to be much larger than the translational velocity of the EPM.

Using the above model, MASCE's dynamic behavior is simulated. In the simulations, the ratio between translational velocity and the rotational velocity, κ, is varied and the tracking performance in each case is evaluated. Here, the tracking error is defined as root-mean-square error between the desired position (orientation) of MASCE and the actual position (orientation).

TABLE II

PARAMETER OF THE SIMULATIONS

| Definition | Value |
|---|---|
| EPM (diameter/thickness) | 50 mm/80 mm |
| Residual magnetic flux density $B_{r,ext}$ | 1.4 T |
| Internal magnets of MASCE (diameter/thickness) | 10 mm/6 mm |
| Residual magnetic flux density $B_{r,cap}$ | 1.0 T |
| Friction coefficient | 0.1~0.3 |
| Rolling resistance coefficient | 0.1 |
| Vertical distance between EPM and MASCE | 100 mm |
| Length of MASCE | 30 mm |
| Mass of two heads of MASCE | 8 g |

Figures 11A, 11B:
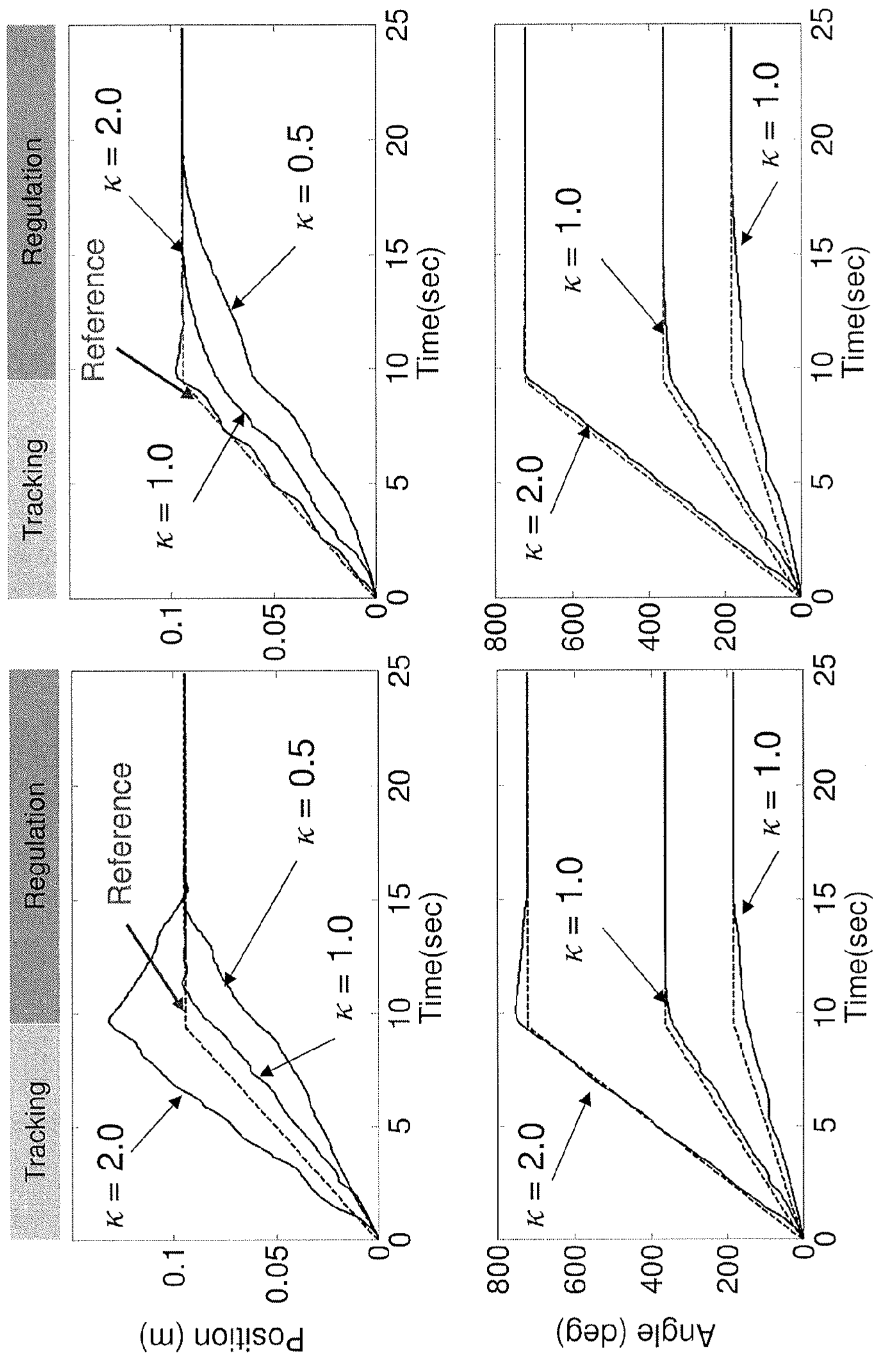
FIGS. 11A-B show the simulated locomotion distance and rotational angle of MASCE and EPM according to different k ratios.

Table II shows the parameter values used in the simulations. In addition to the assumptions in the model, the profile of the compressive stress on tissue is assumed to be uniform. The position and the orientation of MASCE are numerically calculated using Equations (4) and (5). In the calculation, the magnetic flux density vector is calculated using (4), and the force and the torque are determined using Equations (6) and (7). FIGS. 11A-B show the simulated position of MASCE in each κ ratio case. The desired trajectory of MASCE, which also means the input trajectory of EPM, is a ramp-type with 10 mm/sec speed and the desired final position is 90 mm. At a high friction environment, while the ratio κ that is much higher than 1 induces a lead error, the lower than 1 causes a lag error. If the friction coefficient is low, the driving force due to the friction decreases and the MASCE 110 does not move before the EPM 140 as shown in FIG. 11B.

Figure 12A:
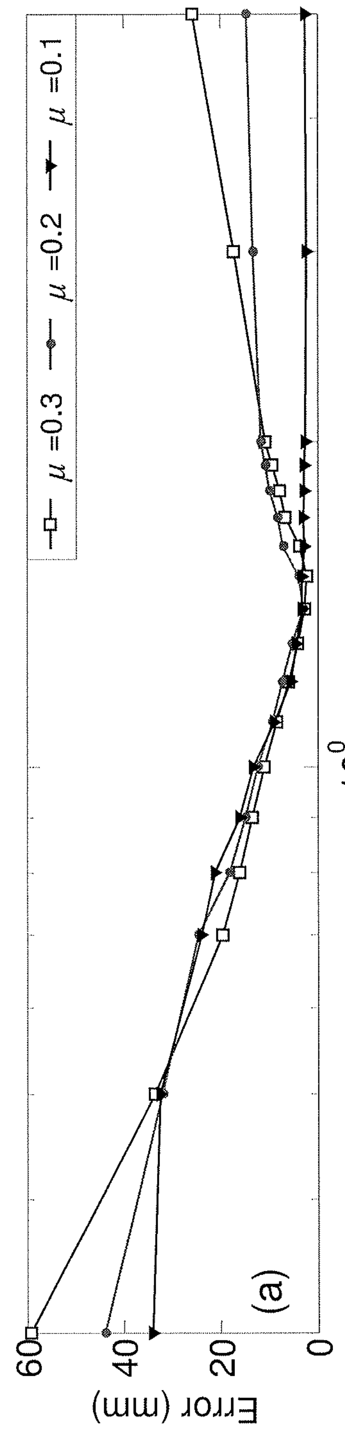
FIGS. 12A-B show simulated comparison of tracking performance according to the ratio k: (a) tracking distance error, center-to-center distance between the desired position and MASCE's actual position; and (b) rotational angle error between the EPM and MASCE.
Figure 12B:
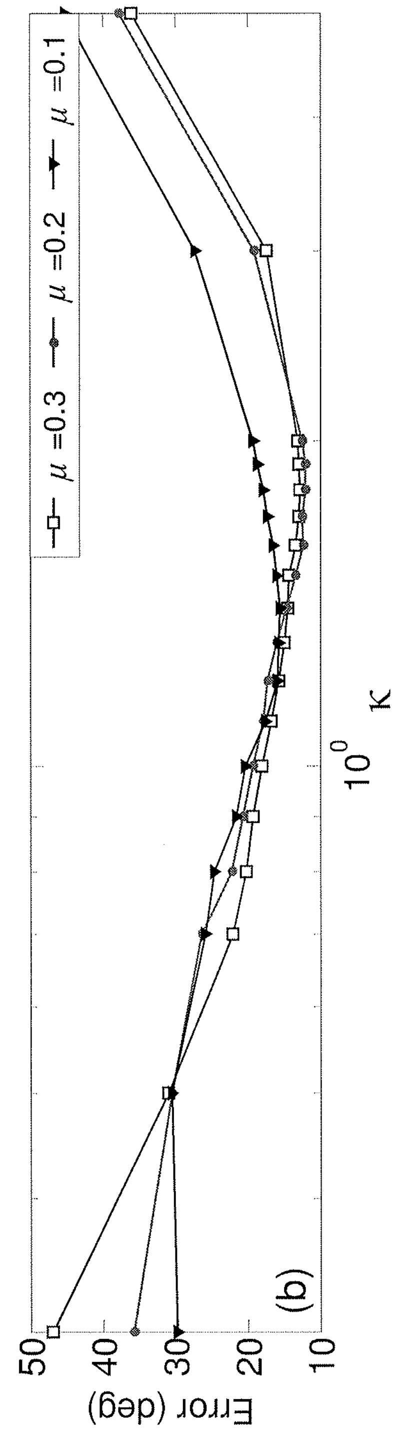

FIG. 12A shows the optimum ratio, $\kappa_{opt}$, for the optimal tracking performance of MASCE. In each ratio κ, the distance error and rotational angle error are calculated and compared. As mentioned above, if the ratio is lower than 1, the lag error is induced because the friction acts against the locomotion. To compensate for the rolling resistance and damping effect of the tissue, the ratio has to be over 1. The simulated optimum ratio ranges from 1.5 to 1.6. High ratio causes a lead error, which is similar to an overshoot. However, if the magnetic attraction between EPM 140 and MASCE 110 is strong enough to overcome the rolling resistance, the capsule is dragged by EPM and, finally, those centers become aligned. If the friction coefficient is low, the error does not increase according to the increases of the ratio because the effective driving force due to the friction force is small. FIG. 12B shows the rotational angle error between MASCE 110 and EPM 140. Due to other torque factors, the simulated angle error is much larger than the theoretical value. However, in this case, the optimum ratio ranges from 1.5 to 1.8 regardless of low friction coefficient. FIGS. 12A and 12B show that the ratios from 1.5 to 1.8 also show a robust tracking performance; the distance and the orientation errors within this range do not result in a large deviation in each friction coefficient case.

Workspace Analysis

Even though the surface locomotion method allows stable and controllable locomotion behavior of the magnetic capsule, its workspace is limited by surface slope. FIG. 13A shows a free-body-diagram of MASCE 110 ascending a slope. To overcome the gravity and ascend this slope, below equality should be satisfied:

$$\chi\frac{\sin\theta}{\cos(\phi-\theta)} < \tan(\phi-\theta)+\mu\left(1+\chi\frac{\cos\theta}{\cos(\phi-\theta)}\right) \quad (8)$$

where θ is the slope angle of the stomach, x is the ratio between the weight of MASCE 110 and the magnetic attraction, ϕ is an angle of location of the EPM 140, and μ is the friction coefficient.

FIG. 13B shows the maximum slope angle in each case. For example, if the magnetic attraction is 2 times of the weight of the MASCE 110, ϕ due to misalignment of those centers is 17 degrees, and the friction coefficient is 0.3, the calculated maximum slope angle is about 25 degrees. In any slope above this angle, the capsule is pulled by EPM and its own weight downwards. If the friction coefficient is lowered, the maximum slope angle is increased because the friction force induced by rolling motion supports locomotion. Also, as the capsule's center is aligned with the center of EPM, the slope angle is decreased because the vertical magnetic attraction is strong. This means that the tracking error would be increased at the boundary of the workspace. It is expected that the strong magnetic attraction increases the maximum slope angle because horizontal magnetic attraction is added on to the normal force and the friction force supports the ascending motion. In FIG. 13C, workspaces at two points A and C are illustrated. Considering convex and concave shapes, the geometry of stomach model is set arbitrarily. The colored areas represent the workspace of MASCE, actuated by the rotating magnetic field.

Drug Releasing Mechanism

Figure 14A:
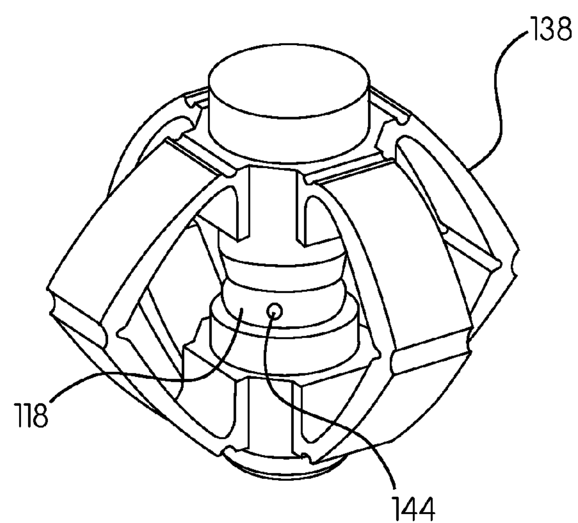
FIGS. 14A-C show photographs of controlled liquid drug releasing using the capsule of the present invention.
Figure 14B:
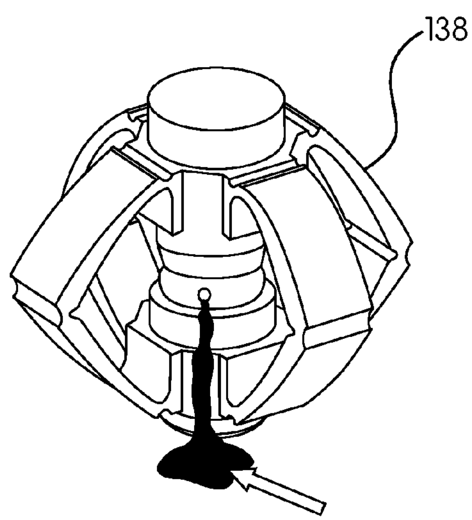
Figure 14C:
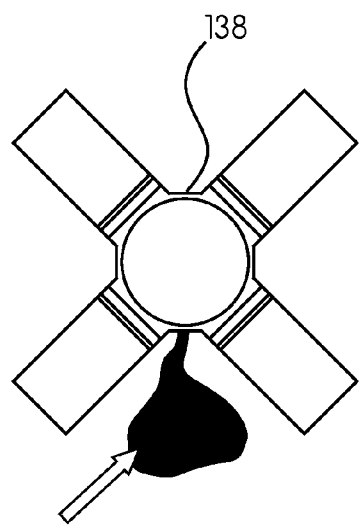

As the therapeutic function demonstration of the prototype MASCE, FIG. 14(*a-c*) shows its drug-releasing capability using the magnetically actuated axial compression. By the axial magnetic attraction, the drug chamber between two internal magnets 112A, 112B is compressed and the drug is released through holes 144 at a critical pressure. In an exemplar demonstration, mucoadhesive polymer (Carbopol CP 971P NF, Noveon Corporation) is used as the sample drug and it is dyed with a blue ink to visualize easily (white arrow in FIGS. 14A and 14C. Due to its high density, it is layered on the target area without Brownian motion.

Figure 15:
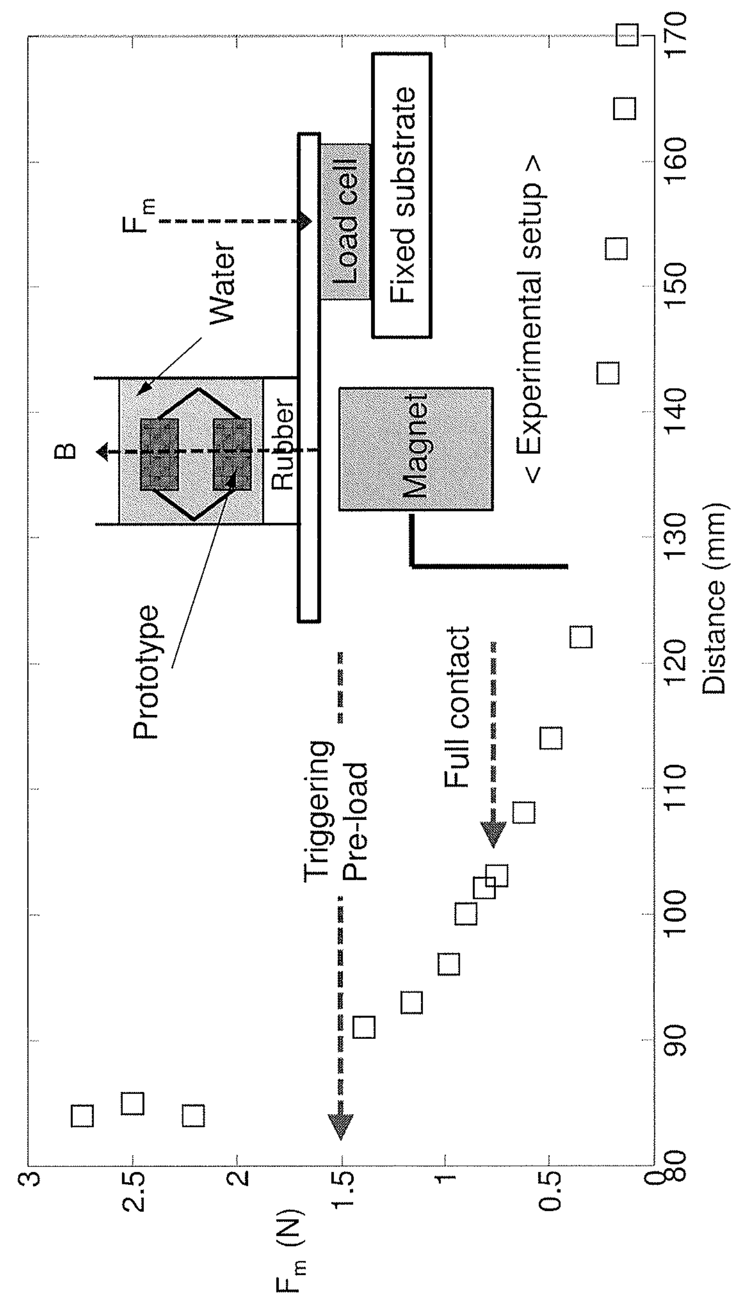
FIG. 15 shows a schematic of an experimental setup and resulting data for compressive force measurements of a drug releasing mechanism of the present invention.

For a MASCE with a drug releasing function, it is important to secure a safety margin for the required compressive axial force between two magnetic heads controlled by the distance control of the EPM 140 (e.g. getting the EPM 140 closer to MASCE) to release the drug in a controlled manner. This compressive force should be much larger than the compressive axial forces induced during the rolling locomotion. Therefore, the required threshold magnetic attractive force for triggering the liquid drug releasing is characterized using a test bench shown in FIG. 15. The MASCE prototype with the drug chamber and one hole is placed in a beaker full of water. The bottom of the beaker is covered with a silicone rubber and mounted to a load cell, which measures the magnetic attraction. The external magnet connected with a passive manipulator is manually controlled and the distance between the capsule and the magnet is estimated using the manipulator. The result in FIG. 15 shows that the MASCE becomes fully compressed with a 700 mN preload force and the drug releasing is triggered when the compressive force exceeds 1.5 N. This result shows that the chamber's stiffness is strong enough to withstand the axial compressive force during the rolling locomotion.

Figure 16B:
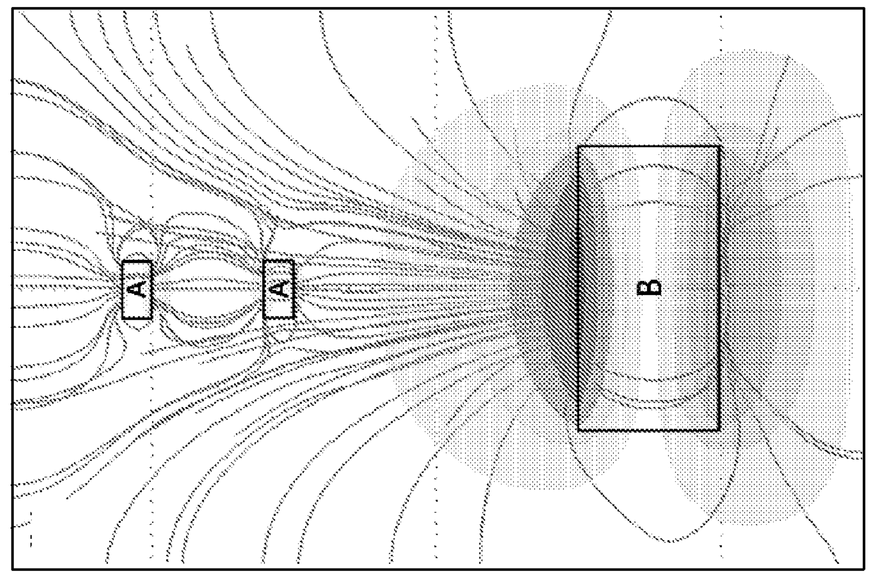
FIGS. 16A-B show (a) finite element analysis assessment of capsule-tissue interaction during drug releasing; and (b) a schematic of the magnetic fields around the MASCE and the EPM.
Figure 16A:
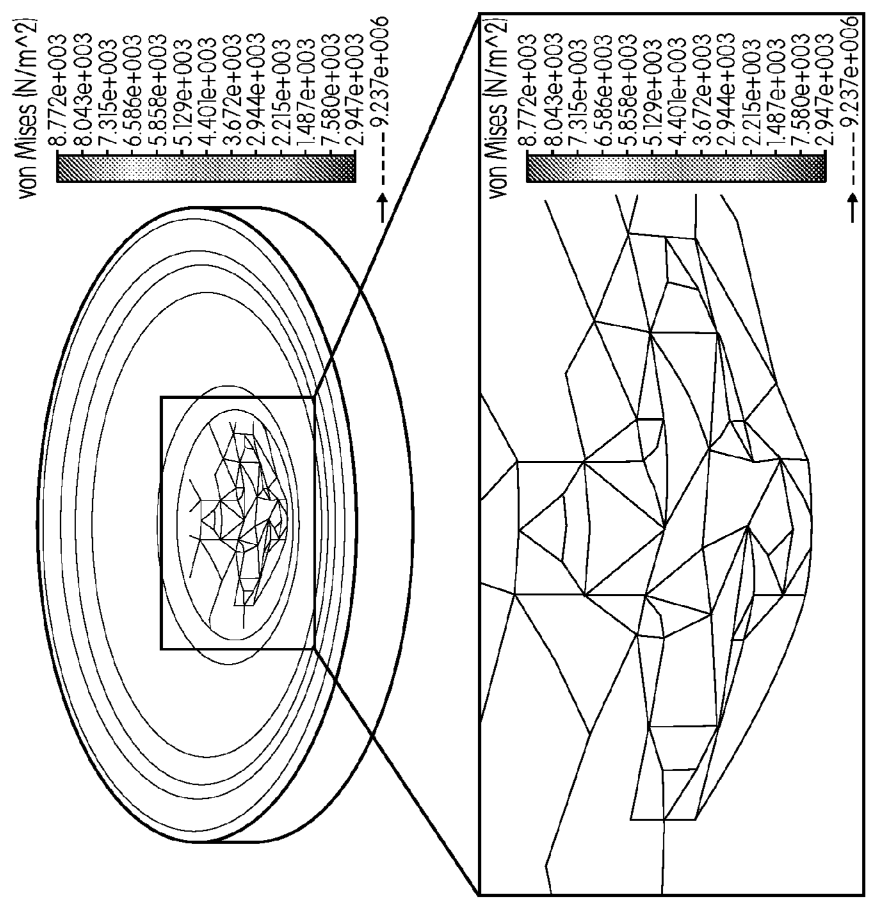

FIG. 16A shows the stress distribution due to the preloading force on the stomach surface during drug releasing. FEA results show that the center of the contact area experiences about 6 kPa of stress, which is about 1% of the tissue destructive stress. FIG. 16B shows the schematic of the magnetic field around EPM 140 and MASCE 110 during drug releasing. The magnetic field of the EPM 140 is deflected around the two internal magnets 112A, 112B, which induces the enhanced magnetic field between these magnets 112A, 112B.

In another embodiment of the use of the present invention for drug delivery, the exterior surface of the capsule can be coated with polymeric drugs to be dissolved in the gastric acid as time goes by. In these two schemes, the drug-releasing rate is not controlled, but the entire process of the shape programming and the drug releasing can be implemented without on-board actuation and powering.

In another embodiment, on-board sensors and actuators to control the drug releasing rate could be used. In this case, on-board batteries are required, but the drug-releasing rate can be precisely and actively controlled according to the drug concentration.

Those skilled in the art will recognize that other methods could be used to control the release of drugs from the device of the current invention.

Experimental Results

Figure 17A:
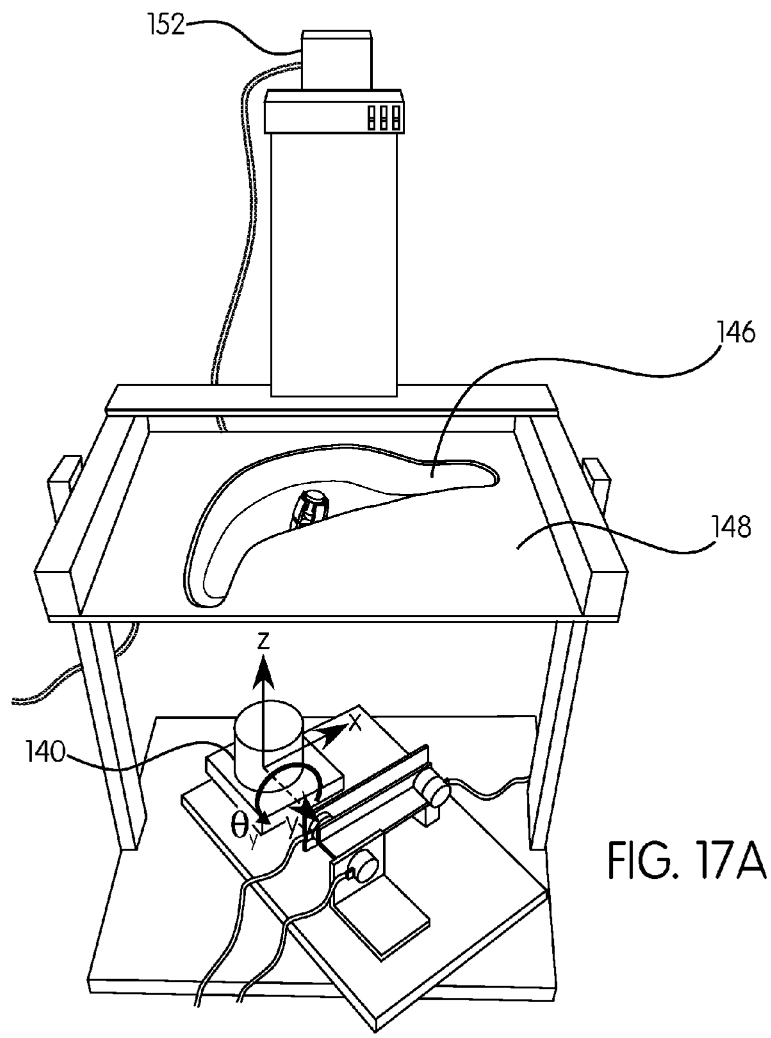
FIGS. 17A-B show photographs of the experimental setup for testing the present invention in a simulated stomach model.
Figure 17B:
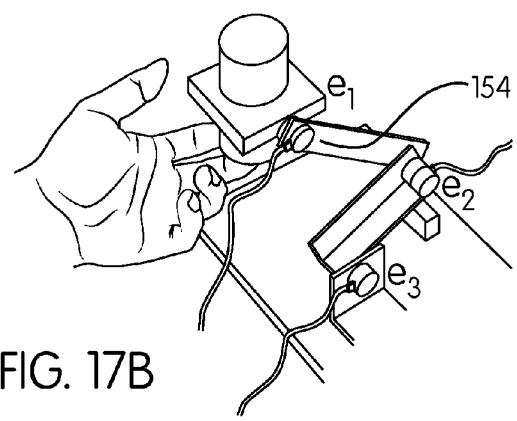

This section shows experimental data of the surface locomotion method of the present invention using rolling motion, and drug releasing-based therapeutic functionality using the capsule's axial compression motion. FIGS. 17A-B show the experimental setup that consists of a synthetic stomach model 146, a rotational substrate 148, a data acquisition board 50 (USB 6008, NI), a webcam 152, and a passive manipulator 154 where the external permanent magnet 140 is mounted. In the experiments using the synthetic stomach model 146, it is very important to select an appropriate material showing a similar mechanical property with a real stomach tissue. The thickness of the silicone rubber (Dow Corning, HS II) stomach model was adjusted to emulate a deformable and compliant stomach wall. The bottom surface of the rubber stomach model membrane 146 is levitated in air to simulate the organ arrangement in a human body and flexibility of the stomach tissue. The purpose of the passive manipulator is to measure the position and orientation of EPM using three encoders e1, e2, e3 (S4, US digital) shown in FIG. 17B, which are used to compute the position of the north pole and the south pole and the orientation about the z-axis. The MASCE 110 position is measured using the captured images of the webcam 152.

Rolling Locomotion Experiments

Figures 18A, 18B, 18C, 18D, 18E, 18F:
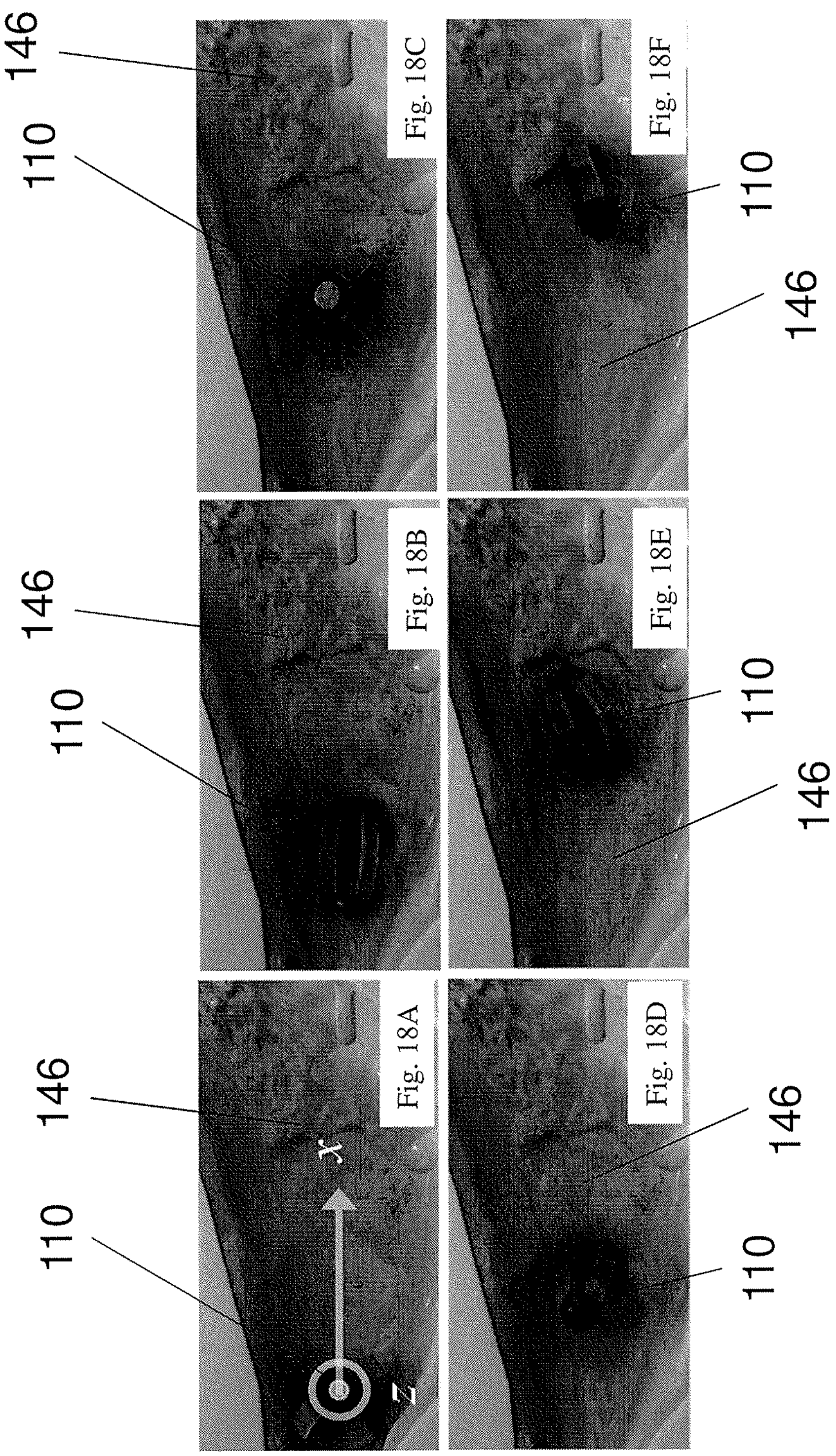
FIGS. 18A-18F show video stills of a rolling locomotion experiment of the MASCE in a simulated stomach model.
Figure 19:
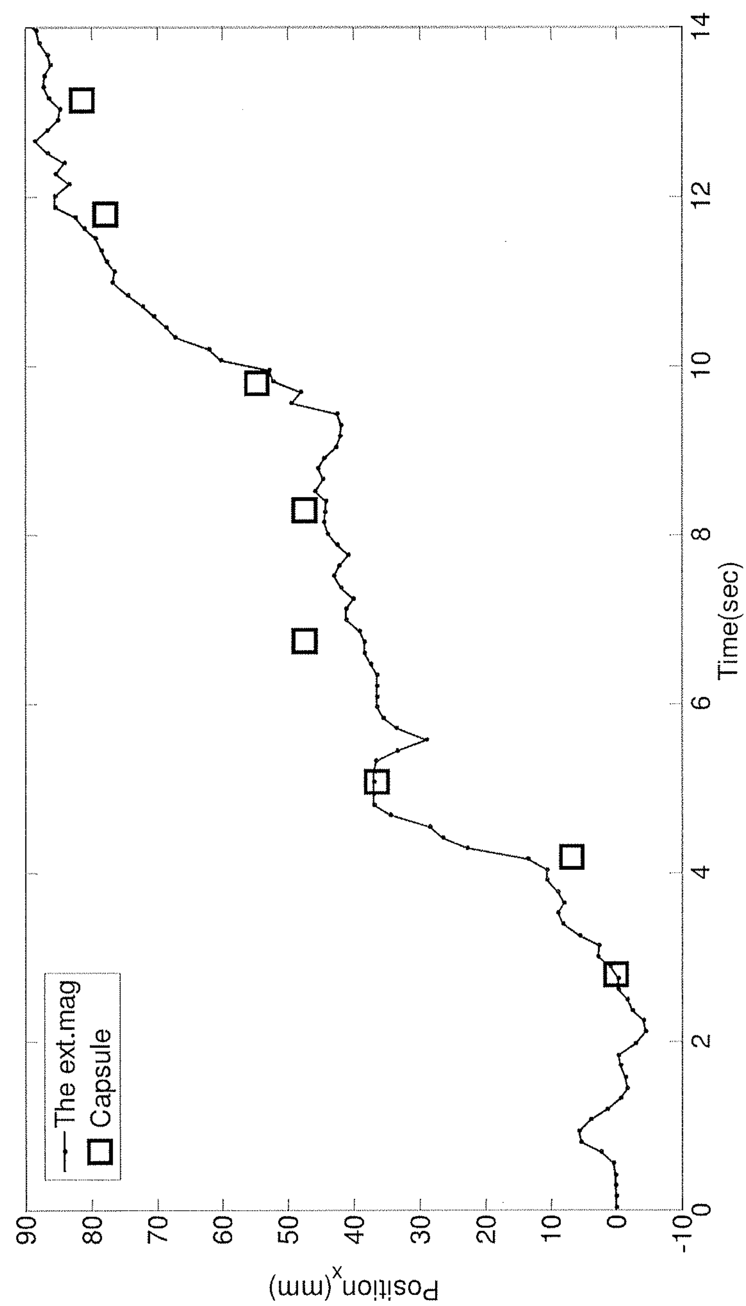
FIG. 19 shows data on center positions of the EPM and MASCE during the rolling locomotion experiment.

The tracking performance of the capsule endoscope was evaluated as follows. The capsule in the 3D stomach simulator was actuated to move in x-direction. FIG. 18 shows snapshots of the experiment. As expected from the simulations, the capsule was able to move in the stomach model using the rolling locomotion. In FIG. 19, the locomotion distance between the EPM 140 and the MASCE 110 over time are compared. It shows that the capsule can track the external permanent magnet 140 closely. At eight points in the experiment, the calculated center-to-center distance error is 5.88 mm, which is below 20% of the capsule body length. The friction coefficient between the silicone rubber and the polyurethane is about 1.07 and the average value of κ during the experiment is about 2.17.

Figure 20:
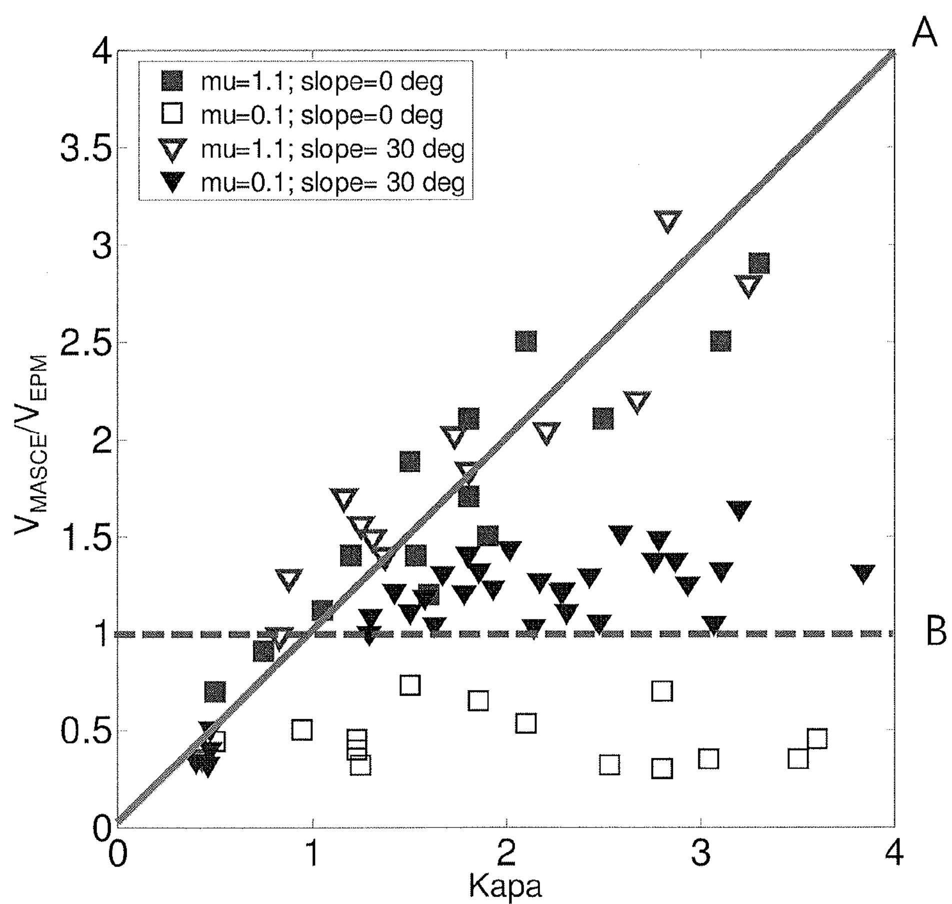
FIG. 20 shows data on experimental tracking performance results for different k, friction coefficient numbers, and surface slopes (0 and 30 degrees)

FIG. 20 shows experimental results related to the effect of rotational velocity, κ, on the tracking performance. The first objective of the experiment was to evaluate the robustness of the rolling motion, and the second objective was to investigate the effect of the slope on the tracking performance. First, a flat 2-D silicone rubber surface was used in these experiments instead of a synthetic 3D stomach model. In a high friction interface ($\mu$=1.1), MASCE's 110 velocity is proportional to κ because the propulsive force by rolling motion is dominant on the MASCE's 110 motion. Therefore, too high rotational speed induces a lead tracking error. On the other hand, at a low friction environment ($\mu$=0.1), the propulsive force is saturated around κ=1.5. If the MASCE's 110 rolling speed is not high enough as in the case of κ=0.5, the capsule lags behind the EPM 140. The optimum κ ranges from 1 to 1.5, which is consistent with the simulation results in FIG. 12.

In addition to the friction, surface slope is also important for stable rolling locomotion. The previous analysis above shows that the maximum slope angle that the capsule can have stable rolling depends on the friction force. FIG. 20 shows that the MASCE 110 cannot track the EPM 140 when the substrate is tilted 30 degrees and $\mu$=0.1. However, if the friction force is strong, the enhanced tracking performance could be maintained.

Drug Releasing Experiment

Figures 21A, 21B, 21C, 21D, 21E, 21F:
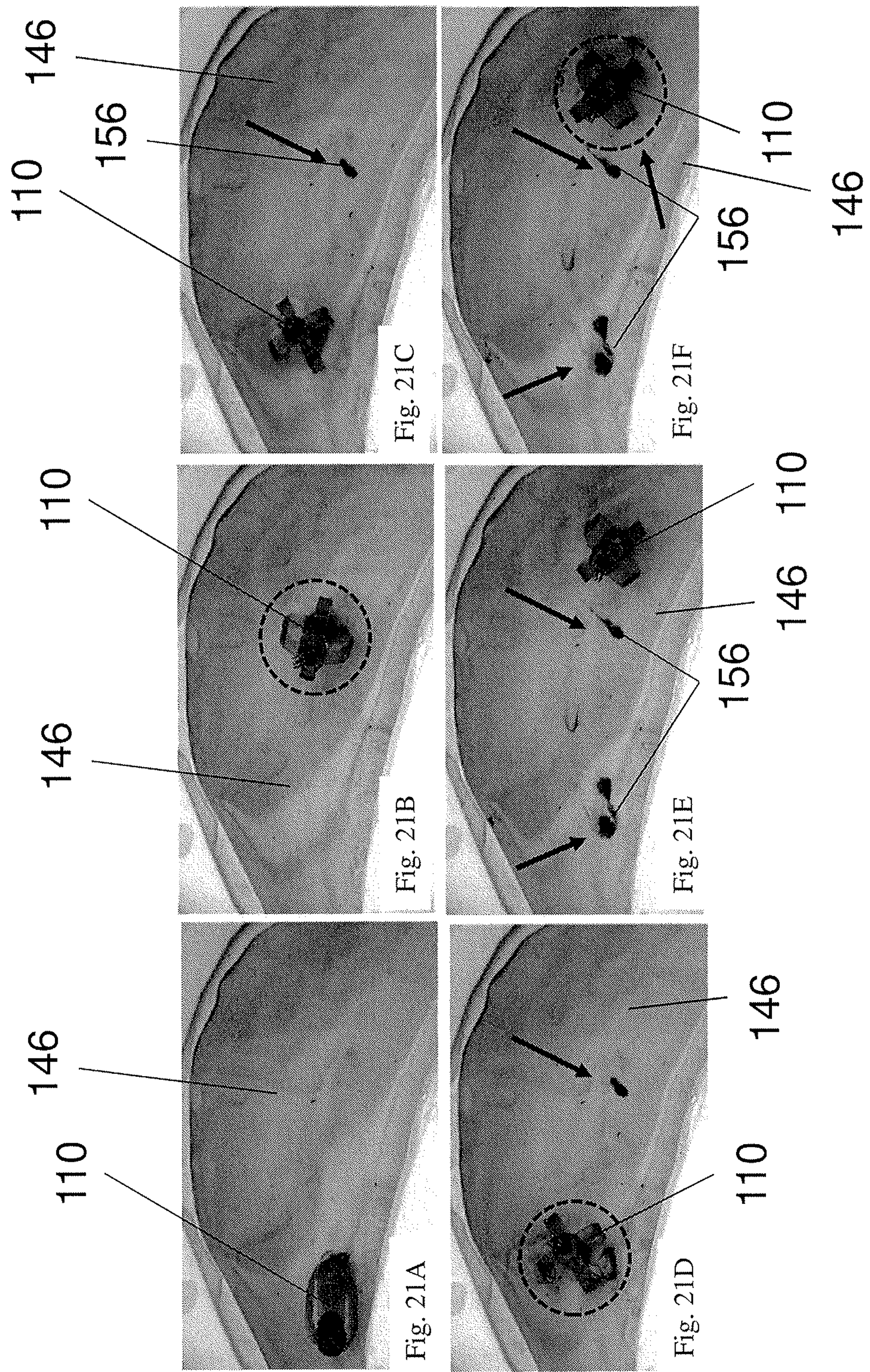
FIGS. 21A-F show video stills of an experiment on rolling locomotion and multiple drug releasing events.

The controllable drug releasing capability of MASCE was experimentally verified. First, a dyed mucoadhesive 156 was injected into the chamber to observe the trace of the released drug visually and the stomach simulator 146 was filled with water to simulate the fluidic environment. The effect of buoyancy on the MASCE 110 was negligible because the weight of the MASCE 110 is much higher than the buoyancy force. MASCE 110 was actuated by the rotating EPM 140. MASCE 110 was intended to release the drug on three different positions by the user's command. FIG. 21 shows the snapshots of MASCE which moves on synthetic stomach 146 using rolling motion and releases drug three times at different locations. The drug 156 inside the chamber was not released by the magnetic forces during the rolling locomotion and only released by the increased external magnetic field of EPM 140 by moving it closer to MASCE 110. The released drug volume at each compression and maximum number of cycles to repeat the drug releasing task are limited by the volume of the drug chamber, which was 174 $mm^3$ in the experiments.

Use for Extended Drug Delivery

In addition to the use of the present invention for short term drug delivery as described above, the present invention could also be used for longer term, semi-implantable drug delivery applications. Adapting the magnetically actuated soft capsule endoscope (MASCE) design to this specific application, a modified soft robot's shape is actively changed to approximately a sphere to stay inside stomach for long durations to deliver a drug passively for long durations. When the drug is depleted, the robot recovers its original cylindrical shape by external permanent magnetic 140 actuation to be naturally discharged. Such a semi-implantable drug delivery system can be used to deliver drugs for long durations for elderly or other patients with limited care facilities, patients with chronic diseases for which continuous drug delivery is needed, etc.

Exemplar Application Scenario

Figure 22:
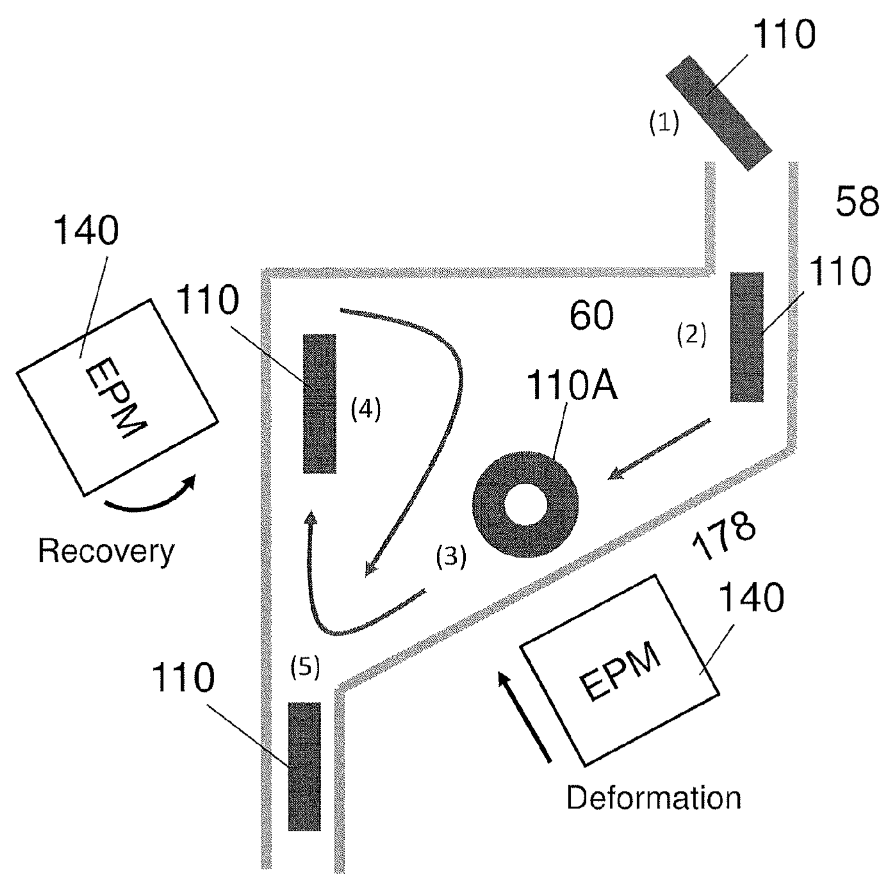
FIG. 22 shows a schematic of a use of the present invention for drug delivery in the stomach.

FIG. 22 shows an exemplar application scenario of the shape-programmable MASCE 110. After being swallowed, the MASCE 110 moves inside esophagus 158 by peristalsis 178 while maintaining its cylindrical shape. When it reaches the stomach 160, it is changed to a spherical shape by external magnetic attraction generated by a strong external permanent magnet 140 (EPM), directly controlled by a doctor. The spherical MASCE 110 would be moved to the lower region of the stomach by gastric peristalsis, but cannot pass to the next organ, duodenum, due to its large diameter. Remaining in the stomach, the drug inside the capsule is steadily released. The released drug flows to the duodenum and is absorbed into the blood vessels. After the depletion of the drug, the MASCE's 110 cylindrical shape is recovered through manipulation of the external magnetic field. The soft robot that has recovered the cylindrical shape can move into duodenum 162 by gastric peristalsis. Finally, it is discharged through the anus (not shown).

Design of the Shape-Programmable Magnetic Capsule Robot

Shape Deformation to a Spherical Shape

Figure 23B:
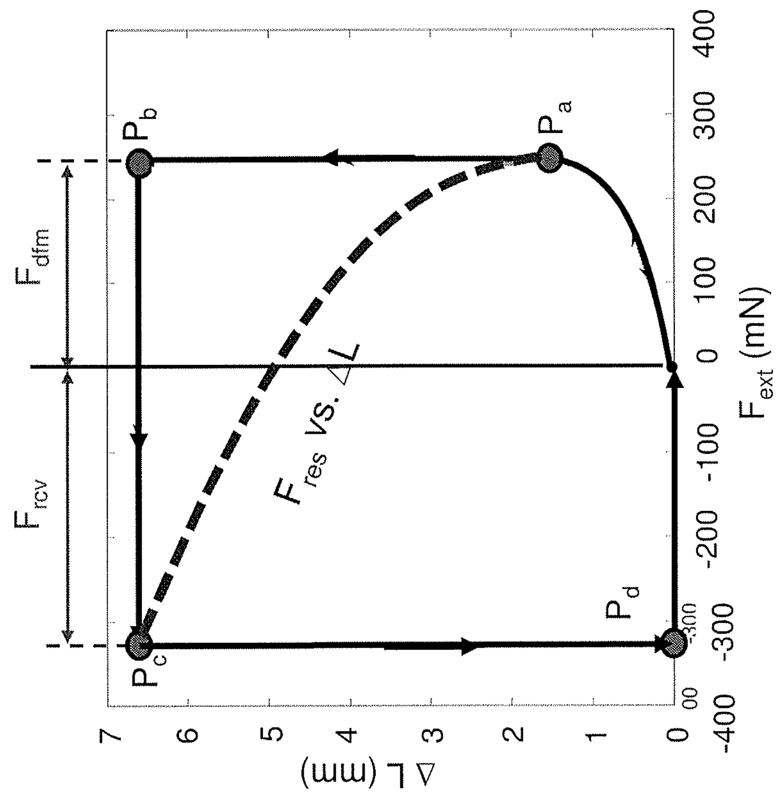
FIG. 23B shows the shape deformation curve of an exemplar soft capsule robot fabricated according to the present invention.
Figure 23A:
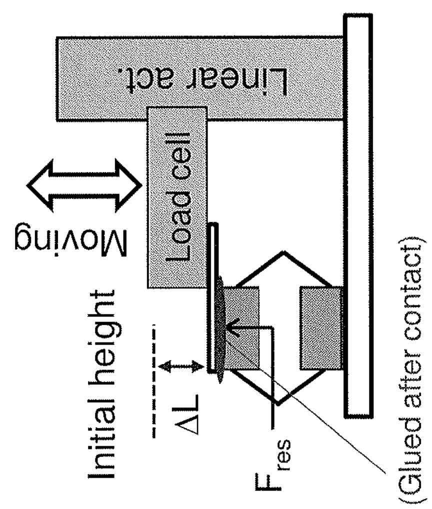
FIG. 23A shows schematics if the experimental setup to measure axial load based compression and shape change of an exemplar soft capsule robot fabricated according to the present invention.
Figures 24A, 24B, 24C:
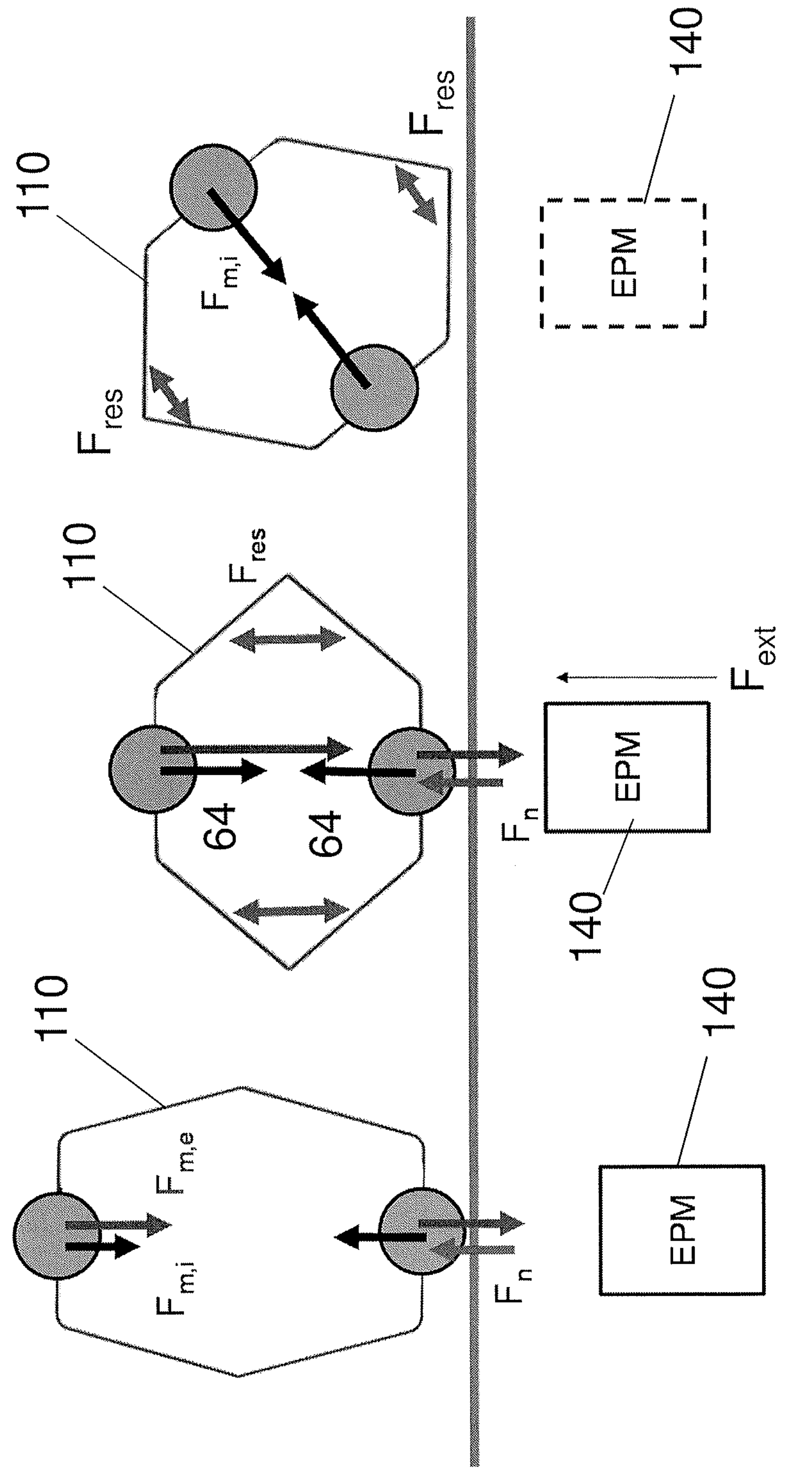
FIGS. 24A-C show schematics of the shape deformation process of a capsule robot fabricated according to the present invention.

As mentioned above and illustrated in FIGS. 1E-F, two tiny internal permanent magnets 112A, 112B are embedded in both ends 114A, 114B of the MASCE 110. Their magnetization directions are co-axial in the direction of the MASCE's 110 length L. The shape deformation from cylindrical to spherical shape is implemented by increasing the external magnetic field by the external permanent magnet 140. The shape deformation curve of FIG. 23B shows the entire process of the MASCE's 110 shape changing process. When the attractive external magnetic field is applied, the soft MASCE 110 aligns with the field direction and stays in that direction on the tissue wall as can be seen in FIG. 24A. If the external magnetic attraction, $F_{ext}$, becomes stronger than a critical axial compression force, $F_{dfm}$, the soft MASCE 110 will be compressed and both internal permanent magnets 112A, 112B contact each other as shown in FIG. 24B by arrowheads 164. Here, the internal magnetic attraction minus the elastic recovery force $F_{res}$ of the side-linkages is the pure residual force of the MASCE 110. If the net force is negative (i.e. the point $P_c$ is on the left of the plane in FIG. 23B), the capsule cannot recover its initial shape even after removing the external magnetic field 140 as displayed in FIG. 24C. In this state, the soft MASCE 110 retains its shape deformation.

Shape Recovery to a Cylindrical Shape

The shape recovery of the soft MASCE 110 is achieved during its rolling motion created by the rotation of the external permanent magnet 140. The axially compressed MASCE 110 maintains its shape using the internal magnetic attraction. If an external force stronger than $F_{rcv}$ is applied to detach two internal magnets, the residual force becomes positive and the soft MASCE 110 can recover its initial shape. This process follows the $P_c$-$P_d$-O route of the shape deformation curve in FIG. 23B.

Figures 25A, 25B, 25C:
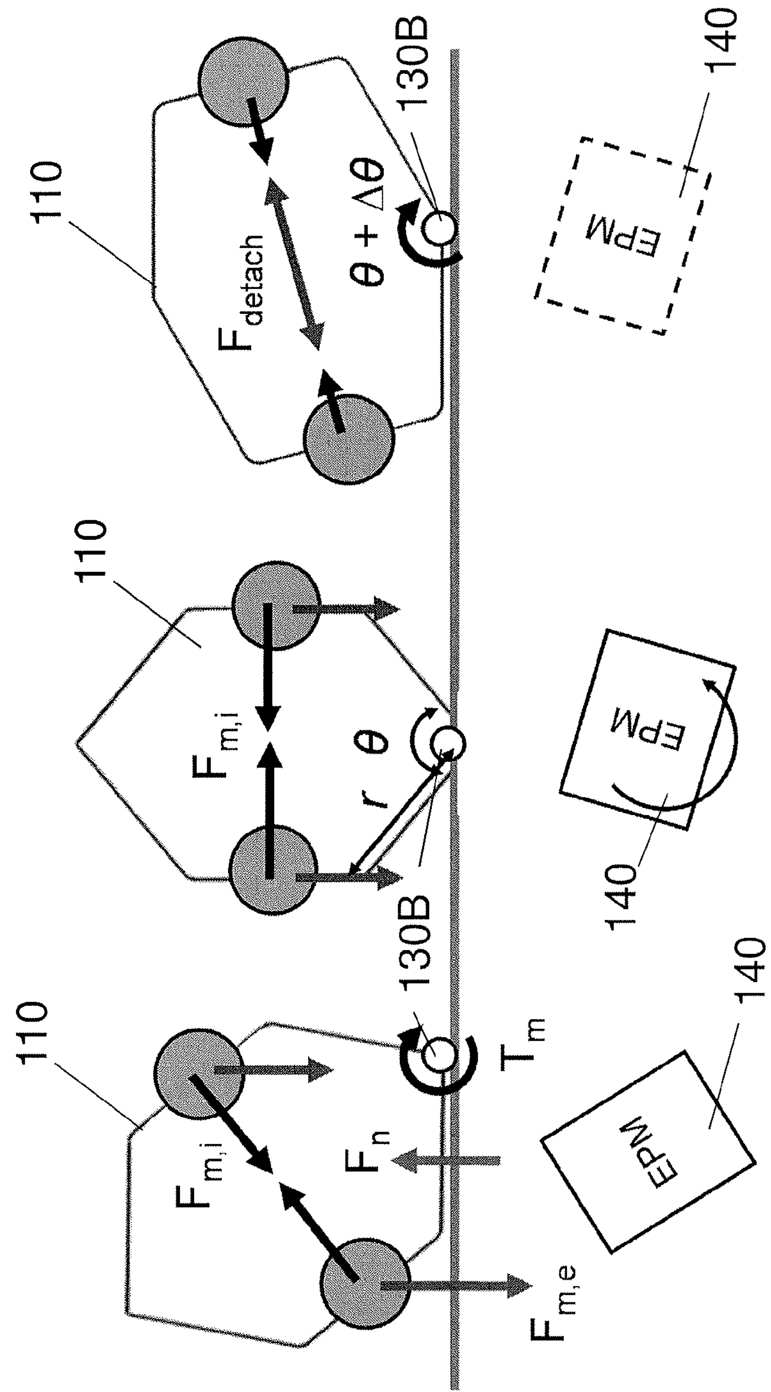
FIGS. 25A-C show schematics of the shape recovery process of a capsule robot fabricated according to the present invention.

FIGS. 25A-C show the free-body-diagram of the MASCE 110 during shape recovery. The process of shape recovery employs magnetic torque and magnetic attraction simultaneously. Under the influence of the external magnetic torque, the MASCE 110 is rotated and the flexure hinge 130B becomes a pivot of the rotating MASCE 110 (FIG. 25A). During its rotation in FIG. 25B, there exists a short period that the flexure hinge angle (θ) is widened by the magnetic attraction between the two internal permanent magnets 112A, 112B and the external permanent magnet 140. This rotational moment is transformed to a detachment force to enable the shape recovery of the magnetic capsule as in FIG. 25C.

Figure 26:
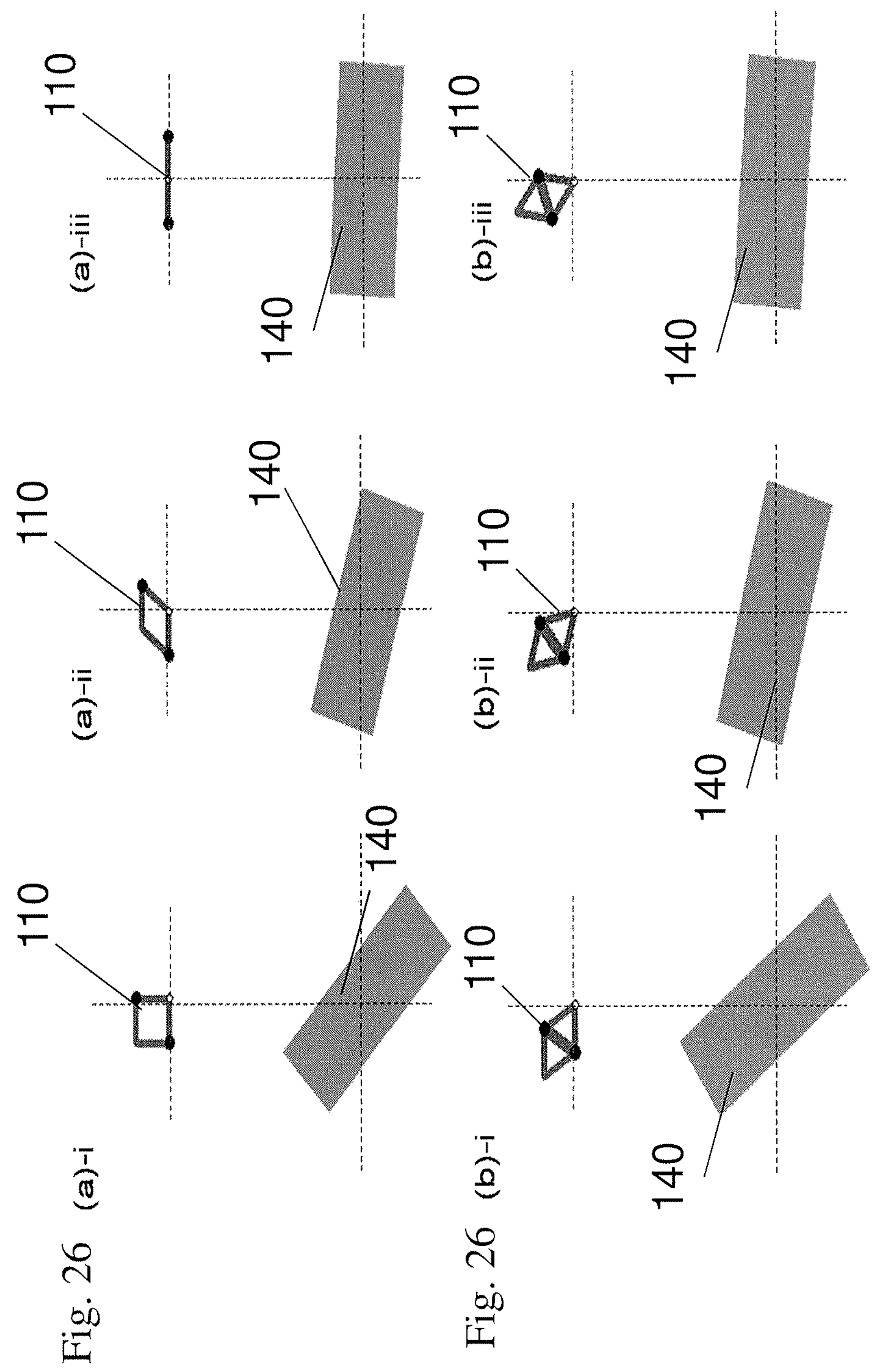
FIGS. 26A-B show schematics of the shape recovery process of a capsule robot fabricated according to the present invention.

However, there is one more factor, which affects the shape recovery process: the flexure hinge angle (θ). If the flexure hinge angle (θ) is small, the conversion ratio of the external magnetic attraction to the detaching force degrades. For example, even though the same magnitude of the external magnetic attraction is applied, the detaching force where the flexure hinge 130B is 60 degrees is 42% lower than that where it is 120 degrees. The relation between the flexure hinge angle (θ) and the ratio between the external magnetic attraction ($F_{m,e}$) and the critical force for the shape recovery ($F_{rcv}$) to enable shape recovery is $$M_{dtch} = r\sin\frac{\theta}{2}F_{m,e} > r\cos\frac{\theta}{2}F_{rcv} = M_{rcv} \tag{9}$$

which is based on a static analysis. For a dynamic analysis, a more rigorous condition would be required. For example, FIG. 25(*b*) is a highly unstable state. If flexure hinge angle (θ) is very acute, the MASCE 110 would be flipped over abruptly before the internal permanent magnets 112A, 112B are separated completely. Therefore, using the dynamic model of the rolling locomotion described above, a dynamic simulation was conducted to investigate the design condition for the shape recovery. Table III shows assumptions of the 2-D dynamic simulation and FIGS. 26*a-b* show the snapshots of the simulation. In the simulation, the initial angle and the distance were variously set and a determination was made on whether the magnetic capsule experiences the shape recovery or not. FIG. 26(*a*)i-iii shows that the link between the two internal magnets are disconnected due to the torque at the flexure hinge 130B, while FIG. 26(*b*)i-iii shows that the link is not disconnected and is instead flipped over by the magnetic torque without the shape recovery.

TABLE III

PARAMETER OF THE SIMULATIONS

| Definition | Value |
|---|---|
| External permanent magnet (NdFeB) Diameter/thickness | 50 mm/80 mm |
| Residual magnetic flux density ($B_{r,ext}$) | 1.4 T |
| Internal magnets of MASCE (diameter/thickness) | 6 mm/6 mm |
| Residual magnetic flux density ($B_{r,cap}$) | 1.0 T |
| Length of the capsule | 30 mm |
| Mass of the capsule | 8 g |

Figure 27:
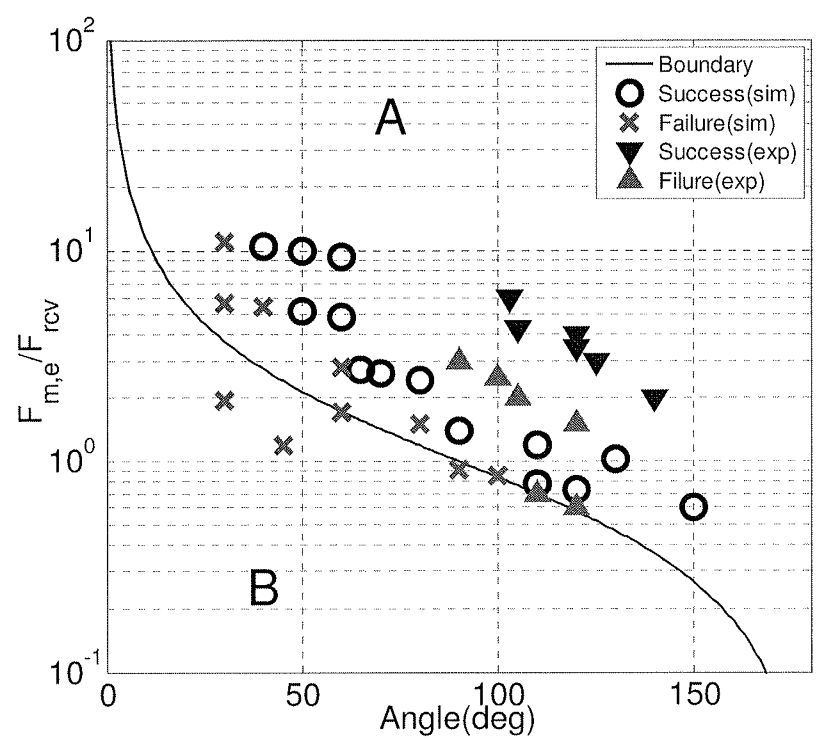
FIG. 27 shows simulation results of the shape recovery process of a capsule robot fabricated according to the present invention.

FIG. 27 shows the simulation results. First, the boundary that divides the plane represents the static analysis condition as given in Equation (9). In the upper side of the plane, i.e., the region A, the static analysis predicts that the magnetic capsule robot recovers its initial shape, while the failure of shape recovery is predicted in the region B. FIG. 6 shows that the dynamic analysis requires stronger magnetic attraction ratio (Fm, e/Frcv) for shape recovery. We conducted an experiment to investigate positions of design variables of our soft capsule prototype (θ=90-140°; Frcv=180-360 mN; Fm, e=252-1025 mN). The experiment showed that the capsule had appropriate safety margins inside of the predicted boundary.

Robot-Tissue Interaction Characterization

Due to gastric peristalsis, the semi-implantable soft MASCE 110 experiences a periodic continuous external force. Here, the interaction between the capsule and the tissue could induce high tissue stress. The soft MASCE 110 design can reduce this tissue stress significantly because the entire body of the soft MASCE 110 is made of soft elastomer and includes no sharp edges. The passive shape adaptation capability of the soft MASCE 110 is also useful to reduce the local stress concentration on the tissue.

After changing the shape of the soft MASCE 110 into a sphere as in FIG. 24B, such shape also reduces the stress concentration on the tissue. If the stress concentration is too high due to any unexpected reason, the MASCE 110 could convert its spherical shape passively to its original cylindrical shape. This passive recovery due to high external forces is undesirable for long duration drug delivery operation of the MASCE 110 while it automatically makes the robot safe against any unexpected high external stresses to prevent any pain or discomfort.

Figures 28A, 28B:
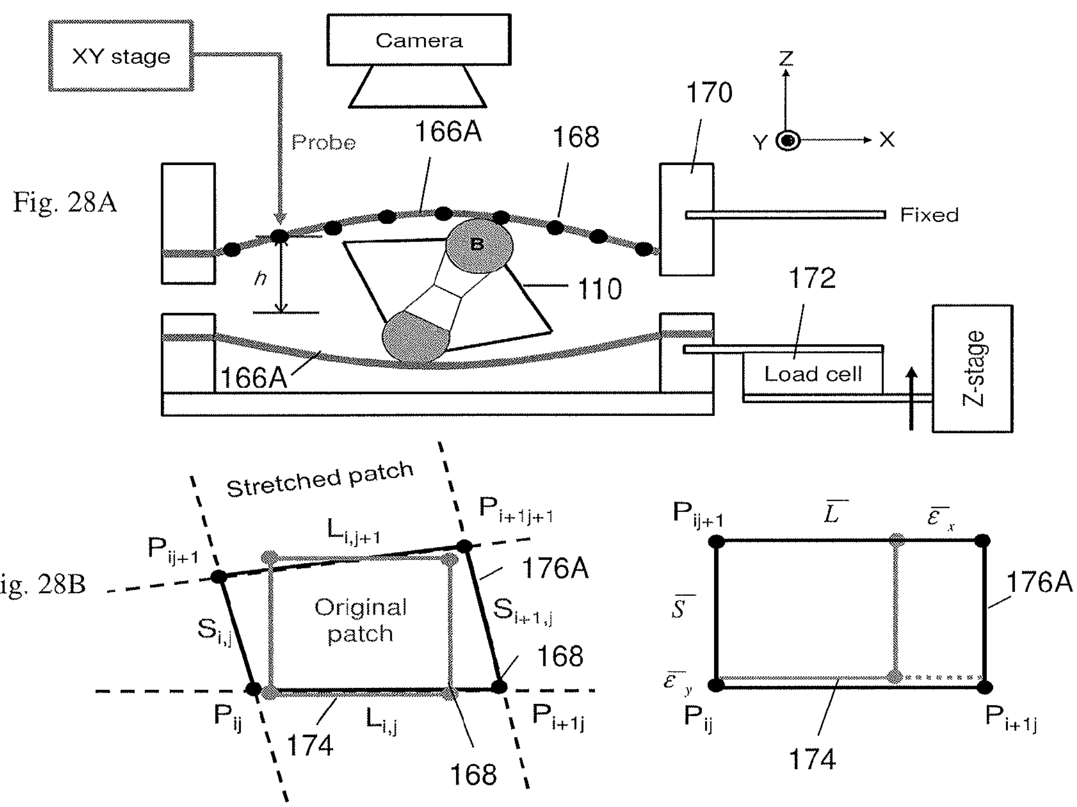
FIGS. 28A-B show (a) schematics of the experimental setup for tissue-capsule interaction measurement; and (b) schematics of bi-axial stress calculation using the bi-axial strains.

Experiments were conducted to investigate how much tissue stress is induced by the soft MASCE 110 under simulated gastric peristalsis forces. FIG. 28(*a*) shows the experimental setup which was used to simulate the peristalsis of the stomach. The artificial stomach wall is made of highly compliant polyurethane (BJB enterprise, F-15); polyurethane elastomers and silicone rubbers are widely used in artificial organ models because their compliance and viscoelastic properties can be designed to be similar to actual organs. The soft MASCE 110 is located between two polymer membranes 166A, 166B, which have many visual markers 168. The upper polymer membrane 166A is fixed with a holder 170. The lower polymer membrane 166B is connected with a load cell 172, which is moved vertically by a motorized stage (Newport, MFA-CC) until the preloading force of 1 N is reached; 1 N is the critical preloading force just before the shape recovery of the capsule robot prototype. In the final state, the height of each marker 168 was manually measured using a probe.

Based on the measured height, the bi-axial stress of each stretched patch 174 of upper polymer membrane 166A containing four marker vertexes 168 was calculated. FIG. 28(*b*) shows the plane stress diagrams for the bi-axial stress analysis. First, as shown in FIG. 28(*b*), based on the positions of the markers 168, the stretched lengths ($L_{i,j}$, $S_{i,j}$), of the patch 174 were measured. The stretched trapezoidal patch 176A was simplified as a rectangular one 176B, and the bi-axial strains were calculated based on the average strains. Finally, the bi-axial stresses were calculated as $$\begin{bmatrix} \sigma_x \\ \sigma_y \end{bmatrix} = \begin{bmatrix} 1/E & -v/E \\ -v/E & 1/E \end{bmatrix}^{-1} \begin{bmatrix} \varepsilon_x \\ \varepsilon_y \end{bmatrix} \quad (10)$$

where E is Young's modulus of the membrane, v is Poisson ratio, and $\epsilon_x$ and $\epsilon_y$ are the average strains of the patch in the x-axis and y-axis, respectively.

Figures 29A, 29B:
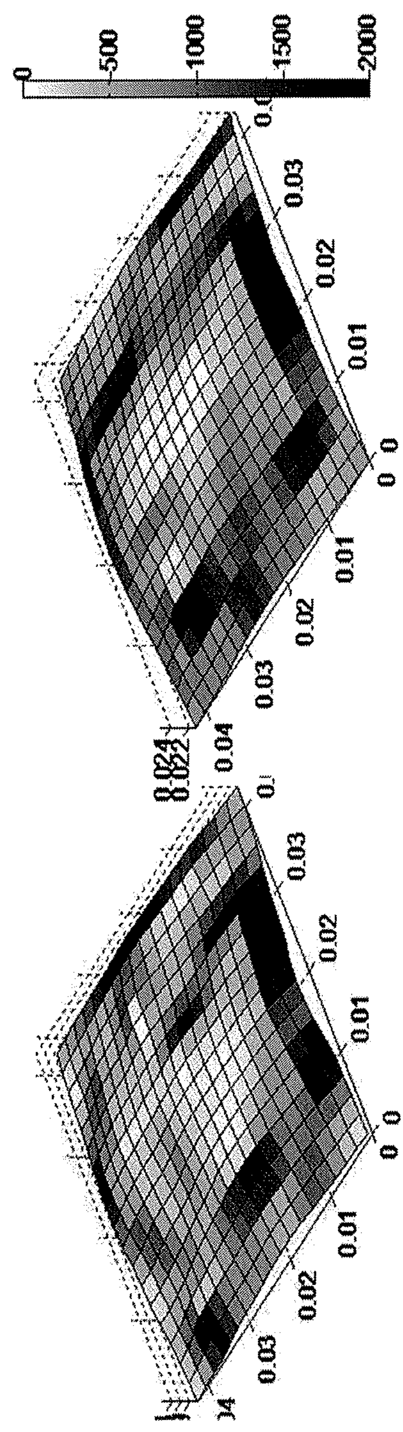
FIG. 29 show (a) photographs, and (b) stress maps of the soft capsule robot between two membranes.

The orientation of the MASCE 110 between two polyurethane membranes 166A, 166B was set in different positions as shown in the first row of FIG. 29. In the first experiment, as shown in FIG. 29A, the spherical MASCE 110 was located on the lower membrane 166B with its lower head and side linkages 126 contacting it. In the second experiment, as in FIG. 29B, the spherical MASCE 110 was located with its circular flexure hinge 130B on the lower membrane 168. The second row of FIGS. 29A-B shows the height of each markers 168 and the membrane 166B stress, which is calculated using Equation (10). The darker the color of the stretched patch is, the more tissue stress is concentrated on the patch.

Figure 30:
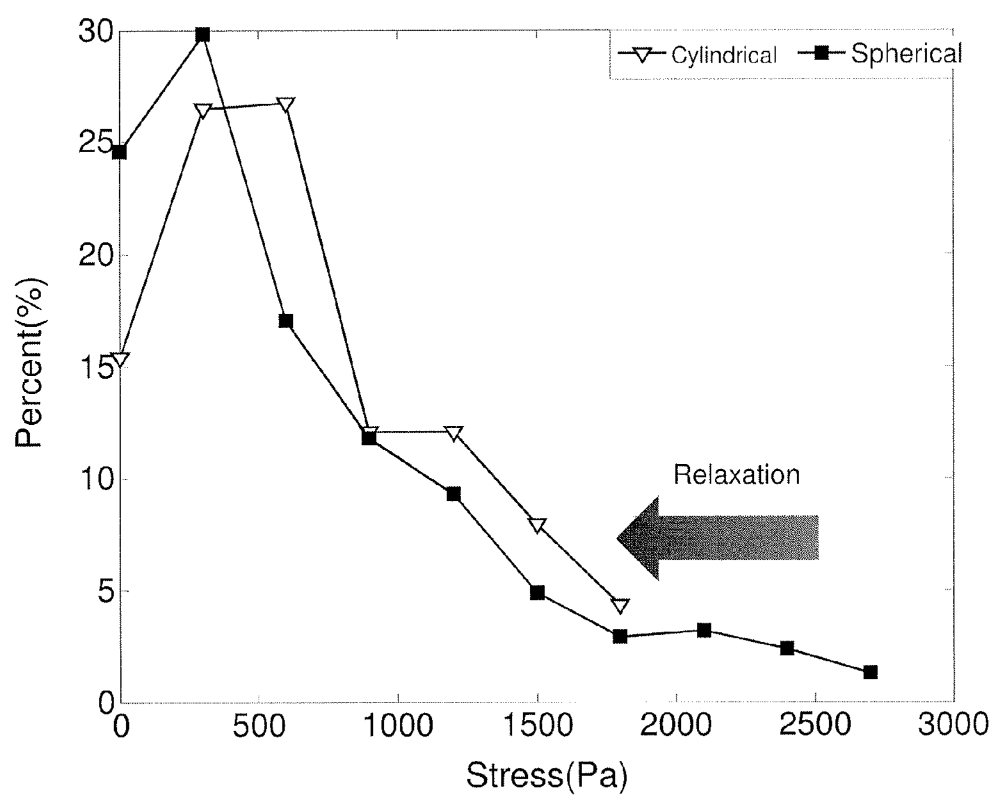
FIG. 30 shows stress distribution analysis for the experiment described in FIGS. 7 and 8.
Figure 31A:
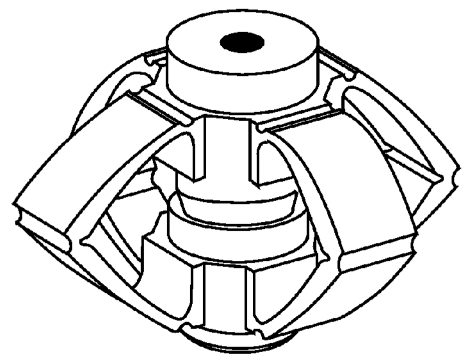
FIGS. 31A-D shows photographs of the shape changing process of a capsule robot fabricated according to the present invention.
Figure 31B:
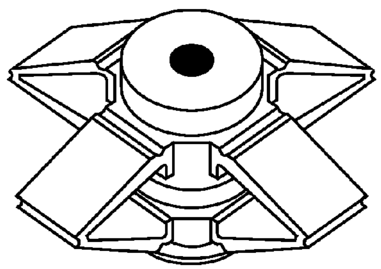
Figure 31C:
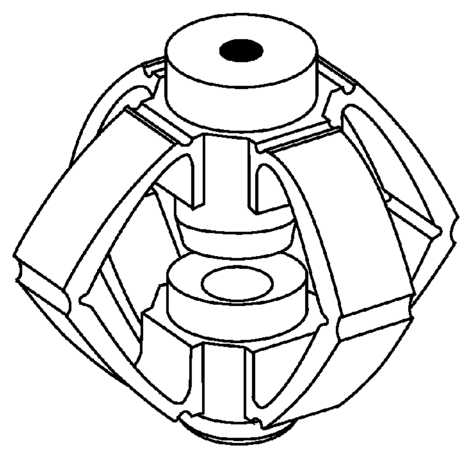
Figure 31D:
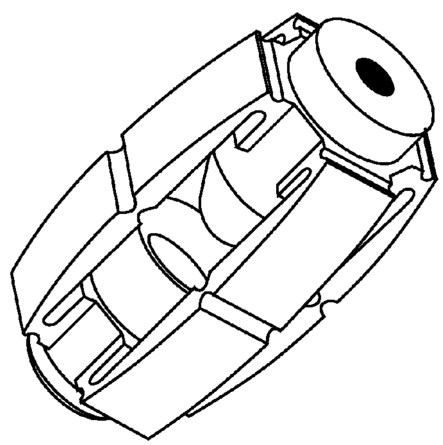

FIG. 30 shows the distribution of the membrane stress, which presents tissue stress relaxation using passive shape recovery. The most stable pose of the spherical MASCE 110 is shown in FIG. 29(*a*). At the maximum preloading force (1 N), the maximum stress of the stretched membrane 166B is about 2.5 kPa, which is lower than the tissue pain level of around 5 kPa [15]. If the preloading force becomes higher than 1 N, the MASCE 110 recovers its initial shape due to the passive restoring force of the flexure hinge 130B. Therefore, the tissue does not experience the stress over 2.7 kPa, i.e. pain. This threshold stress depends on $F_{rcv}$ of FIG. 23B, which means that it can be assigned in the appropriate region by adjusting design variables such as flexure hinge 130B and elastomer material modulus.

Snapshots of the entire process of the MASCE's 110 shape deformation and recovery are shown in FIG. 31. According to the experimental results, the MASCE 110 can maintain its shape under external disturbances such as vibrations and fluidic forces.

The device and control system of the present invention could be used for a variety of applications including extended-term drug delivery, biopsy, heat cauterization, pH sensing, biochemical sensing, micro-surgery, and active imaging.

Magnetically Actuated Soft Capsule with Multi-Modal Drug Release Function

As described above, the present invention is magnetically actuated multi-modal drug release mechanism using a tetherless soft capsule endoscope for the treatment of gastric disease. Because the designed capsule has a drug chamber between both magnetic heads, if it is compressed by the external magnetic field, the capsule could release a drug on a specific position locally. The capsule is designed to release a drug in two modes according to the situation. In the first mode, a small amount of drug is continuously released by a series of pulse type magnetic field (0.01-0.03 T). The experimental results show that the drug release can be controlled by the frequency of the external magnetic pulse. In the second mode, about 800 mm$^3$ of drug is released all at once by the external magnetic field of 0.07 T which induces a stronger magnetic attraction than the critical force for capsule's collapsing. As a result, a polymeric coating is formed around the capsule. The coated area is dependent on the drug viscosity. Contained herein are result of a simulation and various experiments to evaluate the magnetically actuated multi-modal drug release capability. The proposed soft capsules could be used as minimally invasive tetherless medical devices with therapeutic capability for the next generation capsule endoscopy.

Current medical technologies converge towards a certain goal of minimally invasive diagnosis and therapy. Magnetic capsule endoscopy is one of the state of the art medical technologies to represent this trend. Many research groups have demonstrated the magnetic maneuvering of an endoscopic capsule inside a human body or a swine's gastrointestinal (GI) tract.

The present invention integrates therapeutic capabilities into an active magnetic capsule endoscopy requesting less complexity and space than prior art devices designed to perform multi-modal drug release in real time.

Drug Release Mechanism

A. Design and Characterization

Figure 32:
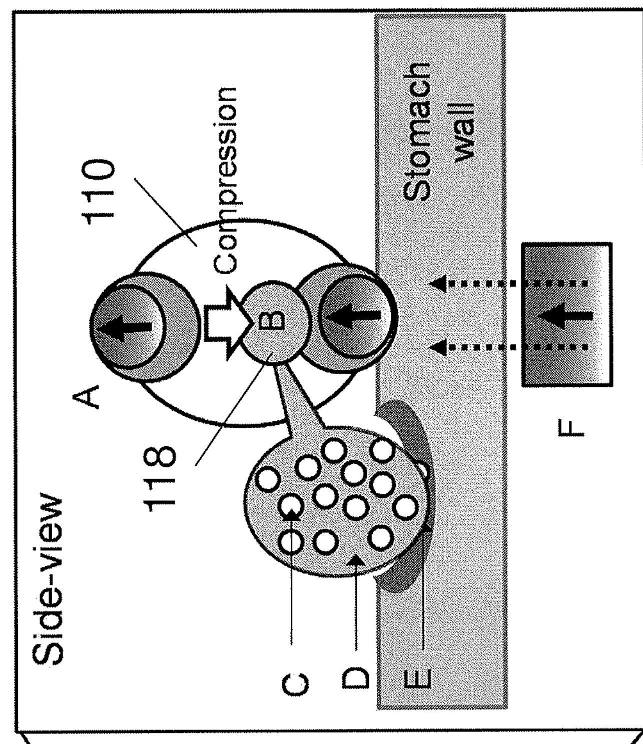
FIG. 32 is a representation of a magnetically actuated soft capsule endoscope (MASCE) of the present invention for active drug releasing where the MASCE is axially contracted by the external magnetic field next to the ulcer or bleeding tissue having a drug chamber that is compressed by the upper head (see the white arrow). A: MASCE with two internal magnets; B: Drug chamber; C: Cytoprotective agent or hemostatic agent; D: Drug solution; E: Diseased tissue; F: External Permanent Magnet (EPM). The black arrows mean the magnetization direction of the magnets. The dotted black lines represent the external magnetic field.
Figure 32:
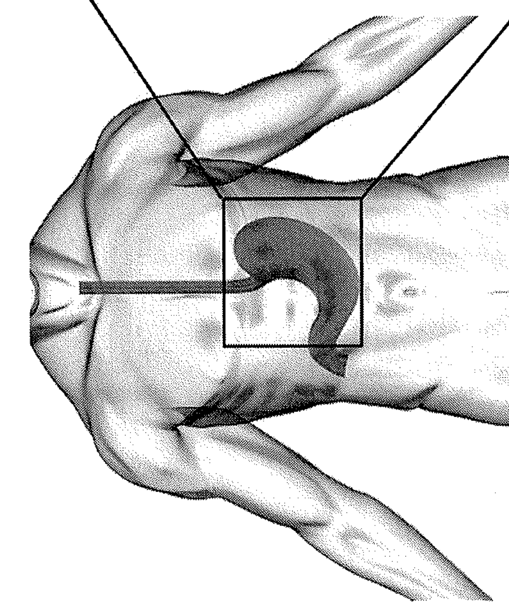

FIG. 32 shows the application scenario of the drug releasing magnetic capsule. After the capsule 110 is magnetically guided to a desired position, it is compressed by the enhanced external magnetic field F. The drug-containing chamber is situated between two heads with internal magnets (see described above). The drug inside the chamber is released through four slits at the corners by the preloading force of the upper head during compression.

Figure 33B:
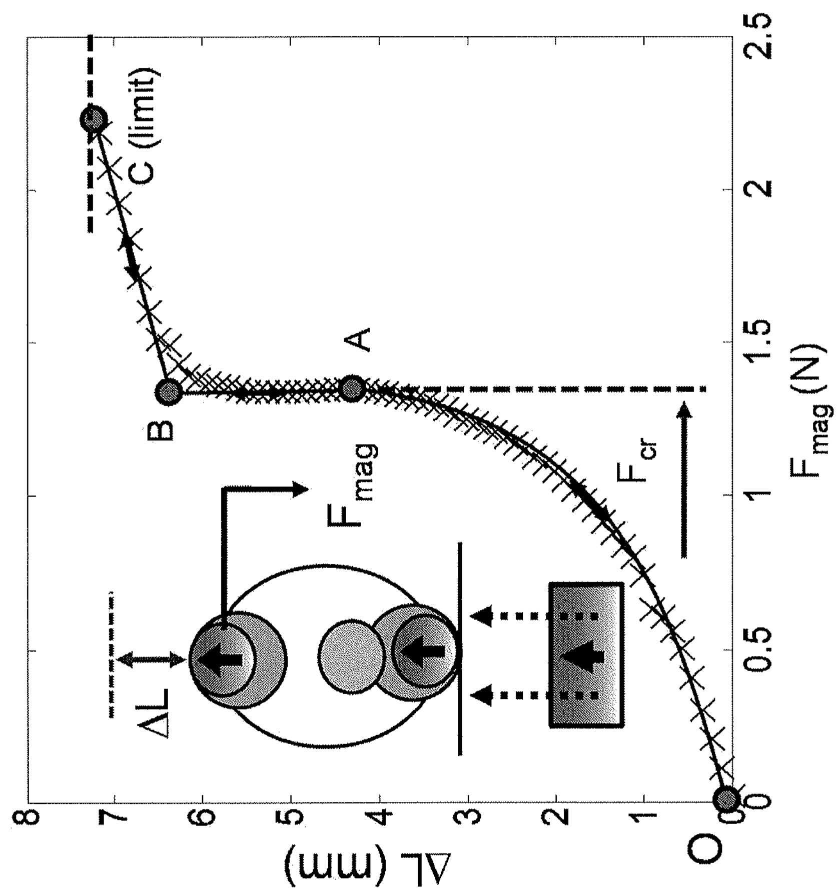
FIG. 33B is an estimated shape deformation curve of the prototype: Compressed length vs. the external magnetic attraction; The blue X-marks mean the results of indentation tests. The capsule is compressed by the external magnetic attraction following the route (O-A-B-C) during the full compression. At A, the chamber is abruptly collapsed by the external force, which is the critical force ($F_{cr}$: 1.34 N). The actual drug release is completed at the point B.
Figure 33A:
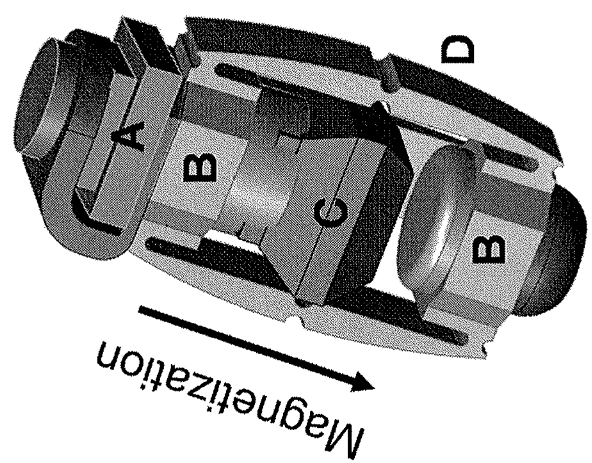
FIG. 33A is a CAD model of the soft capsule for multi-modal drug delivery: A: Camera module, B: Heads with internal magnets, C: Drug chamber, D: Side-linkages.

FIG. 33A shows a CAD model of the designed prototype (see Table IV for the specifications of the prototype). The detailed configuration of magnetically actuated soft capsule endoscope (MASCE) was described above. Because the chamber is made of a soft elastomer, the slits are opened only under the external load. The drug is injected through a small hole in the ceiling of the chamber. The drug chamber is clamped under the upper head and sealed once integrated into the MASCE. FIG. 33B shows the estimated shape deformation curve (the compressed length of the capsule vs. the external magnetic attraction), which is divided into three sections. The first section is between the point O and the point A. In this region, the chamber is compressed as the applied force increases. If the external permanent magnet repeats the linear reciprocal motion, due to a series of pulse-type external magnetic field, the capsule releases the drug slowly and continuously. The second section is from the point A to the point B. A large volume of the drug is released and the area around the target is coated by the released drug. The last section is from the point B to the point C. In this region, a little drug is released while the chamber skin is pressed.

TABLE IV

| SPECIFICATIONS OF THE PROTOTYPE | |
|---|---|
| Diameter of capsule head (initial/compressed) | 15 mm/20 mm |
| Length (initial/compressed) | 40 mm/30 mm |
| Mass | 6.0 g |
| Internal Magnets: | |
| Size (cylindrical) | Diameter: 8 mm; Length: 8 mm |
| Material | NdFeB |
| Drug chamber | |
| Height | 8.2 mm |
| Length* (side surface) | a: 7.6 mm; b: 12 mm, |

TABLE IV-continued

| SPECIFICATIONS OF THE PROTOTYPE | |
|---|---|
| | c: 4.1 mm |
| Volume | 800 $mm^3$ |

According to the capsule design, the distance between the chamber and the head at the other side is about 2-3 mm. If the capsule is erected, the upper head contacts the drug chamber due to its weight. The results of indentation tests (the blue X marks in FIG. 33B) were obtained by the capsule in the air. If the chamber is filled with a viscous drug and the capsule is located in the water, the chamber's stiffness becomes high because the drug chamber becomes a damper and the internal pressure of the drug chamber should be higher than the ambient water pressure. In this case, the shape deformation curve's gradient between the point O and the point A (FIG. 33B) becomes smaller. This initial stiffness prevents the undesired drug release during capsule's locomotion.

The alternative chamber design has two improvements. First, the drug is released via four slits at the corners of the chamber, which allows a natural inflow of the ambient fluid to the chamber after the drug release. Because the chamber's shape is recovered by the inflow, the drug release can be repeated multiple times. Next, the chamber has four slits at its corners, which are towards the space between side linkages. As a result, the waste of the drug in the local polymeric coating mode can be minimized.

A. Analysis

Figures 34A, 34B:
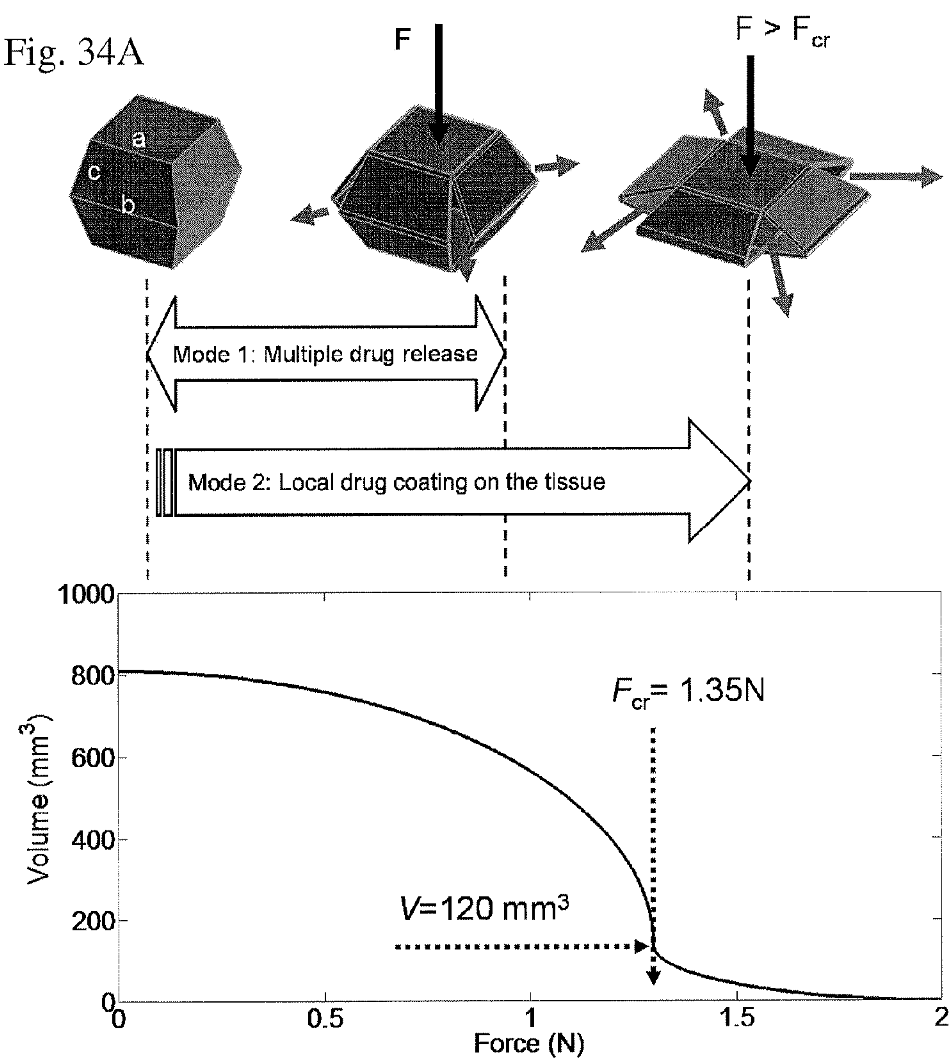
FIG. 34A is a pictorial representation of a Multi-modal drug release mechanism of the present invention; Mode 1: the chamber can maintain its shape under the preloading force weaker than $F_{cr}$. In this range, a small amount of the drug can be pumped out of the chamber, repeatedly; Mode 2: Due to the internal magnetic attraction, the chamber is collapsed by the external magnetic attraction over the critical force. This abrupt collapsing causes a large volume of drug to be released.
FIG. 34B is a graph of Simulation assumptions; the solid line: the volume of the chamber as a function of stimulation (force)

FIG. 34A shows the drug release mechanism using simplified diagrams. The chamber's collapsing is accelerated as it is compressed because the upper internal magnet is attracted by the lower one at a short distance. This critical condition can be used to implement the drug release in two different modes. In this section, the numerical simulation presents the multi-modal drug release in detail. First, the volume change of the drug chamber is equivalent to the volume of the released drug because the drug is incompressible, which is expressed as:

$$\int_{t_i}^{t_f} A(f(t_i))u(t)dt = V(f(t_f)) - V(f(t_i)) \quad (11)$$

where A(f) is the total slit area, V(f) is the volume of the chamber when the applied force is f, $t_i$ and $t_f$ are the initial time and the final time, respectively.

The simulations of multi-modal drug release have two assumptions; 1) Drug chamber volume is a function of the external magnetic attraction; 2) the applied force is a function of time. FIG. 34B shows the drug chamber volume (V) as a function of the pre-loading applied force ($F_{mag}$), which is assumed considering the experimental result (FIG. 33B) and the specification (Table IV). The drug chamber has a critical force ($F_{cr}$) before being fully collapsed. For example, if the applied preload force is 1.35 N, the chamber volume reduces from 800 $mm^3$ to 120 $mm^3$.

Figures 35A, 35B, 35C:
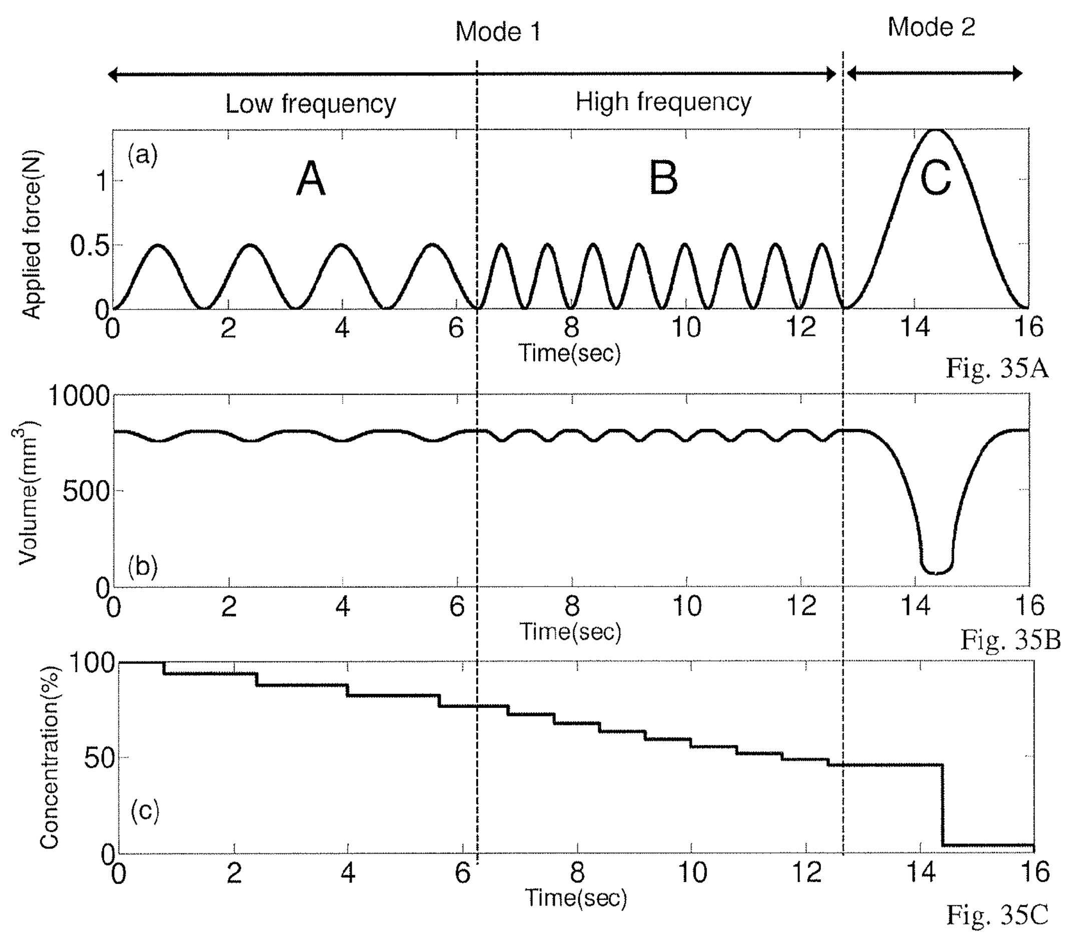
FIGS. 35A-C are simulated multi-modal drug release data by different external magnetic field.

The profile of the stimulation (applied force) is set as in FIGS. 35A-C. A series of weak stimulation in the regions A and B are for small and continuous drug release. Their maximum force (0.5 N) is weaker than the critical force ($F_{cr}$) of FIG. 34B. In the region B, the frequency is doubled, but the magnetic attraction is same as in the region A. The stimulation in the region C is for imparting a local drug coating. The maximum force (1.4 N) is stronger than the critical force.

If the applied force curve at each time (FIG. 35A) and the shape deformation curve (FIG. 34B) are combined, the chamber volume at each time is interpolated as in FIG. 35B. In the part A and B, the drug release is almost continuous. If the frequency of the external magnetic field is high, the chamber volume plot becomes more fluctuated. In the part C, the stimulation induces the full compression of the chamber. At the moment, the drug release speed becomes extremely high. Using such high fluidic force and the volume of the release drug, the drug is coated around the target. As the drug release is repeated, the concentration of the released drug becomes lower because of the inflow of the ambient fluid (see FIG. 35C). Considering the lowering of the concentration, the actual quantity of the released drug per time in A and B are 195 $mm^3$/s and 265 $mm^3$/s, respectively.

I. Experiments

A. Multiple Drug Release

Figures 36A, 36B:
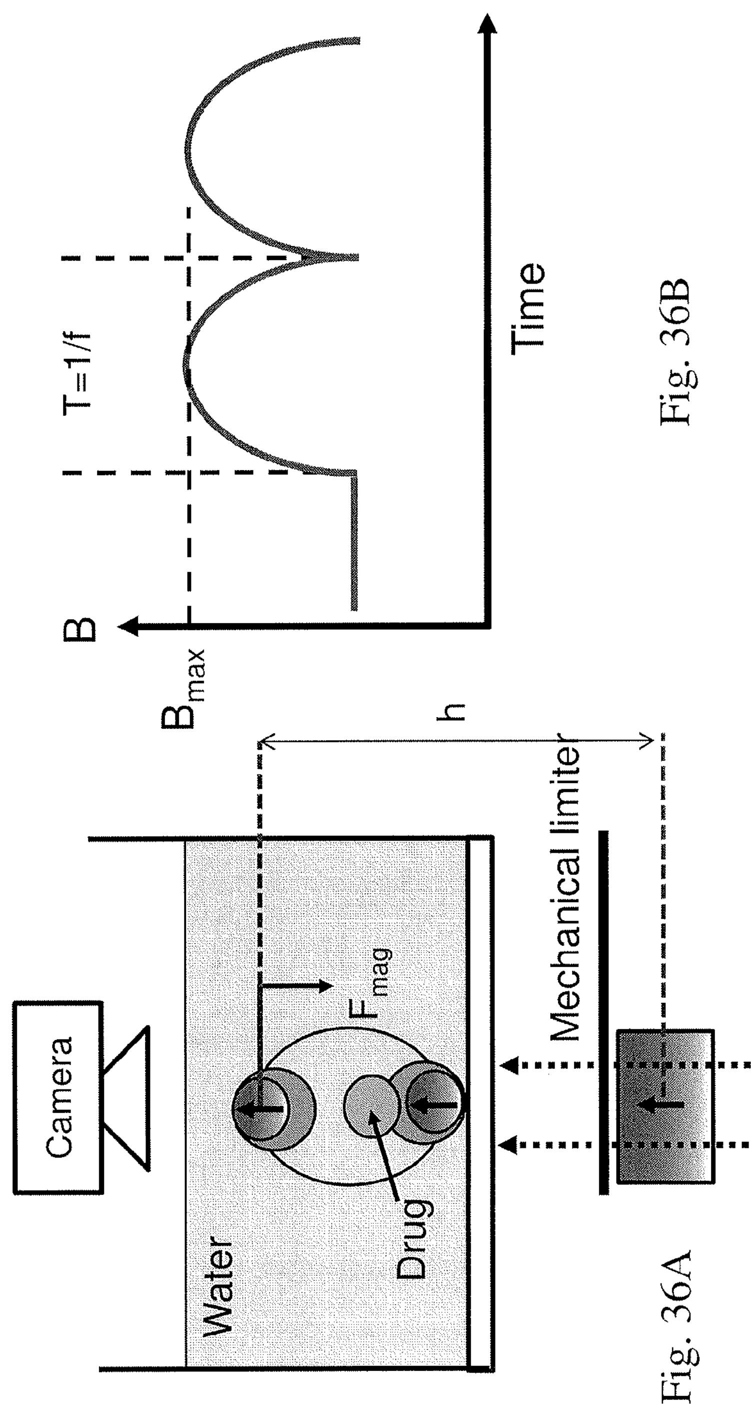
FIG. 36A is a schematic of experimental set-up to evaluate drug release pattern.
FIG. 36B is a graphical representation of variables of the stimulation; $B_{max}$: the maximum magnetic field; f: the frequency.

The performance of the multi-modal drug release was evaluated in experiments. A mixture of water and Methylene-blue was injected into the drug chamber of the capsule, which was then placed in a container filled with water. The images of the released drug and the capsule were taken by a camera above the water container (see FIG. 36A). The magnetic capsule was stimulated by the external magnetic field. The field magnitude (0.01 T<$B_{max}$<0.07 T) and the frequency (0.1 Hz<f<2 Hz) were differently set. The external permanent magnet (cylindrical, diameter 50 mm×length 80 mm, the maximum remanence $B_{r,max}$=1.4 T) was moved manually toward the magnetic capsule until the mechanical limit is reached. The distance (h) between the external magnet and the capsule was measured and the magnetic field was interpolated based on the magnetic field vs. distance curve which was measured by a magnetometer (model 410, Lake Shore). The average frequency was calculated by taken images.

Figure 37A:
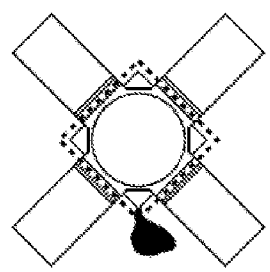
FIGS. 37A-C are photographs of the present invention releasing a drug. The white dotted line means the area of the drug chamber. The arrow means the diffusion direction of the released drug; f=1.6 Hz; $B_{max}$=0.03 T.
Figure 37B:
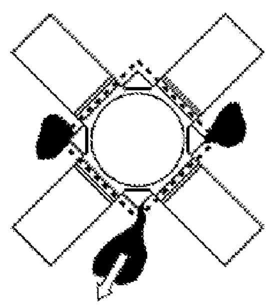
Figure 37C:
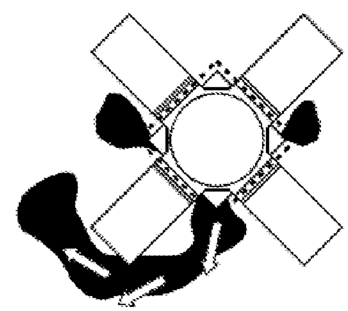
Figure 38:
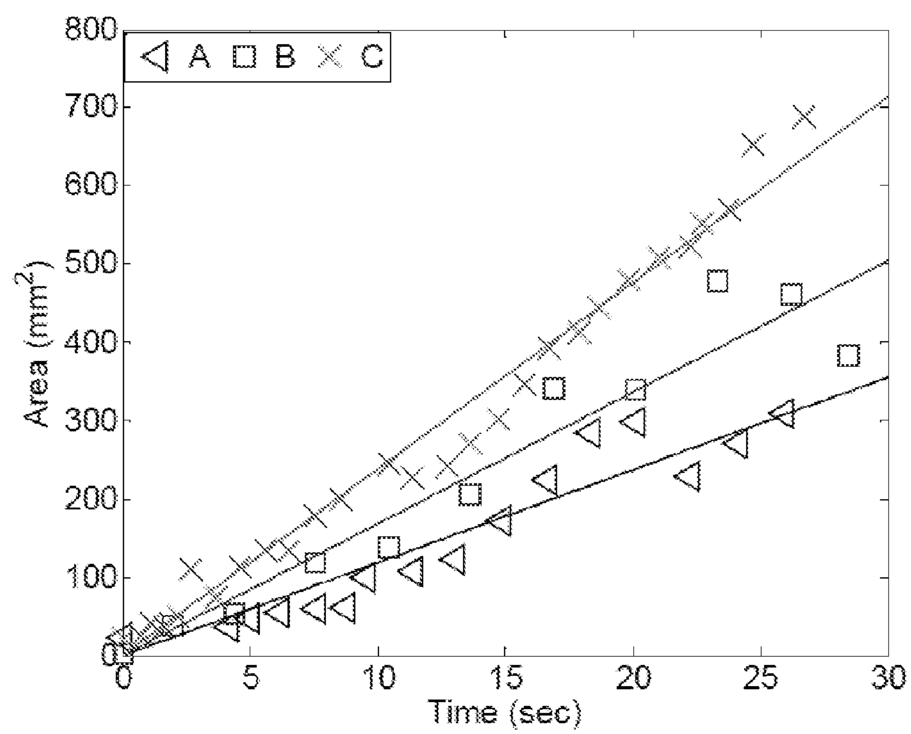
FIG. 38 is a graphical representation of a drug-coated area vs. time; the frequency of the external magnetic field: A: 1.2 Hz; B: 1.6 Hz; C: 2.0 Hz; $B_{max}$=0.03 T.
Figures 39A, 39B, 39C:
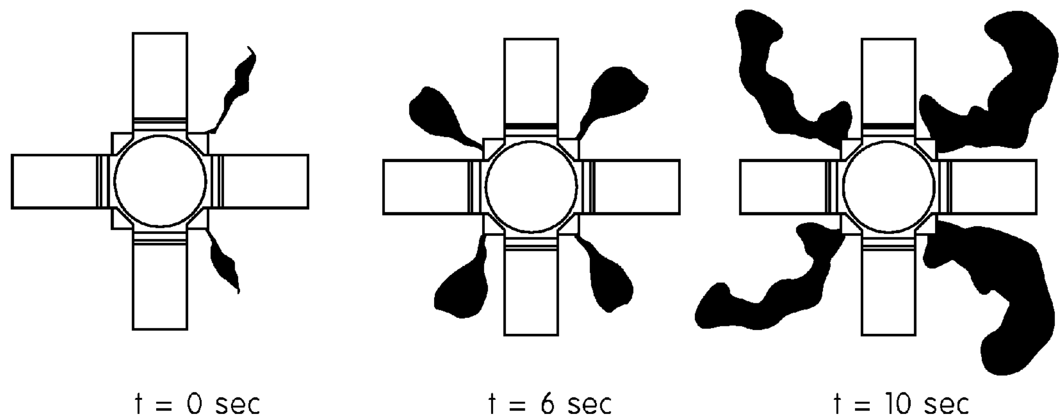
FIGS. 39A-F are top-view photographs of the local polymeric coating demonstration; (a)-(c) Hydro-gel sample $M_1$ where $B_{max}$=0.07 T; (d)-(f) Hydro-gel sample $M_4$ where $B_{max}$=0.07 T.
Figures 39D, 39E, 39F:
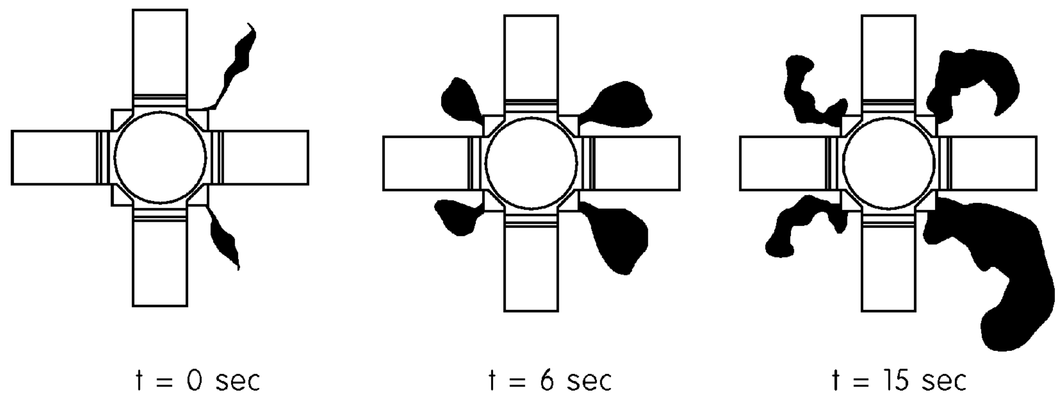

FIGS. 37A-C show some snapshots during multiple drug release. Key observations are as follows:

i) Maximum Magnetic Field:

As simulated in FIGS. 35A-C, the compression of the chamber is controlled by only the maximum magnetic field. The magnetic capsule promptly reacts to the change in the external magnetic field. During both the compression and the relaxation process, delayed response due to the mass inertia of the upper head is not observed. One important point is that the compressed chamber does not necessarily result in a drug release if the injected drug's viscosity is high. The viscous drug is not diffused after being released and then, if the chamber is relaxed, the released drug flows back into the chamber.

ii) Frequency:

Even though the magnetic field governs the compression of the chamber, adjusting the frequency of the external magnetic field is useful to control the drug release. It is extremely difficult to prove this relation directly using experiments because measuring the volume of the released drug in 3-D is not possible. Therefore, the performance of the multiple drug release experiment is evaluated by 2-D image analysis indirectly even though it is affected by the diffusion of the releasing drug. FIG. 38 shows the area coated by the diffusing drug as a function of time. $B_{max}$ was maintained at 0.03 T and the frequency was changed from 1.2 Hz to 2.0 Hz. The plots show the external magnetic field of high frequency induces a fast diffusion of the released drug.

B. Polymeric Drug Coating

Differing from the first mode, in the polymeric drug coating mode, even a highly viscous drug can be released because the abrupt compression of the drug chamber gives a strong fluidic force to the released drug. Considering that most drugs for mucus layer protection are highly viscous, such performance is useful for the application. However, the physical features of the polymeric coating (e.g., coating area, pattern, and distance) are important because the polymeric film should be a protection layer. Therefore, in the next experiments, the effect of the drug viscosity on the polymeric coating was investigated. A mucoadhesive material was used to change the viscosity (see Table V for detailed information of the drug). A total of four hydro-gel samples ($M_1$-$M_4$) with different viscosities were prepared (see Table VI for detailed information of the hydro-gel samples). The pattern and the area of the released drug at the final state are important points. Using the taken images and imaging processing, they were calculated. Table VII shows the coated area of the released drug and the average distance from the center of the capsule to the coating area. For example, in the case of the $M_4$, about 317 $mm^2$ is coated by the polymeric drug, and the average distance is about 8 mm.

TABLE V

MATERIAL PROPERTY OF THE SAMPLE DRUGS

| | |
|---|---|
| Formula | $C_3H_4O_2$ |
| Ratio | Carbopol: 0.3% |
| | Poly-vinyl-pyrrolidone (PVP): 10% |
| | Glycol solution: 0.6% |
| pH | 7.1 |
| Viscosity (Pa · s) | 2.0 at the shear rate of 1 $sec^{-1}$ |
| | 0.1 at the shear rate of 10 $sec^{-1}$ |

TABLE VI

SPECIFICATIONS OF THE HYDRO-GEL SAMPLES

| Material | Mixing ratio (=water:drug) | *Viscosity (Pa s) |
|---|---|---|
| $M_1$ | 2:3 | 0.1-0.01 |
| $M_2$ | 1:2 | 0.1-0.02 |
| $M_3$ | 1:4 | 0.1-0.05 |
| $M_4$ | 1:6 | 0.2-0.10 |

*Shear rate dependent: viscosity at 1.0 $sec^{-1}$ and 10.0 $sec^{-1}$ Viscosity measured by Bohlin meter

TABLE VII

EXPERIMENTAL RESULTS: DRUG-COATED AREA AND AVERAGE DISTANCE

| Material | Viscosity (Pa s) | *Area ($mm^2$) | *Distance (mm) |
|---|---|---|---|
| $M_1$ | 0.1-0.01 | 4050 (±1391) | 33.0 (±14.0) |
| $M_2$ | 0.1-0.02 | 2710 (±1023) | 21.3 (±12.8) |
| $M_3$ | 0.1-0.05 | 1225 (±157) | 13.3 (±9.2) |
| $M_4$ | 0.2-0.10 | 317 (±47) | 7.9 (±5.0) |

*Experiments were conducted three times each

Figure 40C:
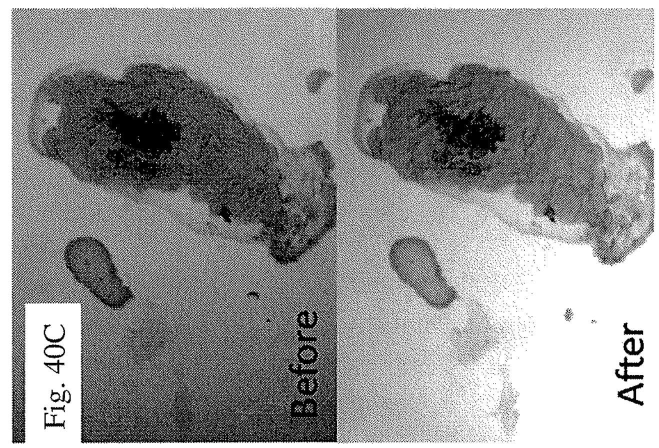
FIGS. 40A-C are optical microscopic images of the HCl exposure experiments.
Figure 40B:
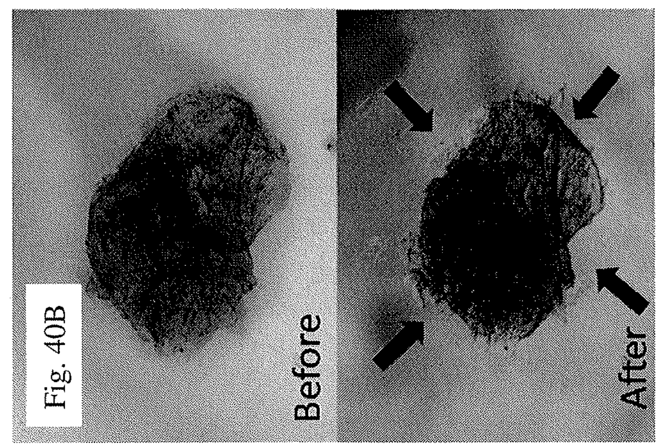
Figure 40A:
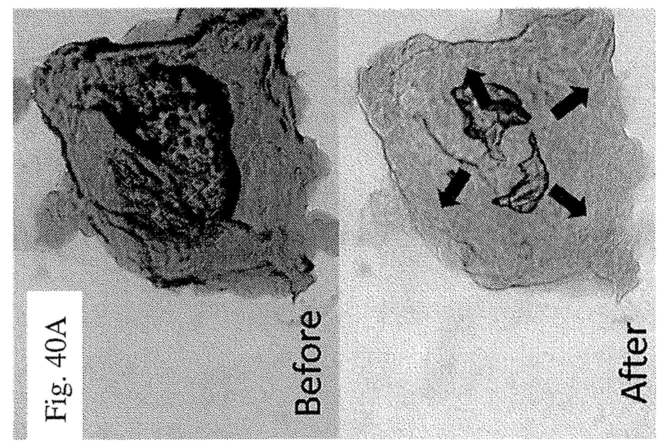

The objective of local polymeric coating is to separate a bleeding tissue or gastric ulcer from an invasive gastric acid, and, finally, to induce the tissue's self-healing. Therefore, the biological response of a cell in the proposed clinical scenario needs to be investigated. An epidermal tissue was picked from a human mouth and dyed with an eosin. The dyed cell was placed on a slide-glass surrounded by a polydimethyl siloxane (PDMS) wall. After dyed, the cell was exposed to HCl. The behavior of the cell was monitored by an inverted optical microscope. FIG. 40A shows the response of the cell without a polymeric coating. The cytoplasm of the cell swells as soon as exposed to HCl because the cytoplasm, which had been dried on the glass-substrate, absorbs the water of HCl solution. Next, if the cell is coated by a hydro-gel, the cytoplasm of the cell shrinks as soon as exposed to HCl (see FIG. 40B). This is because the osmotic pressure makes the water in the cytoplasm move to the HCl solution. Lastly, if the cell-coating material is a non-hydro material like a silicone-oil, there is no interaction between the cell's cytoplasm and the HCl solution (see FIG. 40C). This means that the cell is completely separated from the external HCl solution. The above results show that the drug for the protection of the tissue should be a non-hydro gel.

Discussion

Multi-modal drug release was demonstrated in the experiments, but the designed magnetic capsule also has two potential issues in future clinical applications. First, if the proposed mechanism is implemented in a swallowable capsule (diameter: 10 mm; length: 30 mm, volume: 2300 $mm^3$), the drug chamber occupies about 30% of the total capsule volume because, according to the experiments, the drug chamber volume should be at least 800 $mm^3$ to cover the targeted tissue. Considering that the next generation capsule endoscopes should be equipped with other functional modules such as biopsy and bio-sensors as well, such space assignment might not be practical. As the second issue, in the local polymeric coating mode, the coating drug is formed around the target, not at the target. For example, FIGS. 39A-F shows that four areas are separately formed. These issues would be solved as future works. For example, one possible solution for the first issue is to insert the drug chamber as a separate module and assemble such a module with the main capsule later in the stomach.

I. Conclusion

A magnetically actuated soft capsule endoscope with a multi-modal drug release function is presented. In the first mode, a small amount of drug is continuously released by a series of pulse type magnetic field (0.01-0.03 T and 1.2-2 Hz). The diffusion of the released drug in 2-D images was analyzed and the results show that the drug release can be modulated by the frequency of the external magnetic pulse. This mode will be useful when multiple diseased tissues are observed at different positions or the drug should be released slightly for a long duration. In the second mode, 800 $mm^3$ of drug is released all at once by the external magnetic field of 0.07 T, which induces a stronger magnetic attraction than the capsule's critical force. As a result, a polymeric coating is formed around the capsule. The coated area is dependent on the drug viscosity. In the case of viscous drug (viscosity: 0.2 Pa·s), the coated area is about 317 $mm^2$. Such soft capsules with drug delivery function would be used to treat gastric ulcer or stop the bleeding of stomach tissue in a minimally invasive manner in the future.

3-D Localization Method for a Magnetically Actuated Soft Capsule Endoscope and its Applications The present invention can include a 3-D localization method for a magnetically actuated soft capsule endoscope (MASCE). The proposed localization scheme consists of three steps. First, MASCE is oriented to be coaxially aligned with an external permanent magnet (EPM). Second, MASCE is axially or longitudinal contracted by the enhanced magnetic attraction of the approaching EPM. Third, MASCE recovers its initial shape by the retracting EPM as the magnetic attraction weakens. Combination of the estimated direction in the coaxial alignment step and the estimated distance in the shape deformation (recovery) step provides the position of MASCE in 3-D. It is experimentally shown that the proposed localization method could provide 2.0-3.7 mm of distance error in 3-D. This study also introduces two new applications of the localization method of the present invention. First, based on the trace of contact points between the MASCE and a stomach surface, 3-D geometrical model of a synthetic stomach was reconstructed. Next, the relative tissue compliance at each local contact point in stomach was characterized by measuring the local tissue deformation at each point due to the preloading force. Finally, the characterized relative tissue compliance parameter was mapped onto the geometrical model of the stomach towards future use in disease diagnosis.

Introduction

Currently, magnetic capsule endoscopy is one of the most promising medical technologies for non-invasive diagnosis on the upper gastro-intestinal (GI) tract. [The performance of this capsule's translational movement uses controllable field gradients by an electromagnetic actuation system or changing capsule locomotion dynamics.

Figures 41A, 41B, 41C:
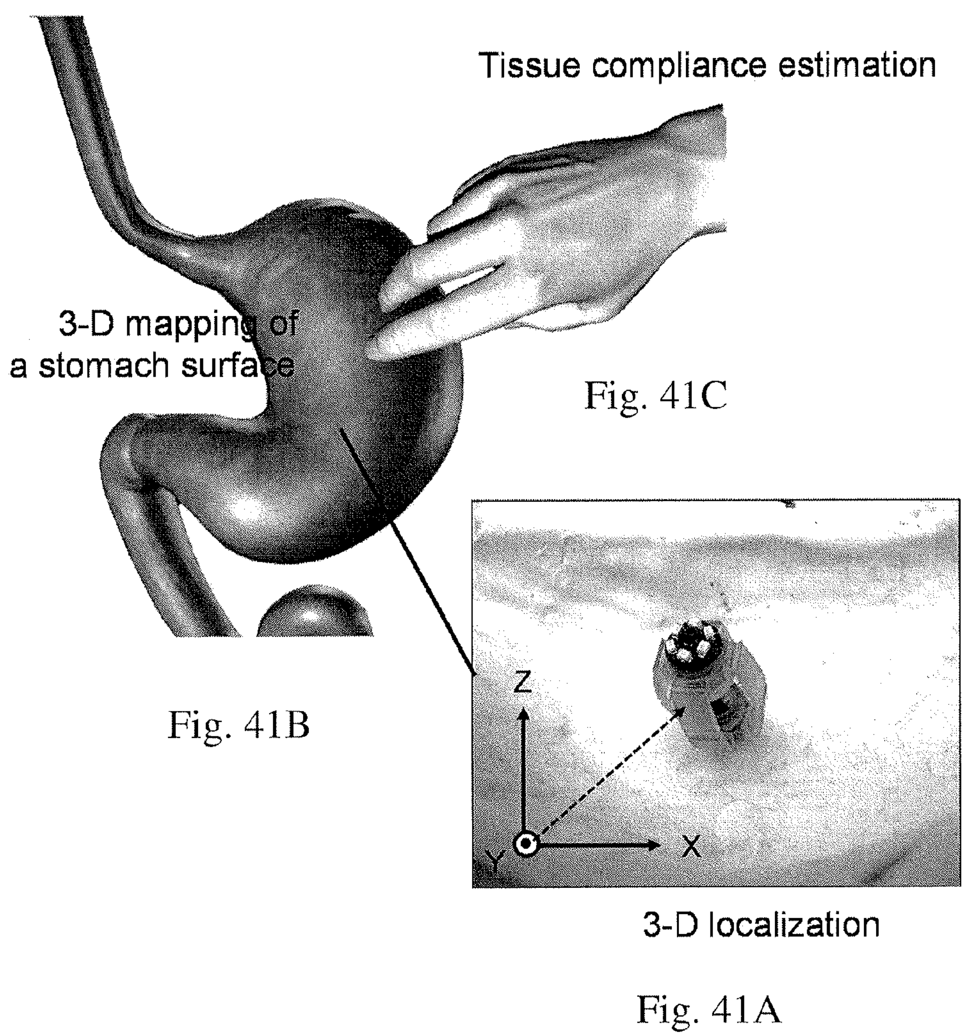
FIGS. 41A-C are illustrates of aspects of the localization method of the present invention, where
Figure 42:
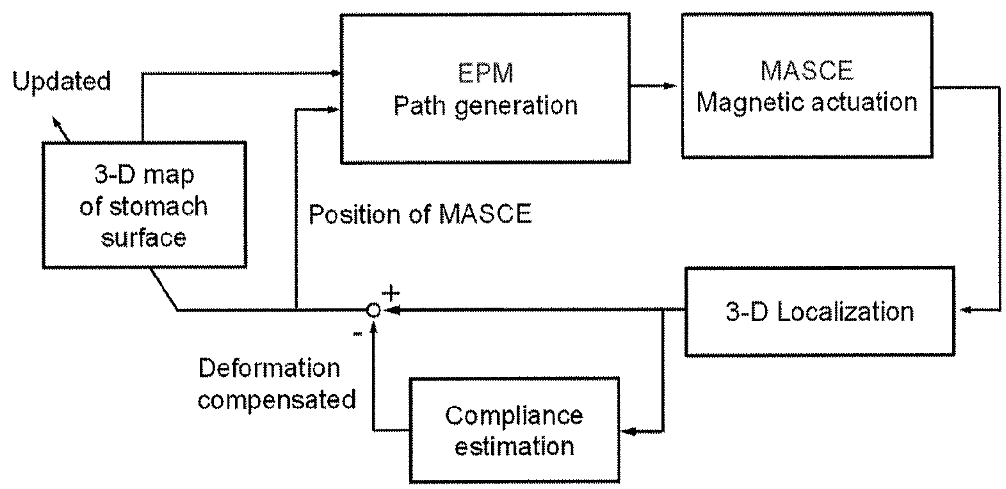
FIG. 42 is a block diagram for operation of MASCE while being moved, localized and used for 3-D tissue compliance estimation and map generation; MASCE is actuated and rolled on the bottom surface of stomach by an external permanent magnet (EPM) in 3-D [14], and localized using the proposed method in this study. Such 3-D localization information is used to measure the local stiffness of stomach by measuring the tissue deformation. Compensate such tissue deformation, EPM's position is controlled and a 3-D map of stomach is created.

As an alternative to existing rigid magnetic capsule endoscopes with only basic locomotion demonstrations, the present invention is a magnetically actuated soft capsule endoscope (MASCE), which moves on the bottom surface of stomach using rolling locomotion. MASCE has two major characteristics. Next, MASCE's axial contraction can be used for an extra degree of freedom actuation and also for advanced therapeutic functions such as targeted or semi-implantable drug release. However, such soft capsule's 3-D localization was a significantly challenging task. Even though various localization methods have been proposed for magnetic capsule endoscopes, they cannot be applied to MASCE and its platform for two reasons. First, external (off-board) hall-effect sensor arrays are not compatible with the MASCE system where an external magnet is used for actuation. Next, using on-board hall-effect sensors is very challenging to measure the external magnetic field accurately because the internal magnetic field, which changes continuously during axial shape deformation of MASCE, infringes significantly with the external magnetic fields. Therefore, a new 3-D localization method for MASCE is required. The key concept is to use the magnetically actuated shape deformation and recovery to localize MASCE between each rolling locomotion cycles. FIGS. 41A-C presents three main contents of this application: 3-D localization method, 3-D mapping of the stomach, and characterization of the local, relative tissue compliance. The process flow diagram is shown in FIG. 42.

As the outline of the application, Section I gives an overview of MASCE and the magnetic actuation platform. Section II presents the 3-D localization method and analysis using shape deformation and recovery. Section III shows experiments to validate the performance of the proposed localization method. Additionally, the application proposes two applications of 3-D localization of MASCE in section V: i) tissue compliance estimation and ii) reconstruction of 3-D map of the stomach. Experimental results of such potential applications and their possible clinical applications are discussed in Sections V and VI, respectively.

I. System Overview

External magnetic actuation system of MASCE is described above. Two internal magnets are embedded at both ends of MASCE, and they are connected by four side linkages with three flexure hinges. MASCE has one mono-axial hall-effect sensor (A1302, Allegro, sensitivity=1.3 mV/G) between two internal magnets as in FIG. 43. The embedded hall-effect sensor measures the magnetic field ($B_{ext}+B_{int}$) in the length direction of MASCE. A small secondary magnet (diameter: 3.2 mm and thickness: 0.8 mm) is located right under the hall-effect sensor. Because the magnetization direction of the secondary magnet is opposite to that of large internal magnets, the maximum measurable magnetic field is extended up to 0.23 T.

The external magnetic actuation platform includes an EPM, which is moved by a motorized 5 degree-of-freedom stage (XYZ-θΦ) under the patient bed. This configuration separates the patient from the workspace of the EPM robotic manipulator, so the unpredicted conflict between the patient and the EPM robotic manipulator can be avoided. MASCE moves on the bottom of stomach surface using rolling motion. On such a slippery stomach surface, its workspace could be limited within a gentle slope (±25°) area. Therefore, the assistive motion of the patient bed is required to expand the limited workspace to the entire surface of the stomach.

II. 3-D Localization Method

Figures 43, 43A, 43B, 43C, 43D:
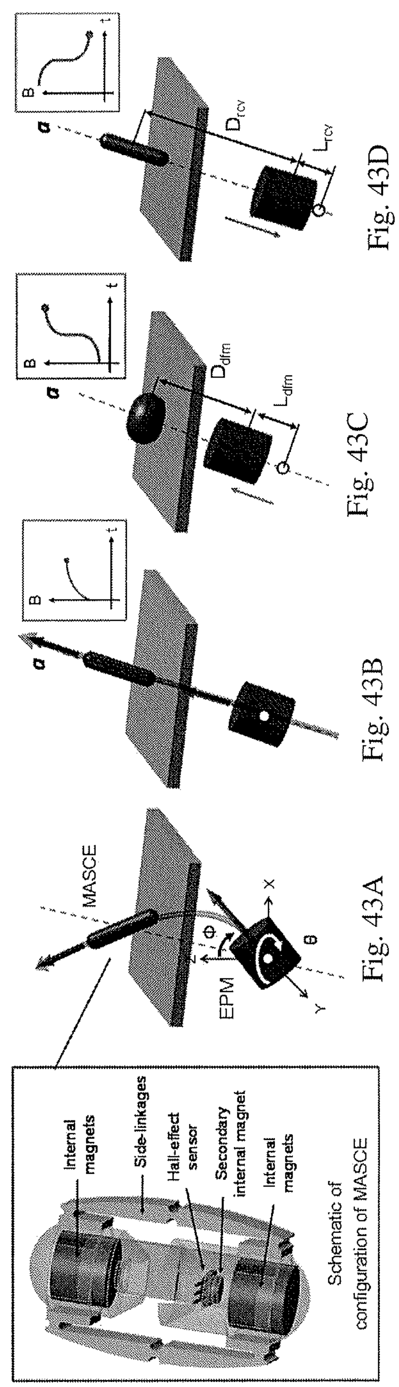
FIG. 43 is a schematic of component in MASCE of the present invention.
FIGS. 43A-D are process steps of 3-D localization estimation method, where

FIGS. 43A-D show the three-step procedure to localize MASCE in 3-D during its rolling locomotion. The first step is the coaxial alignment stage (FIG. 43B). In this step, the magnetization direction of the internal magnets inside MASCE, the magnetization direction of EPM, and the center-to-center line between MASCE and EPM are aligned in one line. The second step is MASCE's shape deformation stage, (FIG. 43C). As EPM approaches MASCE along the EPM's axial direction, MASCE is axially contracted because the magnetic attraction between EPM and the upper internal magnet of MASCE becomes strengthened. The last step is MASCE's shape recovery stage (FIG. 43D). In this step, as EPM becomes further from MASCE, MASCE recovers its initial shape. In this section, the principle and the role of each step for 3-D localization are introduced using experiments and simulations. All these stages are detected by the output of the embedded hall-effect sensor of MASCE shown in FIG. 43.

MASCE is localized twice via an EPM between each rolling locomotion cycles. Because the EPM's position and orientation are known by encoders, if the relative position of MASCE from EPM is estimated, MASCE's position in the absolute coordinate is calculated. Assuming that the relative coordinate is the spherical coordinate as in FIG. 43A, direction of MASCE and the distance between MASCE and EPM are required to localize MASCE. The key equation for 3-D localization of MASCE is:

$$P_{msc}=P_{epm}+(D+L)\vec{\alpha} \tag{12}$$

where $P_{msc}$ and $P_{epm}$ are the 3-D positions of MASCE and EPM, respectively, $\alpha$ is the unit vector in the magnetization direction of EPM after the coaxial alignment stage as shown in FIG. 43B, D is the critical distance between EPM and MASCE for shape deformation or recovery, and L is the displacement of EPM along the coaxial direction as shown in FIGS. 43C-D. In the following subsections, the direction estimation and the distance estimation methods are introduced.

A. Coaxial Alignment

In the coaxial alignment stage, the direction of MASCE from EPM in the spherical coordinate is estimated by orienting EPM in the θ and the Φ directions. When MASCE becomes aligned with EPM in one axis as in FIG. 43B, the output of the embedded hall-effect sensor is maximized. This stage gives the information of vector α, which is defined by:

$$\vec{\alpha}=(\sin\phi_{cx}\cos\theta_{cx}, \sin\phi_{cx}\sin\theta_{cx}, \cos\phi_{cx}) \tag{13}$$

where $\Phi_{cx}$ and $\theta_{cx}$ are the converged angles of EPM during the coaxial alignment stage. In this section, the working principle, the implementation method and the preliminary experimental results are introduced in detail.

Figure 44A:
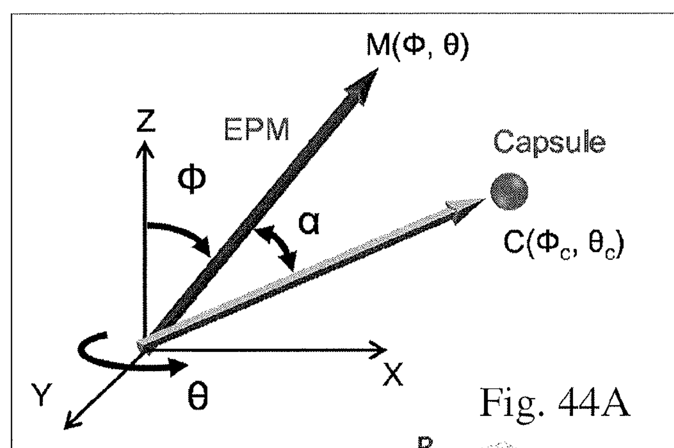
FIG. 44A is a spherical coordinate to calculate the misalignment angle (α); M(Φ,θ): the magnetization direction of the EPM; C: the 3-D position of MASCE; its direction is expressed as ($\Phi_c$, $\theta_c$)

1) Magnetic Field Analysis:

FIG. 44A shows the coordinate to analyze the magnetic field of MASCE in the coaxial alignment stage. Assuming that the position of MASCE is $(x_c, y_c, z_c)$ in Cartesian coordinates, it can be transformed to $(r_c, \Phi_c, \theta_c)$ in spherical coordinates. If the distance $(r_c)$ is assumed constant, the direction of MASCE is presented as $(\Phi_c, \theta_c)$. Assuming that the EPM's magnetization direction is (Φ, θ), the misalignment angle (α) is calculated by equation (14) using the second law of cosine:

$$\cos\alpha = 1-\frac{1}{2}\begin{bmatrix}(\sin\phi_c\cos\theta_c-\sin\phi\cos\theta)^2+\\(\sin\phi_c\sin\theta_c-\sin\phi\sin\theta)^2+(\cos\phi_c-\cos\phi)^2\end{bmatrix} \tag{14}$$

If the EPM is simplified to a single magnetic dipole, the maximum magnetic field of MASCE is presented as $$\max(B(\alpha))=\frac{\mu_0}{4\pi r_c^3}V_{epm}M_{epm}(1+3\cos^2\alpha) \tag{15}$$

where $M_{epm}$ is the EPM magnetization, $V_{epm}$ is the EPM volume, $r_c$ is the distance between EPM and MASCE, and $\mu_0$ is the permeability of the air. As MASCE is automatically aligned with the maximum external magnetic field direction, the external magnetic field in the MASCE's magnetization direction is expressed as Equation (16), which shows that the magnetic field is maximized to have the misalignment angle 0 such that:

$$B_c(\alpha)=\max(B(\alpha))=\frac{\mu_0}{4\pi r_c^3}V_{epm}M_{epm}(1+3\cos^2\alpha) \tag{16}$$

At the global maximum of $B_c(\Phi, \theta)$, two partial derivatives satisfy $$\frac{\partial B_c}{\partial\theta}=0,\ \frac{\partial B_c}{\partial\varphi}=0 \tag{17}$$

which result in two analytical solutions. The first one is that Φ is 0. If EPM is in the vertical direction, the rotation in θ direction is meaningless because EPM is axis-symmetric. However, the first solution is not the desired one because the magnetic field is not actually maximized at this position. The second solution is that Φ and θ are $\Phi_c$ and $\theta_c$, respectively, which means the EPM's final directions are same as the MASCE's directions.

Figure 44B:
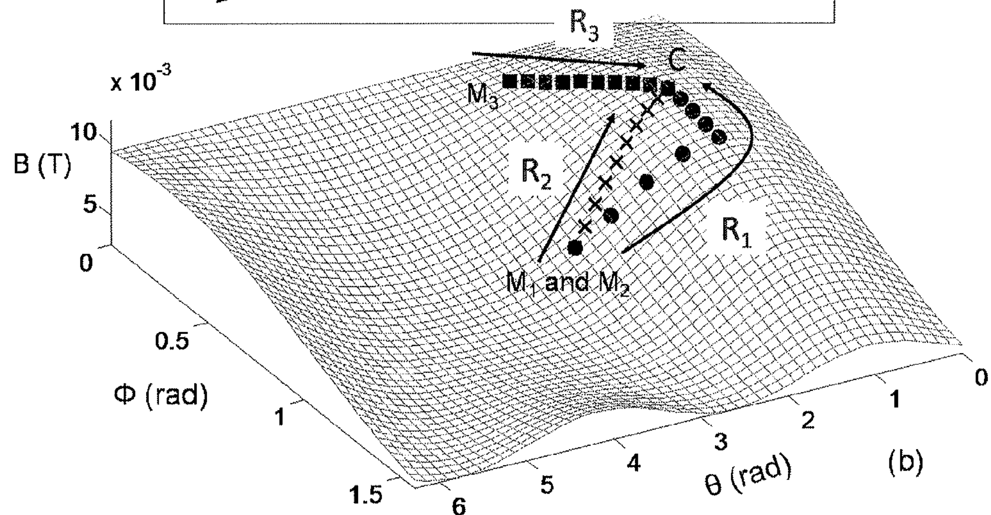
FIG. 44B is a numerical simulation about the convergence of the EPM starting from different initial directions ($M_1$, $M_2$, and $M_3$) to C; $M_1$ and $M_2$: (45°,155°); $M_3$: (10°,120°); C: (30°,60°)

FIG. 44B shows numerical simulations about the coaxial alignment. Assuming that $(\Phi_c, \theta_c)$ is (30°, 60°), $B_c$ was calculated as a function of (Φ, θ) using equations (14) and (16). The three routes of FIG. 44B show that, although their initial points (or the routes) were differently set, they finally converged to the same point $(\Phi_c, \theta_c)$ through the coaxial alignment (compare $R_1$ with $R_3$ or $R_2$ with $R_3$). Especially, the convergence following the route $R_1$ shows that the EPM was orientated in the θ-direction and then in the Φ-direction. In such sequential orientation, the convergences in the θ-direction and in the Φ-direction are decoupled. This is analytically proved by Equation (17). The partial derivatives of $B_c$ about θ become zero only if θ is $\theta_c$. If θ is fixed at $\theta_c$, the partial derivative of $B_c$ about Φ also becomes 0 only where Φ is $\Phi_c$.

Figure 45:
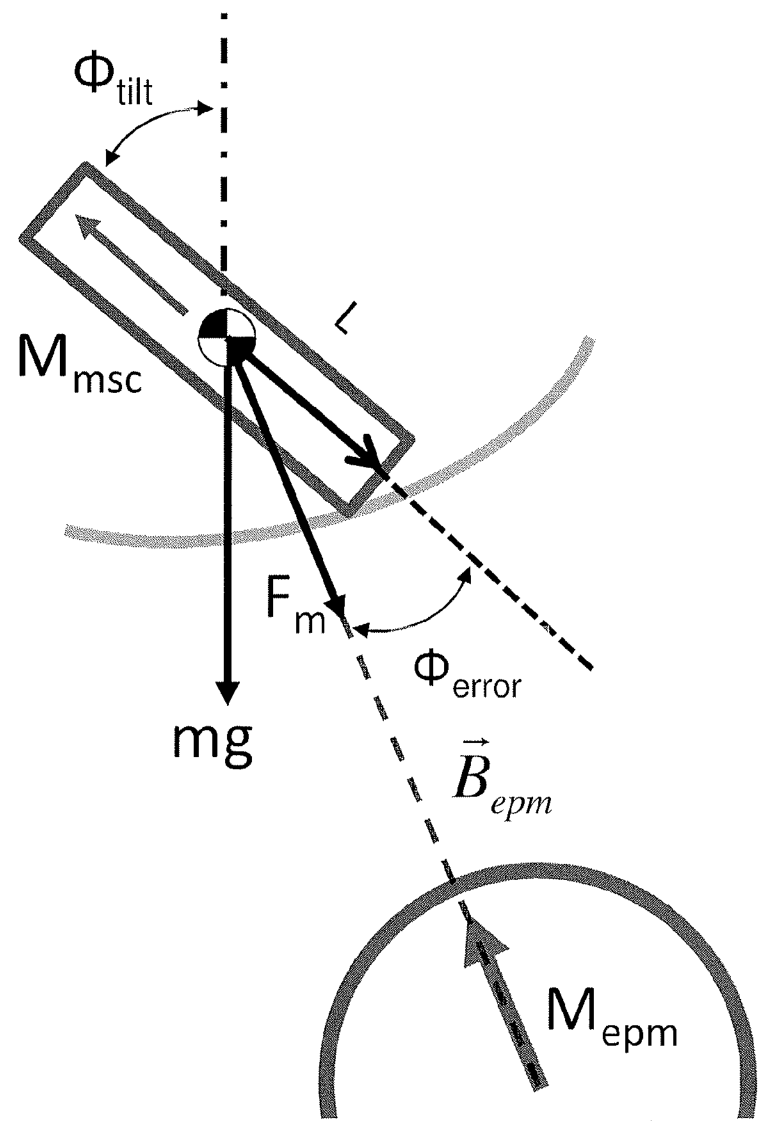
FIG. 45 is a Free-body-diagram of MASCE during coaxial alignment.

2) Modeling and Analysis:

MASCE experiences the external magnetic torque and attraction, and the gravitational torque. FIG. 45 shows a free-body-diagram of MASCE during the coaxial alignment stage. Assuming that MASCE is fixed at the same position and only tilted by magnetic interactions and the gravitational torque, the governing equation is expressed as:

$$T_{net}=(\vec{F}_m\times\vec{l}_{msc})+(m_{msc}\vec{g}\times\vec{l}_{msc})+(V_{msc}\vec{M}_{msc}\times\vec{B}_{epm}) \tag{18}$$

where $m_{msc}$ and $V_{msc}$ are the mass and the volume of the internal magnet, respectively, $l_{msc}$ is the vector in the MASCE's length direction, $M_{msc}$ is the magnetization of the internal magnet, and $B_{epm}$ is the external magnetic field. The MASCE's orientation is fixed if the net torque is 0. The analytical solution of equation (18) is given as $$\sin\phi_{error}=\frac{0.5m_{msc}gl\sin\phi_{tilt}}{|BV_{msc}M_{msc}|+0.5F_ml}\cong\frac{m_{msc}gL\sin\phi_{tilt}}{|2BV_{msc}M_{msc}|} \tag{19}$$

where $\Phi_{tilt}$ and $\Phi_{error}$ are the tilted angle and the misaligned angle of the MASCE, respectively, L is the length of MASCE; the first term of equation (18) is negligible because the magnetic attraction between EPM and MASCE is in the length direction. Equation (198) presents that the effect of gravitational torque in the coaxial alignment stage is limited. For example, if $\Phi_{tilt}$ is 30° and the external magnetic field is 0.05 T, the misalignment angle due to the gravitational torque is only about 1°.

3) Experiments:

The accuracy of direction estimation in the coaxial alignment step was evaluated in preliminary experiments. First, MASCE was mounted on a rubber-coated substrate. Its position $(x_c, y_c, z_c)$ was measured in Cartesian coordinates and transformed to $(r, \Phi_c, \theta_c)$ in spherical coordinates. The cylindrical EPM was fixed at the origin and rotated in the Φ and the θ directions. When the output of hall-effect sensor inside MASCE reached the maximum, the EPM's direction angles ($\Phi_{cx}$ and $\theta_{cx}$) were measured. The final orientation of EPM was compared with $(\Phi_c, \theta_c)$ in Table VIII. The misalignment error, which was calculated using equation (14), was about 5°. The experiments were repeated three times at the same setting to investigate the consistency of the results. The standard deviation of α was ±1.2°.

TABLE VIII

EXPERIMENTAL RESULTS OF THE COAXIAL ALIGNMENT

| MASCE direction | | EPM* direction | Error |
|---|---|---|---|
| $(x_c, y_c, z_c)$ [mm] | $(\Phi_c, \theta_c)$ [°] | $(\Phi_{cx}, \theta_{cx})$ [°] | (α) [°] |
| (5, 1, 52) | (10, 5) | (13, 6) | 5.0 |
| (15, 7, 50) | (30, 15) | (27, 18) | 4.8 |

TABLE VIII-continued

EXPERIMENTAL RESULTS OF THE COAXIAL ALIGNMENT

| MASCE direction | | EPM* direction | Error |
|---|---|---|---|
| $(x_c, y_c, z_c)$ [mm] | $(\Phi_c, \theta_c)$ [°] | $(\Phi_{ex}, \theta_{ex})$ [°] | (α) [°] |
| (15, 12, 46) | (45, 25) | (40, 23) | 3.3 |
| (15, 21, 36) | (57, 33) | (54, 36) | 4.7 |
| (15, 28, 35) | (53, 40) | (62, 42) | 7.0 |
| (24, 31, 33) | (56, 47) | (52, 50) | 5.2 |

*Cylindrical external permanent magnet 50 mm (diameter) × 80 mm (length)

The coaxial alignment should be precise because a small direction error could induce a large localization error as the distance from EPM to MASCE increases. Through experiments, we observed that the geometry of EPM plays an important role to minimize the error. As a cylindrical (or rectangular) magnet has a flat surface on its top, the sensitivity significantly decreases as the EPM becomes more aligned with MASCE. The most preferable geometry of EPM is a spherical magnet. Such shape would have a strong magnetic field in its axial direction. Therefore, in 3-D localization experiments of section IV, a spherical magnet was used.

B. Shape Deformation and Recovery

While coaxial alignment is the process to estimate the direction of MASCE from EPM in spherical coordinates, the shape deformation and recovery of MASCE is the process to estimate the coaxial distance from EPM to MASCE. Due to the internal magnetic attraction, MASCE experiences shape deformation and recovery cycle with hysteresis as in FIG. 46A. If the magnetic attraction between the upper internal magnet of MASCE and EPM exceeds the critical force of shape deformation ($F_{dfm}$), MASCE is abruptly compressed. Also, if the magnetic attraction falls below the critical force ($F_{rcv}$) of shape recovery, MASCE recovers its initial shape abruptly. Shape deformation or recovery of MASCE is detected by the on-board hall-effect sensor because the internal magnetic field dramatically increases (or decreases) during such deformation (or recovery).

The critical distances for shape deformation and recovery ($D_{dfm}$ and $D_{rcv}$) can be expressed as:

$$\frac{F_{dfm}}{M_i V_i} = \frac{dB_{epm}}{dr}\bigg|^{r=D_{dfm}}, \quad \frac{F_{rcv}}{M_i V_i} = \frac{dB_{epm}}{dr}\bigg|^{r=D_{rcv}} \tag{20}$$

where $M_i$ and $V_i$ are the magnetization and the volume of the upper internal magnet, respectively, r is the coaxial direction vector. $D_{dfm}$ and $D_{rcv}$ are governed by the EPM's size and magnetization, and the design (compliance) of MASCE, and plugged into D of Equation (23) to localize MASCE.

Figures 46A, 46B, 46C:
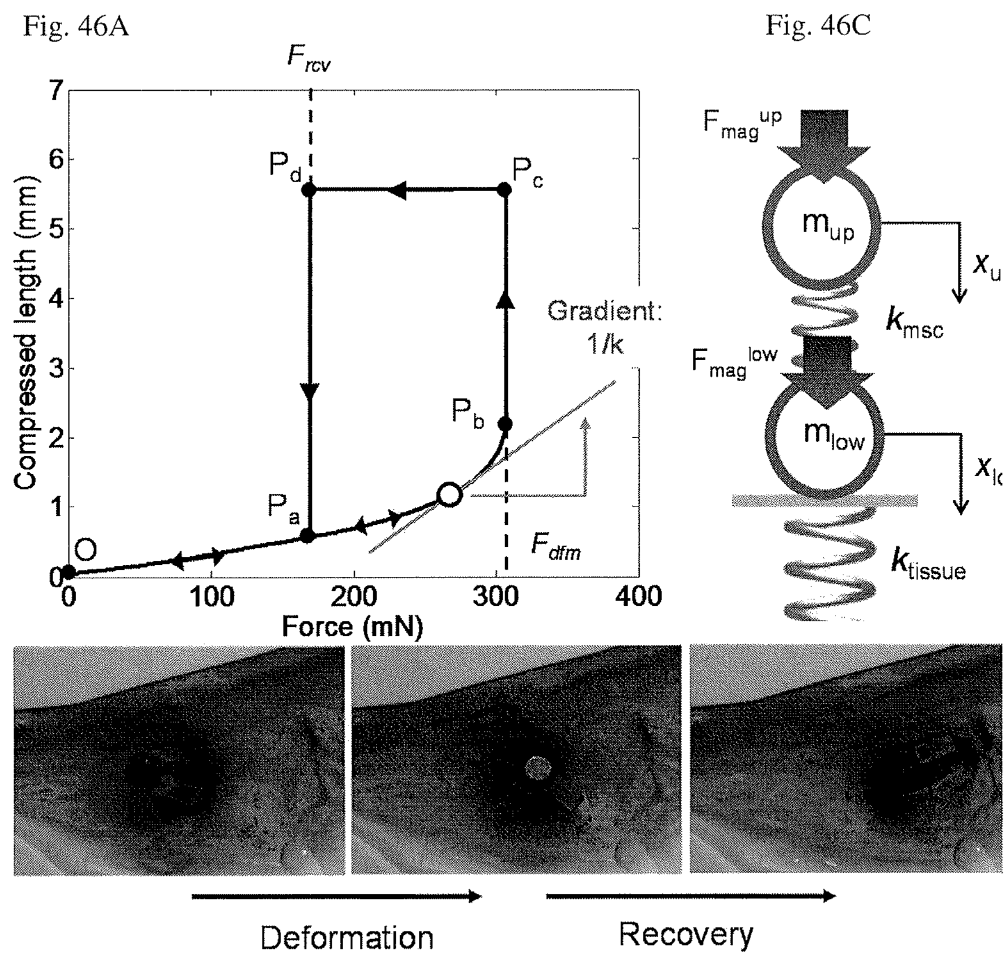
FIG. 46A is an Experimental shape deformation and recovery curves of MASCE as MASCE is compressed by the external magnetic attraction following O-$P_a$-$P_b$-$P_c$. If the external magnetic attraction weakens, the shape is recovered following $P_c$-$P_d$-$P_a$-O. The gradient of the curve gives the compliance of MASCE at each state.
FIG. 46B are photographs of MASCE during the axial contraction and shape recovery while rolling.
FIG. 46C is a serially connected mass-spring system for modeling MASCE's axial deformation on a tissue.

1) Modeling and Analysis:

MASCE on a tissue surface can be modeled as a serially connected mass-spring system as shown in FIG. 46C. Such system's governing equation is expressed as:

$$\begin{bmatrix} F_{mag}^{up} \\ F_{mag}^{low} \end{bmatrix} = \begin{bmatrix} m_{up} & 0 \\ 0 & m_{low} \end{bmatrix} \begin{bmatrix} \ddot{x}_{up} \\ \ddot{x}_{low} \end{bmatrix} + \begin{bmatrix} k_{msc}(x) & -k_{msc}(x) \\ -k_{msc}(x) & k_{msc}(x) + k_{tss} \end{bmatrix} \begin{bmatrix} x_{up} \\ x_{low} \end{bmatrix} \tag{21}$$

where $F_{mag}^{up}$ ($F_{mag}^{low}$) is the external magnetic attraction between EPM and the upper (lower) internal magnet, $k_{msc}$ is the stiffness of MASCE, and $k_{tss}$ is the tissue stiffness.

FIG. 46A and Equation (21) explain all the MASCE's behavior at the shape deformation and recovery moments theoretically. First, during O-$P_a$-$P_b$, $P_c$-$P_d$ and $P_a$-O of FIG. 46A, the mass-acceleration term is negligible because the two masses move slowly. The upper row term of Equation (21) presents that the compression of MASCE ($x_{up}$-$x_{low}$) is governed by $F_{mag}^{up}$. The lower row term of Equation (21) presents that the tissue is deformed by the sum of $F_{mag}^{up}$ and $F_{mag}^{low}$.

Next, during $P_b$-$P_c$ and $P_d$-$P_a$, $k_{msc}$ becomes 0; in FIG. 46A, the gradient at each position presents the compliance ($k^{-1}$) of MASCE. If $F_{mag}^{up}$ becomes $F_{dfm}$, $F_{dfm}$ is totally transferred to the mass-acceleration term of Equation (21). The dominant acceleration term means the upper head of MASCE is abruptly compressed. Also, because $x_{low}$ moves slowly (i.e., slow deformation of the tissue), only $F_{mag}^{low}$ governs the deformation of the tissue. Defining $F_{mag}^{low}$ at the shape deformation moment as $F_{dfm}^{P}$, $F_{dfm}^{P}$ and the recovery force of tissue ($k_{tss}x_{low}$) are in equilibrium. If the tissue is compliant (low $k_{tss}$), the deformation of the tissue is large. At a stiff tissue (high $k_{tss}$), the displacement of the lower head ($x_{low}$) is small. The above interpretation is also valid to $F_{rcv}$ and $F_{rcv}^{P}$ in the shape recovery stage.

The stiffness of MASCE becomes 0 when the increasing (or decreasing) inner magnetic attraction and the recovery force of the deforming side linkages are in equilibrium in the shape deformation (or recovery) stage. Therefore, the tissue stiffness does not affect $F_{dfm}$ and $F_{rcv}$. $D_{dfm}$ and $D_{rcv}$ are also invariant in the same design and the same magnetic specifications of MASCE and EPM. As a result, $F_{dfm}^{P}$ and $F_{rcv}^{P}$ are also consistent as $F_{dfm}$ and $F_{rcv}$, respectively.

2) Robustness Analysis:

MASCE is magnetically actuated on the bottom surface of stomach and localized via EPM between each rolling locomotion steps. However, the entire stomach can be periodically disturbed by patient's breathing (15-20 breaths per minute) and the force disturbance could affect the characteristic shape deformation and recovery behavior. In order to reflect this environmental factor, the robustness of $D_{dfm}$ and $D_{rcv}$ should be investigated. First, the magnetic field of EPM in its magnetization direction is expressed as:

$$B_e(r) = \frac{\mu_0 M_{epm} V_{epm}}{\pi r^3} \tag{22}$$

where r is the distance from EPM and MASCE. Combination of Equations (20) and (22) gives:

$$\frac{F_{dfm} + F_d}{F_{dfm}} = \frac{D_{dfm}^4}{(D_{dfm} + \Delta D_{dfm})^4} \tag{23}$$

where $F_d$ is the force disturbance and $\Delta D_{dfm}$ is the change of $D_{dfm}$. If Equation (23) is normalized, the relation between the disturbance and the change of the shape deformation distance can be given as:

$$\left(1 + \frac{\Delta D_{dfm}}{D_{dfm}}\right)^{-1} = \sqrt[4]{1 + \frac{F_d}{F_{dfm}}} \tag{24}$$

Figure 47:
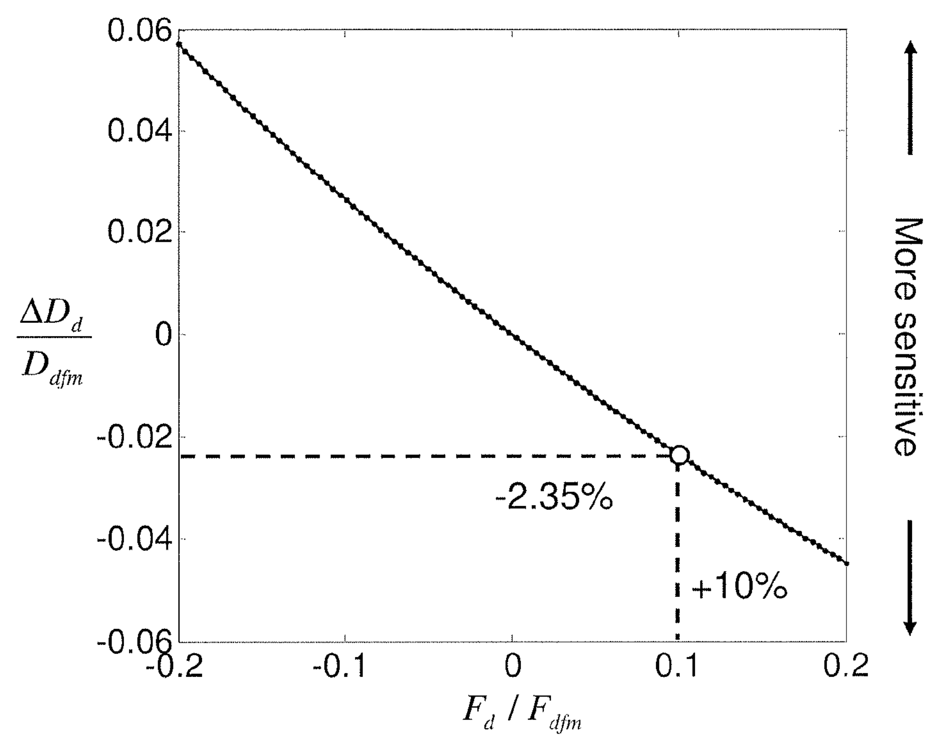
FIG. 47 is a plot of a theoretical analysis about the effect of the force disturbance on the shape deformation (or recovery) distances.

Equation (22) is plotted in FIG. 47. By 10% of the force disturbance, the shape deformation (recovery) distance decreases 2.5%. If $D_{dfm}$ is 300 mm and the force disturbance is 10% of $F_{dfm}$, MASCE is axially contracted when the distance is 292.5 mm.

TABLE IX

| SPECIFICATIONS OF MASCE AND EPM | |
|---|---|
| EPM (External Permanent Magnet) | |
| Shape/Material | Sphere/NdFeB (N42) |
| Diameter | 50 [mm] |
| Surface field | 0.882 [T] |
| Size | |
| Diameter | 15 mm |
| Length (Max./min.) | 33 mm/27 mm |
| Internal magnets of MASCE | |
| Shape/material | Cylindrical/NdFeB (N52) |
| Diameter/thickness | 6.4/6.4 [mm] |
| Surface field | 0.523 [T] |
| Critical force | |
| $F_{dfm}$ ($F_{rcv}$) | 310 (160) [mN] |
| Critical distance | |
| (experimental): $D_{dfm}/D_{rcv}$ | 44.2 (0.24)/57.2 (±0.15) [mm] |

Figure 50A:
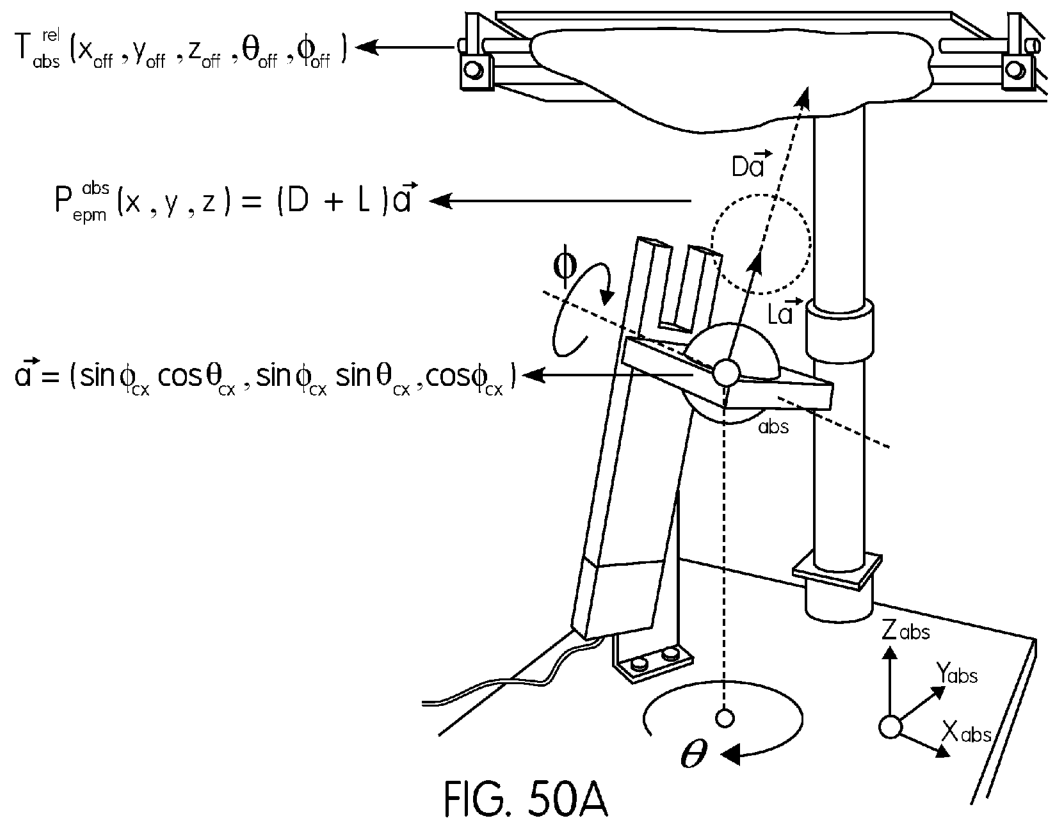
FIGS. 50A-B are photographs of the experimental setup to evaluate the performance of the proposed 3-D localization method, where
Figure 50B:
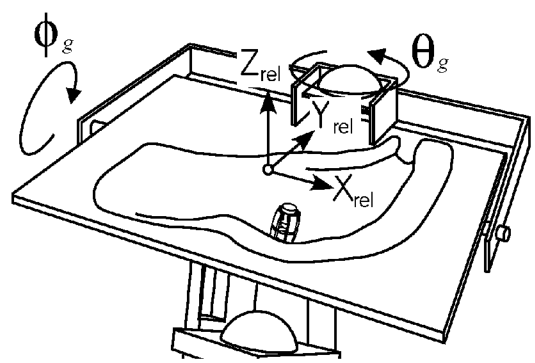

3) Experiments:

Consistency of $D_{dfm}$ and $D_{rcv}$ were experimentally evaluated. Experimental setup is shown in FIGS. 50A-B and described in detail in Section IV. Without touching MASCE, it was aligned with EPM in the coaxial alignment step, and then EPM was vertically moved using the linear actuator. The distance from the center of EPM to the bottom of MASCE was measured when MASCE was abruptly compressed and recovered.

Table IX shows the summarized specifications of the internal magnets of MASCE, EPM and the experimental critical distances. The important feature of this measurement is consistency of $D_{dfm}$ and $D_{rcv}$. The standard deviations of $D_{dfm}$ and $D_{rcv}$ during ten times of measurements were only 0.15 mm and 0.24 mm, respectively. This consistency shows that the distance estimation using the empirical shape deformation (recovery) distance is reliable. We also measured $D_{dfm}$ and $D_{rcv}$ of a MASCE on a compliant substrate (e.g., silicone rubber or polyurethane) or changed the approaching speed of EPM to observe the effect of substrate compliance or the dynamic condition, respectively. However, the results were the same as the results on a rigid substrate, which are consistent with the expectations in modeling.

As shown in Table IX, $D_{dfm}$ and $D_{rcv}$ are relatively short: 44.2 mm and 57.2 mm, respectively. In clinical applications, these distances should be longer than 300 mm for capsule endoscopy of obese patients. One way to increase $D_{dfm}$ and $D_{rcv}$ is making MASCE more compliant, so that it can experience the shape deformation and recovery at lower external magnetic field gradients. The second way is to use a larger EPM with a stronger magnetization. Analytical magnetic model shows that $D_{dfm}$ and $D_{rcv}$ can be extended to about 300 mm if the diameter of EPM ($M_{epm}=1.1\times10^6$ A/m) is 300 mm and $F_{dfm}$ decreases by 50%.

C. Compatibility with Rolling Locomotion

In general, the remote control of MASCE consists of three steps. First, it is localized using the proposed method. Next, considering its current and target positions, the path of EPM is planned. Finally, using translation and rotation of EPM, it is navigated to the desired position. In this section, rolling locomotion and 3-D localization are executed step-by-step in simulations. FIGS. 48A-F shows the captured images of the simulations in sequence. The C dots and the G dots on the top surface of the cube mean the localized position and the goal position of MASCE, respectively. The lines present the position and the magnetization direction of EPM.

First, the initial position of MASCE is $C_0$ and EPM is operated under MASCE. Assuming that the goal position of MASCE is $G_1$, EPM translates towards $G_1$ while being rotated (see FIG. 48A). As soon as EPM reaches $G_1$, the coaxial alignment process starts. EPM is rotated in the θ-direction first (see FIG. 48B) and then in the Φ direction (see FIG. 48C). After the coaxial alignment stage, EPM is moved along the coaxial direction and MASCE is localized using $D_{dfm}$ and $D_{rcv}$ (see FIG. 48C). At this stage, the exact position of $C_1$ is calculated. The next step is divided into two. If MASCE tracks EPM very well, MASCE and EPM's XY-positions are aligned before the next rolling locomotion (see FIG. 48D). After the XY alignment, EPM moves towards the next goal $G_2$ while being rotated, again (see FIG. 48E). However, if the tracking error of MASCE is significant, it means that MASCE is actuated toward a slope. In this case, right after the coaxial alignment, EPM is moved backwards to locate MASCE within the desired workspace again (see FIG. 48F).

Figures 48A, 48B, 48C, 48D, 48E, 48F:
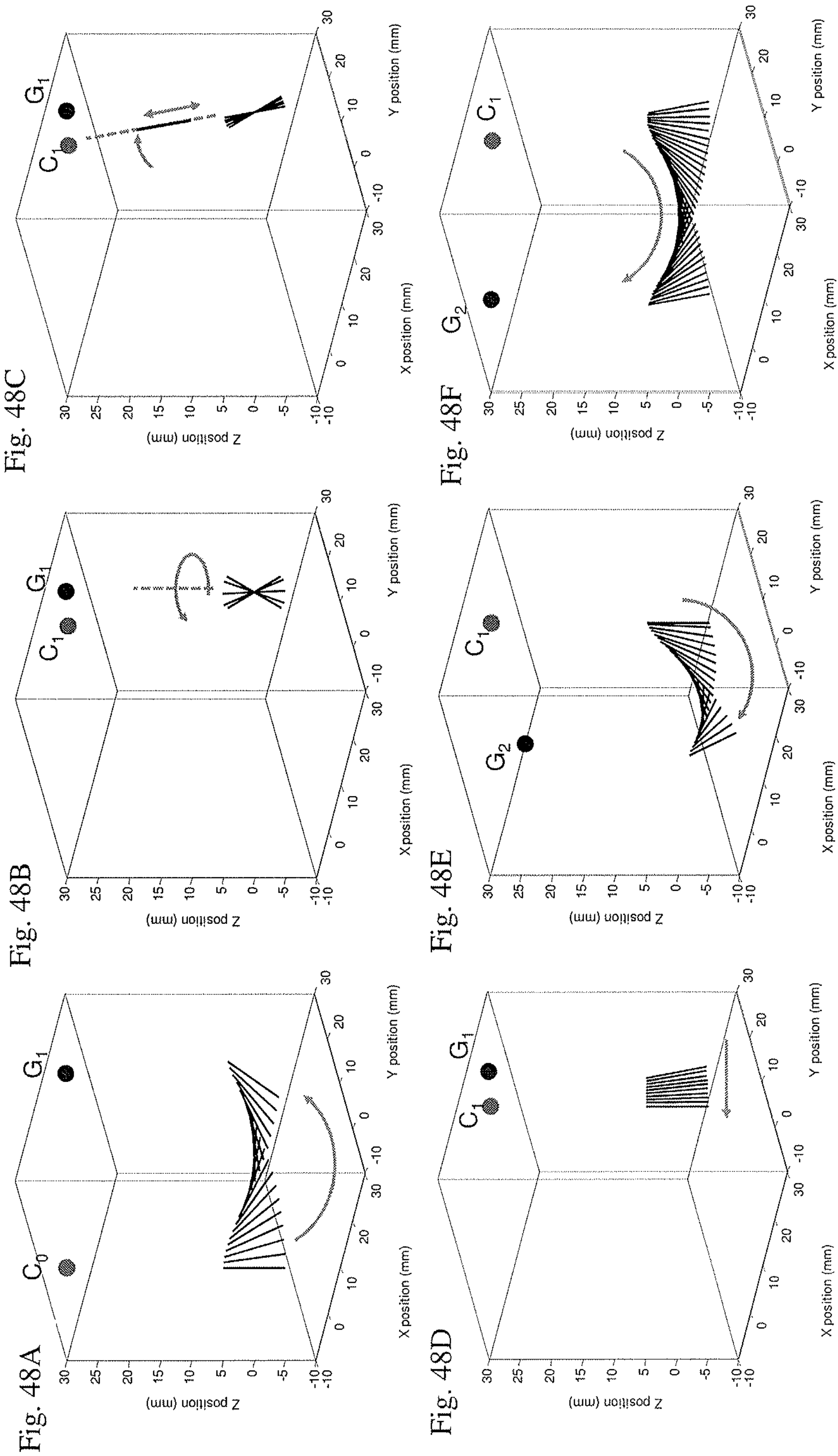
FIGS. 48A-F are examples of simulated sequential execution of rolling locomotion and 3-D localization, where
Figures 49A, 49B:
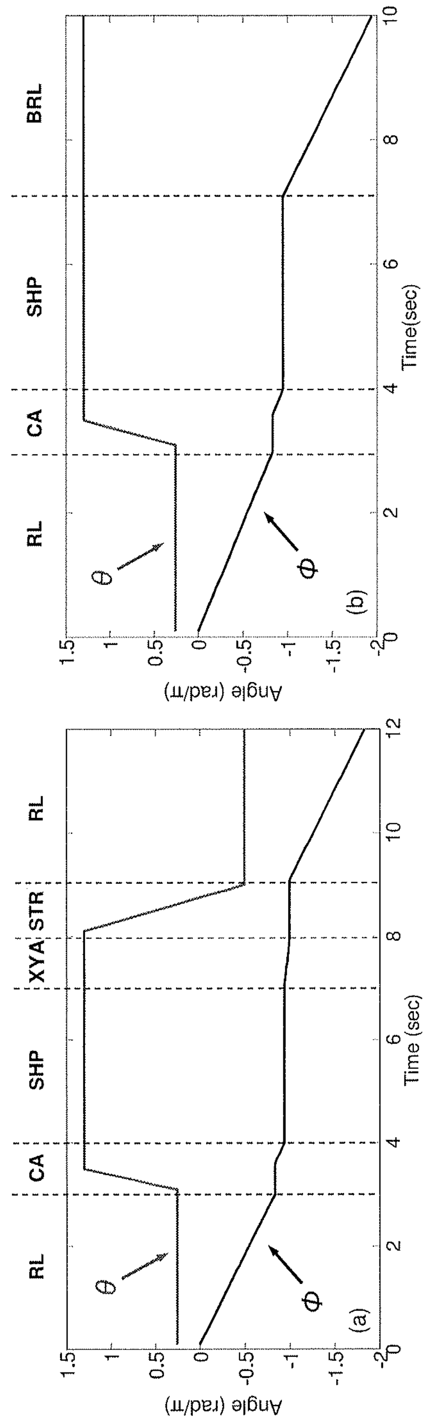
FIGS. 49A-B are simulated EPM's θ and Φ during the first rolling locomotion, 3-D localization, steering and the second rolling locomotion, where

FIG. 49A shows EPM's Φ and θ during rolling locomotion, 3-D localization, XY-alignment, and steering. The description of each stage is as follows:

i) Rolling Locomotion (RL):

θ is constant because it is to steer EPM in the XY-plane. Only Φ changes for rolling motion (see EPM's behavior in FIG. 48A).

ii) Coaxial Alignment (CA):

Basically, the coaxial alignment can start anytime except for Φ=0 during rolling motion. This is because, when Φ is 0, the gradients about Φ and θ become 0 (see section III.A for detailed information). Normally, the coaxial alignment starts when EPM is tilted 20°-30° about the horizontal surface. EPM is aligned with MASCE by rotation in the θ direction first, and then in the Φ direction.

iii) Shape Deformation and Recovery of MASCE (SHP):

After coaxial alignment, EPM is moved along the coaxial direction and MASCE is deformed and recovered. Both Φ and θ do not change during this stage. Only EPM moves back and forth in its magnetization direction iv) XY Alignment (XYA):

After 3-D localization of MASCE, EPM's position is aligned with MASCE's center in the XY plane. Φ slightly changes during this alignment.

v) Steering (STR):

Only EPM's θ changes towards the next goal ($G_2$) of MASCE. While EPM is rotated in the θ-direction, Φ is 0. After steering, the second rolling locomotion starts.

vi) Backward Rolling Locomotion (BRL):

FIG. 48B shows that (after the 3-D localization) EPM moves backwards in order to locate MASCE in the workspace. θ is constant and only Φ changes for the rolling motion of EPM.

III. Experiments

A. Experimental Setup and Procedure

In this section, experimental results are introduced to evaluate the accuracy of the proposed 3-D localization method. FIGS. 50A-B shows the experimental setup, which consists of two parts. First, the lower part is for manipulation of EPM. The spherical EPM is rotated about two axes (θ and Φ) for the coaxial alignment and moved in the coaxial direction ($\alpha$) by a linear actuator in shape deformation and recovery steps (see the movement of EPM in FIG. 48B-C). The displacement of EPM moved by the linear actuator is fed into a data acquisition board (National Instruments, PCIe-6321).

Next, the upper part consists of a substrate with a silicone rubber stomach model, a substrate holder, and a webcam. The substrate can be moved in three directions ($X_{abs}$, $Y_{abs}$, $Z_{abs}$) and rotated about two axes ($\Phi_s$, $\theta_s$). Because the substrate's position and orientation are differently set by changing five variables ($x_{off}$, $y_{off}$, $z_{off}$, $\Phi_{off}$, $\theta_{off}$), even though EPM is fixed at the origin ($O_{abs}$) during the coaxial alignment step, the relative position of MASCE on the substrate can be differently set. Thus, Equation (23) is modified to:

$$P_{msc}^{rel}=T_{abs}^{rel}\cdot(D+L)\vec{\alpha} \qquad (25)$$

$T_{abs}^{rel}$ is the coordinate transformation matrix (4×4) between absolute coordinates and relative coordinates, D equals to $D_{dfm}$ or $D_{rcv}$, which are given in Table IX, L is the approaching (or retracting) distance of EPM in the coaxial direction during shape deformation and recovery, which is given by the linear actuator. Equation (25) shows that the absolute position of MASCE is transformed to the relative position on the substrate (compare ($X_{rel}$, $Y_{rel}$, $Z_{rel}$) and ($X_{abs}$, $Y_{abs}$, $Z_{abs}$) in FIGS. 50A-B).

The prototype and the CAD model of MASCE are shown in FIG. 41A and FIG. 43, respectively. The output of the hall-effect sensor is fed into the same data acquisition board, which is used for measuring the displacement of the linear actuator. By measuring the magnetic field and the displacement of EPM simultaneously, accurate $L_{dfm}$ and $L_{rcv}$ values are measured during shape deformation and recovery steps, respectively. Nickel-chrome wires with a diameter of 70 μm were used to provide power to the hall-effect sensor and to measure the output. Because it is flexible and tough, the error due to the wire tension was negligible during the experiments.

TABLE X

| EXPERIMENT LOCALIZATION ERROR | |
|---|---|
| Using shape deformation: | |
| Min./Max. error | 3.1 [mm]/5.0 [mm] |
| Average error | 3.7 ± 1.8 [mm] |
| Using shape recovery: | |
| Min./Max. error | 1.5 [mm]/2.6 [mm] |
| Average error | 2.0 ± 1.5 [mm] |

B. Flat Substrate Experiments

First, the proposed 3-D localization method was evaluated on a flat, smooth and rigid acrylic substrate. Instead of the rubber-made stomach model, a substrate with 9 markers was mounted on the setup. MASCE prototype was located at nine different positions on the substrate. The coaxial alignment step was executed manually looking at the sensor output, which was displayed in a monitor because $\Phi$ and $\theta$ should be adjusted accordingly. MASCE's shape deformation and recovery were executed using the linear actuator. During the experiments, the hall-effect sensor's output and the displacement of EPM were measured using the same data acquisition board. After experiments, the displacement ($L_{dfm}$ or $L_{rcv}$) of EPM was read in the measured data considering the sensor output. As described in FIGS. 43C and 43D, the hall-effect sensor output abruptly increases or decreases at the shape deformation and the recovery moments. The experiments were repeated multiple times at each position to evaluate the standard deviation of the error.

Figure 51A:
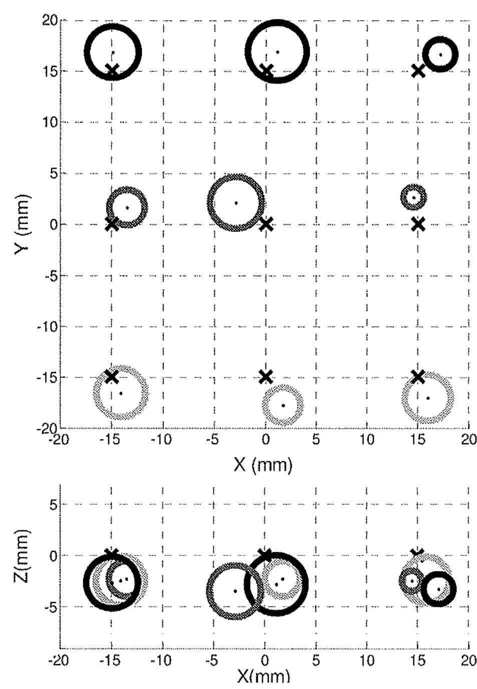
FIGS. 51A-B illustrate results of 3-D localization experiments on an acrylic substrate. Comparison of the real positions and the estimated positions, where FIG. 51A are Shape deformation ($D_{dfm}$)-based localizations; the upper row: XY plane view; the lower row: XZ plane view.
Figure 51B:
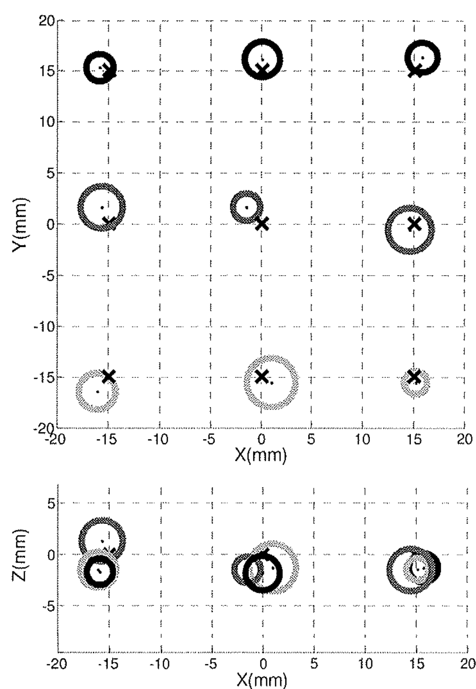

FIGS. 51A and 51B show the localized MASCE using $D_{dfm}$ and $D_{rcv}$, respectively. The 'X' marks and the 'O' marks represent the real and estimated positions of MASCE, respectively. The diameter of the circles means the standard deviation of the position error at each position, which presents the consistency of the precision. The results are summarized in Table X. The average error range is 2.0-3.7 mm.

In Table X and FIG. 51B, the shape recovery-based measured positions present a smaller error than the shape deformation-based ones. Experimental observations explain this trend. First, MASCE is more precisely aligned with the external magnetic field after the axial contraction because the magnetic torque becomes stronger as MASCE is more compressed. Next, the acrylic substrate is slightly deflected by the preloading force. Because $F_{dfm}^{P}$ and $F_{rcv}^{P}$ are 1.57 N and 0.64 N, respectively, the substrate is more deflected in the shape deformation stage than in the shape recovery stage.

The time duration used for MASCE's coaxial alignment, shape deformation and recovery in each experiment was about 1 minute. The coaxial alignment was manually performed and EPM was slowly (1 mm/s) moved along the co-axis. If the coaxial alignment is automatically executed by a motorized setup and EPM is operated fast in the future, the time duration for executing 3-D localization would be reduced significantly. The computational time for Equation (25) is less than 1 sec in MATLAB.

C. Stomach Model Experiments

The second set of experiments was conducted using a synthetic stomach model. The synthetic stomach model is made of silicone rubber (Dow Corning, HS II), so the bottom surface of the model is deformed by the external magnetic attraction. This is similar to the tissue deformation and the organ rearrangement in the human abdomen.

Figure 52:
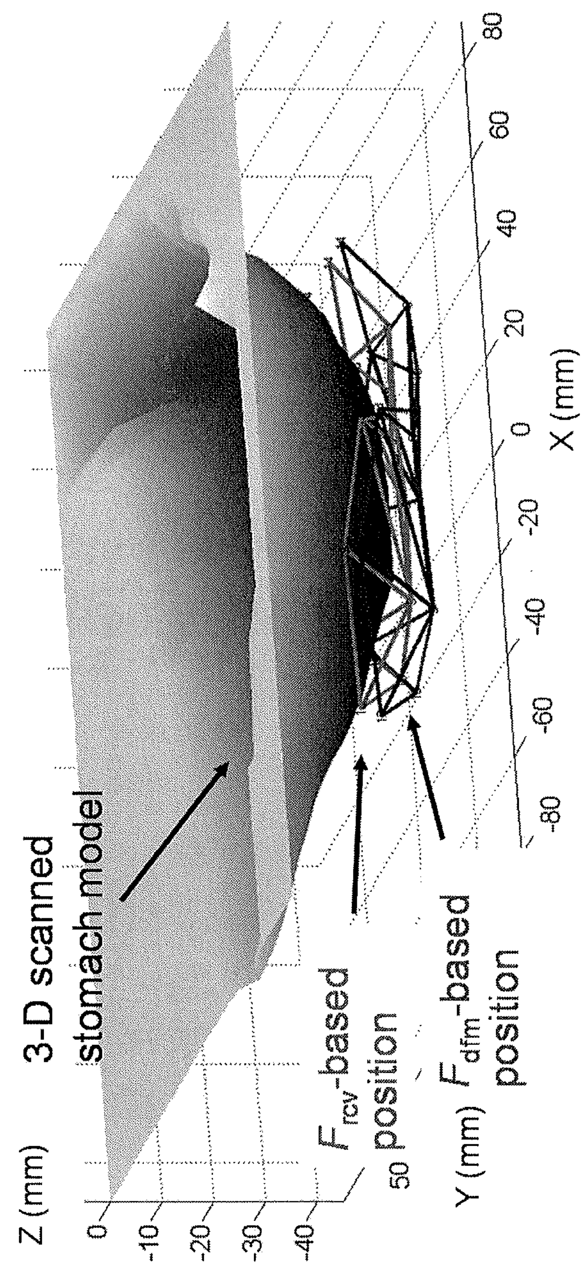
FIG. 52 are results of 3-D localization experiments on a silicone rubber stomach model. The $F_{rcv}^{P}$-based position points and the $F_{dfm}^{P}$-based position points present the localized MASCE using shape deformation and recovery, respectively.

First, the 3-D geometry of the stomach model was measured. Using a probe and a substrate with (XY) grid-hole patterns, the depth (Z) of synthetic stomach model at each grid was manually scanned. FIG. 52 shows the stomach modeling from the 3-D scanned data. Next, MASCE was located at 16 different positions of the rubber-made stomach model and localized using the proposed method. As shown in FIG. 52, the estimated contact points are lower than the actual surface of the 3-D model. Due to the deformation of the rubber-made stomach model, the position difference between the 3-D scanned stomach model and the localized contact points are larger than the error of the flat substrate experiments. FIG. 52 also shows two datasets, the shape deformation-based localization and the shape recovery-based localization. Because $F_{rcv}$ is smaller than $F_{dfm}$, the stomach model is less deformed by MASCE at the shape recovery moment.

IV. 3-D Mapping and Compliance Characterization

A. Tissue Compliance Estimation

MASCE is shown to preload and deform the tissue surface during 3-D localization using the external magnetic attraction. As introduced in section III.B, the compliance of the tissue would be measured using the displacement of the tissue due to MASCE's preloading force ($F_{dfm}^{P}$ and $F_{rcv}^{P}$). A procedure to measure the relative tissue stiffness quantitatively is a new clinically useful elastography technique to diagnose cancerous areas inside GI tract.

Figure 53A:
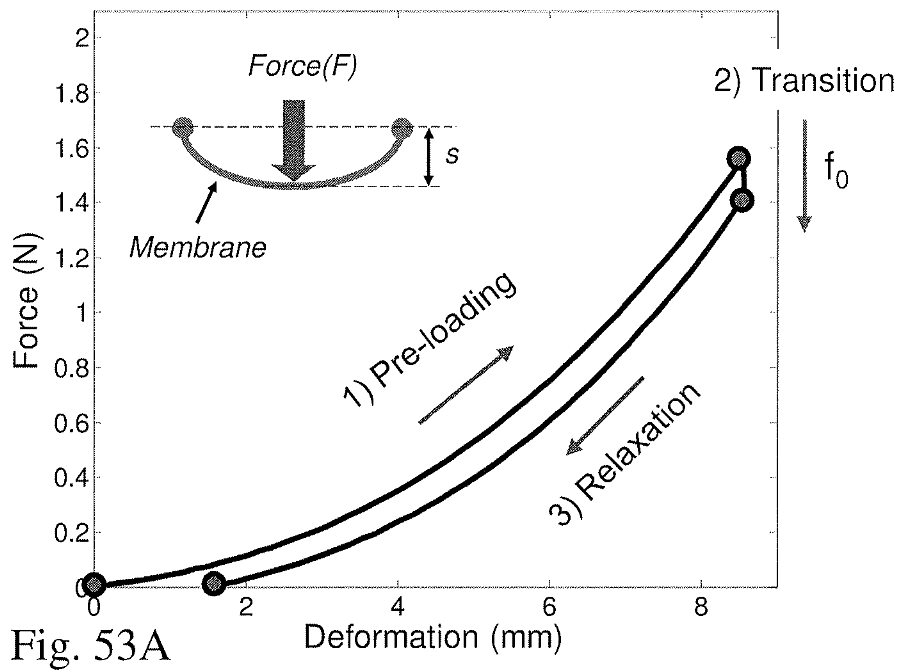
FIG. 53A is a Force-deformation curve of the sample A investigated by an indentation setup.

The tissue deformation (recovery) curve is approximated by a simple polynomial function. To decide the order of the polynomial function, the empirical relation between the indentation depth of a deformable membrane and the preloading force of the spherical indenter was investigated. Three membrane samples made of silicone rubber (HS II, Dow Corning) were prepared and indented. FIG. 53A shows the experimental result of sample A. The curve is divided into three stages: 1) preloading stage, 2) transition stage, and 3) relaxation stage. In the preloading stage, the force (F) can be approximately expressed as a quadratic form of the indentation depth (s) as:

$$F_1 = k^* s^2 \tag{26}$$

where k* is the effective stiffness coefficient at the contact point and s is the displacement of the tissue. In the transition stage, the membrane experiences a stress relaxation. Even though the indentation depth of the membrane does not change, the actual normal force decreases because the stress of membrane is slowly relaxed inside the membrane. This is a common feature of a viscoelastic material. The magnitude of the stress reduction ($f_0$) depends on the transition time. As the transition time becomes longer, $f_0$ becomes larger. In the relaxation stage, the force is expressed as a quadratic form of the indentation depth again, which is given by:

$$F_3 = k^* s^2 - f_0 \tag{27}$$

Here, the translational displacement ($f_0$) between $F_1$ and $F_3$ is due to the stress relaxation in the transition stage.

If the tissue deformations are respectively $s_{dfm}$ and $s_{rcv}$ when MASCE is axially contracted and relaxed, $s_{rcv}$ and k* can be given by:

$$s_{rcv} = \frac{\Delta s}{\sqrt{F_{dfm}^{p} / (F_{rcv}^{p} + f_0)} - 1} \tag{28}$$

$$k^* = \frac{F_{rcv} + f_0}{s_{rcv}^2} \tag{29}$$

where Δs is the difference between $s_{dfm}$ and $s_{rcv}$. These equations show that, if $F_{dfm}^{P}$, $F_{rcv}^{P}$, c, and Δs are known, it is possible to estimate not only the deformation of the tissue at the two moments but also the effective stiffness coefficient.

Figure 53B:
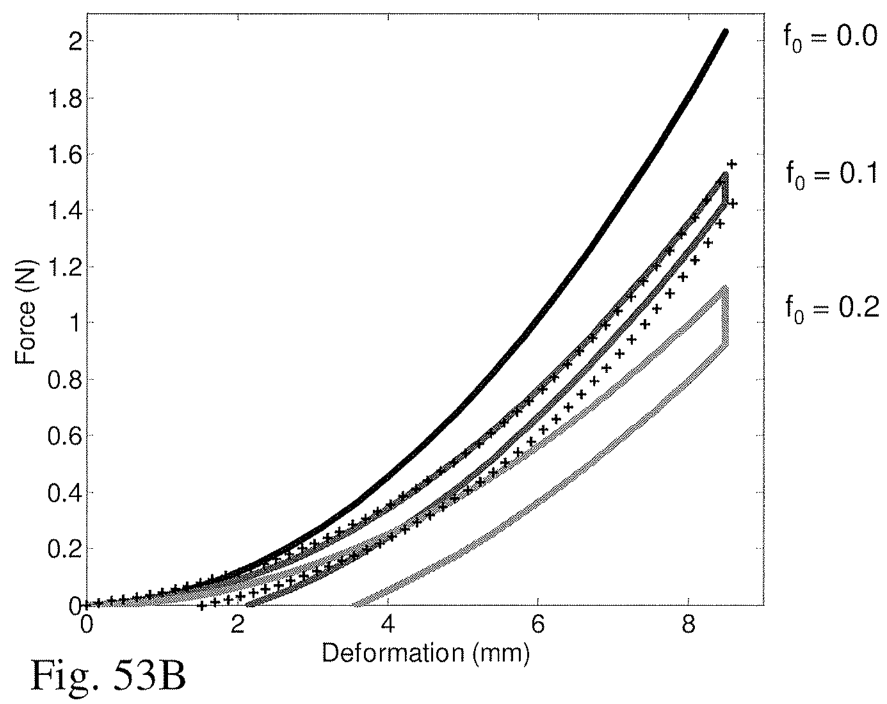
FIG. 53B is the reconstructed effective tissue stiffness curves. The stress relaxation of the membrane sample was differently set between 0.0 and 0.2. The dashed curve represents the indentation experiment result of the plot in (a)

To evaluate the accuracy of the proposed compliance estimation method in experiments, the prepared three membranes were characterized by the method of the present invention. Δs was estimated by localizing MASCE on the sample A. The stiffness coefficient was estimated using Equations (28) and (29). Because $f_0$ is unknown, it was differently set between 0 and 0.2 N. FIG. 53B shows the reconstructed stiffness curve of the membrane sample A. The indentation result (the discrete plot with the + marks) is similar to the reconstructed curve (colored by gray). Especially, the precision is dramatically improved if $f_0$ (0.1 N) is close to the actual range of the stress relaxation (0.09-0.12 N). k* (0.021 N/mm$^2$) is the same as $k_{cf}$ which was curve-fitted in the indentation experimental results. Also, their hysteresis areas are almost overlapped.

The experiments were repeated using samples B and C also. Table XI shows the summarized experimental results. The results present two points. First, even though $f_0$ is assumed to be 0, the relative comparison of the sample membrane stiffness is possible (see the fifth column). If $f_0$ is close to the actual stress relaxation of the tissue, the result becomes more accurate (compare k* in the last column with $k_{cf}$ in the second column). The actual stress relaxation of each sample is presented in the third column of Table XI.

TABLE XI

COMPARISON OF THE TISSUE STIFFNESS COEFFICIENTS

| Sample | $k_{cf}$ (N/mm$^2$) | f (N) | Δs (mm) | k* (N/mm$^2$) $f_0$ = 0 | k* (N/mm$^2$) $f_0$ = 0.1 |
|---|---|---|---|---|---|
| A | 0.021 | 0.09-0.12 | 2.7 | 0.028 | 0.021 |
| B | 0.026 | 0.11-0.12 | 2.2 | 0.042 | 0.032 |
| C | 0.047 | 0.22-0.30 | 1.8 | 0.063 | 0.048 |

*$F_{dfm}^{P}$ (measured) = 1.57 ± 0.04N; $F_{rcv}^{P}$ (measured) = 0.64 ± 0.01N

B. 3-D Mapping of Local Tissue Surface

In this section, the second new application, 3-D mapping of the local stomach surface, is introduced. MASCE employs rolling-based surface locomotion by the external magnetic field. Therefore, the localized 3-D contact points of MASCE mean the tissue surface of the stomach. If a number of contact points are connected each other, the rough geometry of the stomach could be reconstructed. However, due to the pre-loading force when MASCE is localized, only deformed stomach geometry can be estimated. For example, FIG. 52 shows that the contact points would give the inaccurate surface geometry of the stomach.

The above issue can be solved by compensating the deformation of the tissue surface using the reconstructed tissue compliance curve. $s_{rcv}$ presents the deformation of the tissue surface. The calculated $s_{rcv}$ is added on the shape deformation distance of Equation (23) as, $$D_{rcv,com} = D_{rcv} + s_{rcv} \tag{30}$$

FIGS. 54A-B shows the reconstructed 3-D map of the rubber stomach model, which was implemented by applying Equation (30). The stomach surface was reconstructed by applying the surface fitting toolbox of MATLAB to the contact points. Compared to FIG. 11B?, the deformation-compensated 3-D map is more similar to the original geometry of the stomach simulator. The compensated displacement of the stomach surface ranges from 3.3 mm to 5.8 mm.

3-D mapping of the local tissue surface could be used for path planning of MASCE. The block diagram of FIG. 42 shows that the 3-D map is updated after rolling locomotion and an operator drives EPM considering the updated 3-D map. For example, if MASCE is driven towards a sidewall or a steep slope, the EPM's path at the next step could be assigned in the backward space to move MASCE within the desired workspace. While reconstructing the 3-D map of a stomach using planar images is computationally expensive due to feature detection or optimization, the proposed 3-D mapping method results from the localized MASCE directly. Even though the proposed method does not contain a computational process, it provides the rough geometry for path planning of MASCE and EPM. Integrating simultaneous localization and mapping (SLAM) methods in mobile robotics with MASCE and the proposed localization method is a promising future work for 3-D mapping of complex surfaces such as stomach.

C. Compliance Imaging of the Local Tissue Surface

Figure 55:
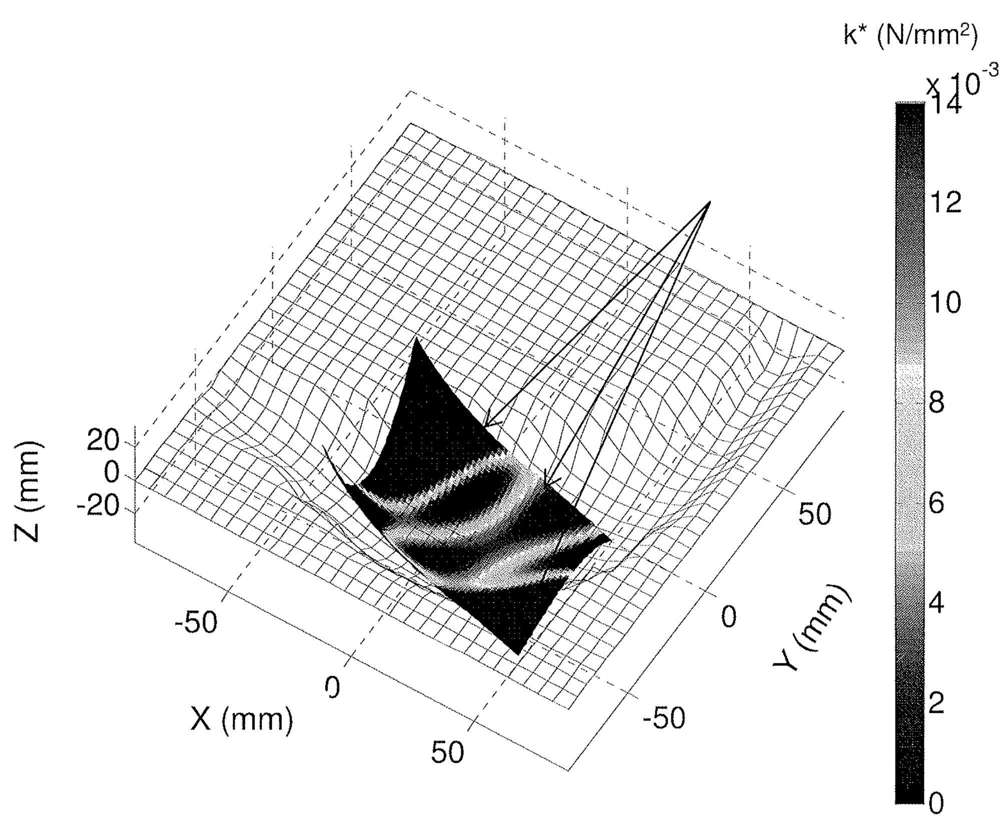
FIG. 55 illustrates interpolated relative stiffness coefficients on the reconstructed 3-D map. Measured local tissue compliance parameters overlapped with the reconstructed 3-D geometrical model of the synthetic stomach. The arrows point to regions (red) that show the relatively rigid areas.

The final step is to combine the estimated stiffness coefficient (k*) with the reconstructed 3-D map. The procedure to build the compliance map is as follows. First, a polynomial function (k*=g(x,y)) is obtained using a surface fitting function. The compliance of the rest area of the stomach model is then estimated using this polynomial function. Finally, the calculated compliance is overlapped with the reconstructed 3-D map. FIG. 55 shows the colored-map of the tissue compliance. The estimated stiffness coefficient k* can be used as a parameter to compare the compliance of the tissue. The side area of the simulator is more compliant than the flat area at the center because that area is thinner.

The combination of the estimated tissue compliance and the reconstructed 3-D map of the tissue surface could be used as a new elastography technique. Elastography is a non-invasive diagnosis method to estimate relative stiffness or strain of soft tissues in order to detect or classify tumors. A tumor or an abnormal cancerous growth is normally 5-28 times stiffer than the surrounding normal soft tissue. When a mechanical force or vibration is applied, the tumor deforms less than the surrounding tissue. Currently, elastography is implemented via MRI, X-ray or ultrasound images. However, none of these techniques can give optical camera images in addition to the relative compliance map as in the case of MASCE where visual images are the most common information for doctors to diagnose diseases inside stomach. Moreover, MASCE based elastography could be much less expensive than the MRI based elastography, much less noisy than the ultrasonic imaging (ultrasound imaging technique has drawbacks like low signal-to-noise ratio and the presence of strong wave reflectors such as bones and air pockets) based elastography, and much less invasive than X-ray based elastography, which exposes the patient to X-rays.

D. Requirements and Limitations

There are several requirements for the precise 3-D mapping of the local tissue surface and tissue compliance estimation. First, the position of stomach has to be stable in the abdomen. It was already verified that a stomach filled with water fixes its location in the abdomen, which can reduce the organ rearrangement issue during magnetic actuation. Next, a large number of data points is required to reconstruct the meaningful geometrical model of stomach. In the experiments of FIGS. 54A-B, 16 contact points were used. The way to improve the resolution of the 3-D map is to downsize MASCE and actuate it delicately to cover the whole bottom area. Finally, in order to estimate more accurate effective stiffness coefficient, the stress relaxation ($f_0$) during the transition stage needs to be investigated. Currently, the effective stiffness coefficient should be estimated assuming that $f_0$ is 0. However, as shown in FIG. 43 and Table XI, if $f_0$ is estimated well, the accuracy of the stiffness coefficient would be dramatically improved. A possible solution is to use an analytical tissue model describing the relation between the transition time and the stress relaxation.

Basically, both tissue compliance estimation and 3-D mapping of the local tissue surface are enabled by 3-D localization of MASCE. Therefore, it is important to minimize the localization error to improve the accuracy of the 3-D map and the compliance estimation. FIG. 55 shows that the proposed localization method has inherent errors, which range from 2.0-3.7 mm. The error is mainly due to the coaxial alignment error. If MASCE is distant from EPM in practice, the localization error could dramatically increase. For example, if the distance between EPM and MASCE becomes five times, the position error could increase to five times of the original one. For a more precise coaxial alignment, multiple hall-effect sensors could be embedded inside MASCE and any possible disturbances such as the tethering should be removed.

E. Compatibility with Localized Drug Release Function

Figure 56:
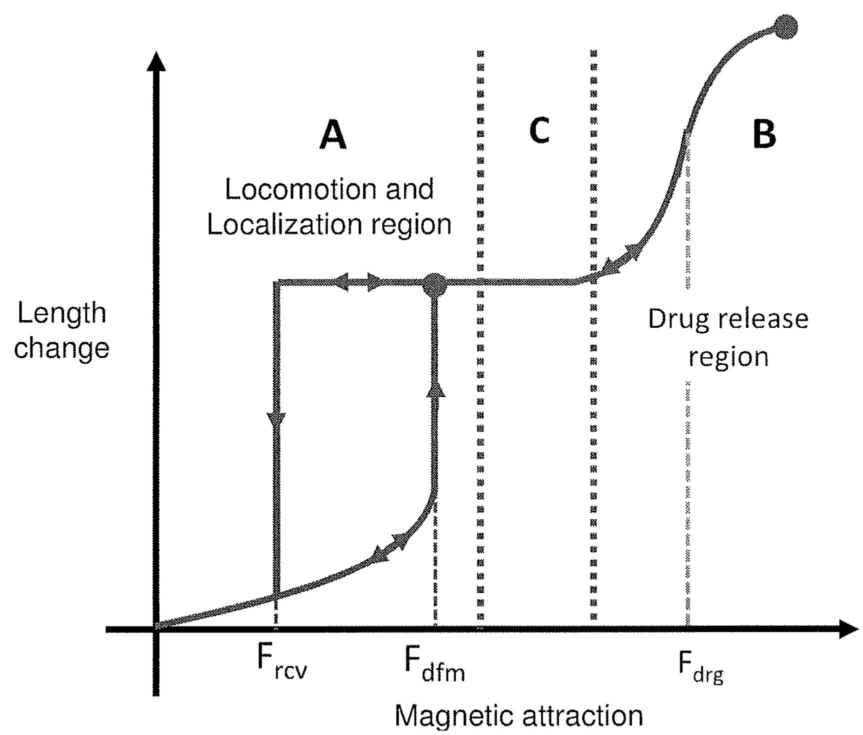
FIG. 56 is a plot of desired shape deformation and recovery curve of MASCE during rolling locomotion and 3-D localization (region A), localized drug release (region B), and force margin preventing the undesired drug release during rolling locomotion and 3-D localization (region C).

The strength of MASCE is that it can also perform localized drug release type of therapeutic functions by its axial deformation control remotely. To be able to implement localized drug release independently from 3-D localization, the critical forces for shape deformation ($F_{dfm}$), shape recovery ($F_{rcv}$), and drug release ($F_{drg}$) should be very distinct as in FIG. 56. If the stiffness of the drug chamber is high, the axial contraction during 3-D localization should not induce the undesired drug release. In the region A of FIG. 56, MASCE moves on the bottom surface of the tissue using rolling motion and its position is estimated using its shape deformation and recovery. Localized drug release is triggered by a strong external magnetic field in the region B. If the magnetic attraction is stronger than $F_{drg}$, the drug chamber is abruptly compressed and the polymeric gel is released to coat a gastric ulcer. The region C is the force margin preventing the undesired drug release during rolling locomotion.

V. Conclusion

The present invention discloses a 3-D localization method for MASCE. The method of the present invention is based on MASCE's unique compliance feature where its shape is abruptly deformed and recovered at a certain level of the external magnetic attraction. The critical force for the shape deformation (recovery) is determined by MASCE's axial compliance and the internal magnetic attraction. Therefore, MASCE has its own characteristic shape deformation (recovery) distance, which is used to estimate the distance from EPM to MASCE. In the method, MASCE can be localized between the rolling locomotion steps without a computational process requiring three-axial magnetic fields data. Therefore, the errors due to the inaccurate magnetic modeling of EPM, sensor noise, and sensor misalignment are avoided. The error of the algorithm ranges from 2 to 4 mm with the given experimental conditions. Two new applications enabled by 3-D localization were also disclosed. The first one is a 3-D geometrical modeling of the stomach surface. Such mapping can be a reference for path planning of MASCE and EPM. Also, it can be a database for disease development analysis. The second application is to characterize the local relative tissue compliance in-situ using the different deformation response of a tissue point. The estimated effective tissue stiffness coefficient can be used to detect a cancerous region. The present invention 3-D localization, tissue compliance and geometrical mapping methods can also be used in-vitro and in-vivo porcine stomachs by developing an automated magnetic actuation system and smaller diameter and untethered MASCE prototypes with on-board sensors, electronics, communication, and power towards MASCE's clinical use.

While the disclosure has been described in detail and with reference to specific embodiments thereof, it will be apparent to one skilled in the art that various changes and modifications can be made therein without departing from the spirit and scope of the embodiments. Thus, it is intended that the present disclosure cover the modifications and variations of this disclosure provided they come within the scope of the appended claims and their equivalents.

What is claimed is:

1. A compliant capsule endoscopic robot for diagnosis and treatment comprising:

a first head having a recess with an outwardly oriented open end and an exterior surface, wherein the recess is sized to receive an internal permanent magnet;

a second head having an exterior surface;

a plurality of side linkages made of resilient material capable of elastic deformation under a preload to return to an original shape upon the removal of the preload, wherein each side linkage of the plurality of side linkages includes a first end and a second end, wherein the first end of the each side linkage of the plurality of side linkages is fixedly attached to the exterior surface of the first head, wherein the second end of the each side linkage of the plurality of side linkages is fixedly attached to the exterior surface of the second head, thereby causing aligned traversal of the first head and the second head along an axis and towards a center of the compliant capsule when the plurality of side linkages deform under the preload; and only a single internal permanent magnet disposed in the recess of the first head.

2. The compliant capsule endoscopic robot according to claim 1, wherein the recess is further sized to receive an optical device with wireless communications.

3. The compliant capsule endoscopic robot according to claim 1, wherein the recess is further sized to receive an drug repository chamber, wherein the drug repository chamber comprises an outlet port to release a drug contained within the drug repository chamber when the drug repository chamber is compressed.

4. A compliant capsule endoscopic robot for diagnosis and treatment comprising:

a first head having a recess with an outwardly oriented open end and an exterior surface, wherein the recess is sized to receive in the outwardly oriented open end a first internal permanent magnet;

a second head having a recess with an open end and an exterior surface, wherein the recess is sized to receive in the open end a second internal permanent magnet; and a plurality of side linkages made of resilient material capable of elastic deformation under a preload to return to an original shape upon the removal of the preload, wherein each side linkage of the plurality of side linkages includes a first end and a second end, wherein the first end of the each side linkage of the plurality of side linkages is fixedly attached to the exterior surface of the first head, wherein the second end of the each side linkage of the plurality of side linkages is fixedly attached to the exterior surface of the second head, thereby causing aligned traversal of the first head and the second head along an axis and towards a center of the compliant capsule when the plurality of side linkages deform under the preload.

5. The compliant capsule endoscopic robot according to claim 4, wherein the first recess is further sized to receive in the outwardly oriented open end an optical device with wireless communications.

6. The compliant capsule endoscopic robot according to claim 4, wherein the first recess is further sized to receive in the outwardly oriented open end an drug repository chamber, wherein the drug repository chamber comprises an outlet port to release a drug contained within the drug repository chamber when the drug repository chamber is compressed.

* * * * *